(12) United States Patent
Wagner

(10) Patent No.: US 8,236,925 B1
(45) Date of Patent: Aug. 7, 2012

(54) PROTEIN NANORINGS

(75) Inventor: Carston R. Wagner, Saint Paul, MN (US)

(73) Assignee: University of Minnesota, Minneapolis, MN (US)

( * ) Notice: Subject to any disclaimer, the term of this patent is extended or adjusted under 35 U.S.C. 154(b) by 1596 days.

(21) Appl. No.: 11/511,186

(22) Filed: Aug. 28, 2006

Related U.S. Application Data

(60) Provisional application No. 60/711,563, filed on Aug. 26, 2005.

(51) Int. Cl.
*C07K 16/00* (2006.01)
(52) U.S. Cl. .......................... 530/323; 530/300; 530/350
(58) Field of Classification Search .................... None
See application file for complete search history.

(56) References Cited

U.S. PATENT DOCUMENTS

2002/0168685 A1* 11/2002 Cornish .......................... 435/7.1

OTHER PUBLICATIONS

Kopytek et al Chemistry and Biology vol. 7 p. 313 (2000).*
Brechbiel, "Backbone-Substituted DTPA Ligands for 90Y Radioimmunotherapy", *Bioconjugate Chem.* 2, 187-194, 1991.
Carlson, "Chemically Controlled Self-Assembly of Protein Nanorings", *J. Am. Chem. Soc.*, 128, 7630-7638, 2006.
Carlson, "Designing Protein Dimerizers: The Importance of Ligand Conformational Equilibria", *J. Am. Chem. Soc.*, 125, 1501-1507, 2003.
Dubowchik, "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity", *Bioconjugate Chem.*, 13, 855-869, 2002.
Ercolani, "Physical Basis of Self-Assembly Macrocyclizations", *J. Phys.Chem. B*, 102, 5699-5703, 1998.
Ercolani, "A Model for Self-Assembly in Solution1",*J. Phys. Chem. B.*, 107, 5052-5057, 2003.
Ghetie, "Homodimerization of tumor-reactive monoclonal antibodies markedly increases their ability to induce growth arrest or apoptosis of tumor cells", *Proc. Natl. Acad. Sci. USA*, 94, 7509-7514, 1997.
Ghetie, "Homodimers but not monomers of Rituxan (chimeric anti-CD20) induce apoptosis in human B-lymphoma cells and synergize with a chemotherapeutic agent and an immunotoxin", *Blood*, 97, 1392-1398, 2001.
Ionescu, "Multistate Equilibrium Unfolding of *Escherichia coli* Dihydrofolate Reductase: Thermodynamic and Spectroscopic Description of the Native, Intermediate, and Unfolded Ensembles", *Biochemistry*, 39, 9540-9550, 2000.
Iwakura, "A Strategy for Testing the Suitability of Cysteine Replacements in Dihydrofolate Reductase from *Escherichia coli*", *J. Biochem.*, 117, 480-488, 1995.
Iwakura, "Stability and Reversibility of Thermal Denaturation Are Greatly Improved by Limiting Terminal Flexibility of *Escherichia coli* Dihydrofolate Reductase", *J. Biochem.*, 119, 414-420, 1996.
Meng, "The Evaluation of Recombinant, Chimeric, Tetravalent Antihuman CD22 Antibodies", *Clinical Cancer Research*, 10, 1274-1281, 2004.
Milenic, "Antibody-Targeted Radiation Cancer Therapy", *Nat. Rev. Drug Disc.*, 3, 488-498, 2004.
Parker, "A practical method for building linear and cyclic triamines from (2-trimethylsilyl) ethanesulfonamides (SES-amides)", *Tetrahedron*, 59, 10165-10171, 2003.
Phanstiel, "The Effect of Polyamine Homologation on the Transport and Cytotoxicity Properties of Polyamine-(DNA-Intercalator) Conjugates", *J. Org. Chem.*, 65, 5590-5599, 2000.
Sachdev, "A Chimeric Humanized Single-Chain Antibody against the Type 1 Insulin-like Growth Factor (IGF) Receptor Renders Breast Cancer Cells Refractory to the Mitogenic Effects of IGF-I", *Cancer Research*, 63, 627-635, 2003.
Sticha, "Overexpression and Large-Scale Purification of Recombinant Hamster Polymorphic Arylamine N-Acetyltransferase as a Dihydrofolate Reductase Fusion Protein", *Protein Expression and Purification*, 10, 141-153, 1997.
Vallera, "Radiotherapy of CD19 Expressing Daudi Tumors in Nude Mice with Yttrium-90-Labeled Anti-CD19 Antibody", *Cancer Biother. Radiopharm.*, 19, 11-23, 2004.
Vallera, "A Bispecific Recombinant Immunotoxin, DT2219, Targeting Human CD 19 and CD22 Receptors in a Mouse Xenograft Model of B-Cell Leukemia/Lymphoma", *Clincal Cancer Research*, 11, 3879-3888, 2005.
Vallera, "Radioimmunotherapy of CD22-Expressing Daudi Tumors in Nude Mice With A 90Y-Labeled Anti-CD22 Monoclonal Antibody", *Clinical Cancer Research*, 11, 7920-7928, 2005.
Waschutza, "Engineered disulfide bonds in recombinant human interferon-y: the impact of the N-terminal helix A and the AB-loop on protein stability", *Protein Engineering*, 9, 905-912, 1996.
White, "Total Synthesis of (−)-7-Epicylindrospermopsin, a Toxic Metabolite of the Freshwater Cyanobacterium *Aphanizomenon ovalisporum*, and Assignment of Its Absolute Configuration",*J. Org. Chem.*, 70, 1963-1977, 2005.
Yeates, "Designing supramolecular protein assemblies", *Cur. Opin. Struc. Biol.*, 12, 464-470, 2002.
Zhang, "Design of nanostructured biological materials through self-assembly of peptides and proteins", *Cur. Opin. Chem. Biol.*, 6, 865-871, 2002.

* cited by examiner

*Primary Examiner* — Sheela J Huff
(74) *Attorney, Agent, or Firm* — Viksnins Harris & Padys PLLP

(57) ABSTRACT

The invention provides protein nanorings.

58 Claims, 7 Drawing Sheets

A. Assembly Mechanisms

B. DHFR₂ Variants

A

B

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Leu Gly Gly Gly Gly Gly Leu Val Pro Arg Gly Thr
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Leu Gly Gly Gly Gly Thr
1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Gly Glu Asn Leu Tyr Phe Gln Gly Ile Gly Leu Asp
1               5                   10
```

PROTEIN NANORINGS

RELATED APPLICATION

This patent document claims the benefit of priority of U.S. application Ser. No. 60/711,563, filed Aug. 26, 2005, which application is herein incorporated by reference.

STATEMENT OF GOVERNMENT SUPPORT

Work related to the present invention was funded by the U.S. government (NIH Grant CA89615). The government may have certain rights in the invention.

SEQUENCE LISTING

The instant application contains a Sequence Listing which has been submitted in ASCII format via EFS-Web and is hereby incorporated by reference in its entirety. Said ASCII copy, created on Mar. 1, 2012, is named 09531US1.txt and is 973 bytes in size.

BACKGROUND

The engineering of synthetic nanostructures for biomedical or bioelectronic applications is likely to require the use of multiple building materials, just as living systems rely on nucleic acids for information content and proteins for chemical and functional diversity. As such, it is critical to advance the science of self-assembly in multiple biochemical realms. To date, only DNA has seen extensive use as a building material for studies of self-assembly, selected for the well-understood and robust structural specificity of sequence recognition. DNA sequences that form two-dimensional arrays, a three-dimensional octahedron, and even enzyme-like structures have been described. Recently, the greater richness of RNA secondary structure has been exploited to create intricately patterned nano-building blocks.

Nucleic acids, however, play a secondary role in biological nanomaterials. Following nature's lead, several early efforts to design self-assembling protein architectures have been described. To date, these synthetic protein assemblies have chiefly recapitulated biological assembly mechanisms, forming filaments from self-complementary β-strands, coiled coils, or helix bundles, or symmetric nanostructures assembled from naturally multimeric proteins.

Designing and producing biological based assemblies that can be used for the fabrication of advanced materials is a rapidly advancing area of research. Self-assembling DNA and protein biomolecular building blocks have been used to produce a number of novel nanomaterials that may be applied to microelectronics, tissue engineering and drug delivery. Because of the well-understood set of rules governing nucleic acid duplex assembly, substantial advances have been made toward the development of DNA based nanostructures. Although the potential for a greater variety of structural and, therefore, functional uses can be envisioned for protein based materials, current methods are highly idiosyncratic to the protein monomers of choice, as well as unable to provide readily available homogenous materials.

Thus, the adaptation of protein nanostructures into useful tools will require further advances in the preparation of homogeneous components, as existing methods have not fully addressed the challenges of both polydispersity and incomplete assembly. Additionally, there is broad interest in methods capable of reliable patterning materials on the 5-50 nm scale, a size regime inaccessible to current techniques.

Thus, there is currently a need for protein-based nanostructures.

SUMMARY OF CERTAIN EMBODIMENTS OF THE INVENTION

The present invention provides a composition comprising:
one or more compounds of formula I (A-$L_1$-B); and
one or more compounds of formula II (X-$L_2$-Y);
wherein;
A is a polypeptide;
B is a polypeptide;
$L_1$ is a linker;
X is a ligand that specifically binds to at least one of A or B;
Y is a ligand that specifically binds to at least one of A or B; and
$L_2$ is a linker.

In some embodiments of the invention, A and B are the same polypeptide. In some embodiments of the invention, A and B are different polypeptides. In some embodiments of the invention, X and Y are the same ligand. In some embodiments of the invention, X and Y are different ligands. In some embodiments of the invention, one or more compounds of formula I are bound to one or more compounds of formula II to form an oligomer of formula III (A-$L_1$-B-X-$L_2$-Y)$_n$ wherein: n is an integer from about 1-20. In some embodiments of the invention, n is an integer from 1-8. In some embodiments of the invention, the oligomer is substantially linear. In some embodiments of the invention, the oligomer is substantially spherical. In some embodiments of the invention, the oligomer is a nanoring.

In some embodiments of the invention, at least one of A or B is a dihydrofolate reductase (DHFR) molecule. In some embodiments of the invention, the DHFR molecule is a wild-type DHFR molecule. In some embodiments of the invention, both A and B are wild-type DHFR molecules. In some embodiments of the invention, at least one of the DHFR molecules is a mutated DHFR molecule. In some embodiments of the invention, both of the DHFR molecules are mutated DHFR molecules. In some embodiments of the invention, the DHFR molecules are *E. coli* DHFR molecules.

In some embodiments of the invention, $L_1$ is a polypeptide. In some embodiments of the invention, the polypeptide is from 1 to 13 amino acids in length. In some embodiments of the invention, the polypeptide is from 1 to 3 amino acids in length.

In some embodiments of the invention, the compound of formula I further comprises at least one single chain variable region (scFv). In some embodiments of the invention, the scFV selectively recognizes an antigen on a cancer cell. In some embodiments of the invention, the scFV is an anti-CD9, anti-CD22, or an anti-IGF 1R scFV.

In some embodiments of the invention, at least one of X or Y is a methotrexate molecule, or an analog thereof.

In some embodiments of the invention, the compound of formula II further comprises a therapeutic agent. In some embodiments of the invention, the therapeutic agent is an anticancer or antiviral agent. In some embodiments of the invention, the anticancer agent is doxorubicin or auristatin or a radiotherapeutic agent.

In some embodiments of the invention, the compound of formula II further comprises a detectable agent.

Certain embodiments of the invention also provide a fusion protein comprising two dihydrofolate reductase (DHFR) molecules linked via a linker. In some embodiments of the invention, at least one of the DHFR molecules is a wild-type DHFR molecule. In some embodiments of the invention, both of the DHFR molecules are wild-type DHFR molecules. In some embodiments of the invention, at least one of the DHFR molecules is a mutated DHFR molecule. In some embodiments of the invention, both of the DHFR molecules are mutated DHFR molecules. In some embodiments of the invention, the DHFR molecules are E. coli DHFR molecules.

In some embodiments of the invention, the linker is a polypeptide. In some embodiments of the invention, the polypeptide is from 1 to 13 amino acids in length. In some embodiments of the invention, the polypeptide is from 1 to 3 amino acids in length.

In some embodiments of the invention, the fusion protein may further comprise at least one single chain variable region (scFv). In some embodiments of the invention, the scFV selectively binds to an antigen on a cancer cell. In some embodiments of the invention, the scFV is an anti-CD9, anti-CD22, or an anti-IGF 1R scFV.

Certain embodiments of the invention also provide polynucleotides encoding the fusion protein of the invention. Certain embodiments of the invention also provide expression vectors comprising a polynucleotide of the invention operably linked to a promoter. Certain embodiments of the invention also provide cells comprising the fusion protein, polynucleotide, and/or expression vector, of the invention.

Certain embodiments of the invention also provide an oligomer comprising at least one fusion protein of the invention and at least one methotrexate conjugate that comprises two methotrexate molecules, or analogs thereof, linked together by a linker. In some embodiments of the invention, the methotrexate conjugate further comprises a detectable group. In some embodiments of the invention, the methotrexate conjugate further comprises an additional agent. In some embodiments of the invention, the additional agent is a therapeutic agent. In some embodiments of the invention, the therapeutic agent is an anticancer or antiviral agent. In some embodiments of the invention, the anticancer agent is doxorubicin or auristatin or a radiotherapeutic agent. In some embodiments of the invention, the oligomer may comprise a plurality of fusion proteins of the invention. In some embodiments of the invention, the oligomer is substantially linear. In some embodiments of the invention, the oligomer is substantially spherical. In some embodiments of the invention, the oligomer is a nanoring. In some embodiments of the invention, the oligomer is a dimer, a trimer, a tetramer, and pentamer, or an octamer. In some embodiments of the invention, the oligomer comprises a plurality of fusion proteins that comprise at least one single chain variable region (scFv).

Certain embodiments of the present invention also provide a methotrexate conjugate comprising: two methotrexate molecules, or analogs thereof, linked together by a linker; and at least one additional agent. In some embodiments of the invention, the additional agent is a detectable group. In some embodiments of the invention, the additional agent is a therapeutic agent. In some embodiments of the invention, the additional agent is an anticancer or antiviral agent. In some embodiments of the invention, the anticancer agent is doxorubicin or auristatin or a radiotherapeutic agent.

Certain embodiments of the present invention also provide pharmaceutical compositions comprising a composition, protein, polynucleotide, expression vector, cell, oligomer and/or conjugate of the invention and a pharmaceutically acceptable carrier.

Certain embodiments of the present invention also provide a method for killing a cancer cell, comprising contacting the cancer cell in vitro or in vivo with an effective amount of a composition or oligomer of the invention.

Certain embodiments of the present invention also provide a method for treating cancer in a patient (e.g., a mammal, e.g., a human), comprising administering to the patient an effective amount of the composition or oligomer of the invention.

In some embodiments of the invention, the cancer is breast cancer. In some embodiments of the invention, the cancer is leukemia. In some embodiments of the invention, the cancer is lymphoma. In some embodiments of the invention, the cancer is B lineage lymphoblastic leukemia (B-ALL).

Certain embodiments of the present invention also provide a protein, polynucleotide, expression vector, cell, oligomer, conjugate, and/or composition of the invention for use in medical treatment or diagnosis.

Certain embodiments of the present invention also provide the use of a protein, polynucleotide, expression vector, cell, oligomer, conjugate, and/or composition of the invention to prepare a medicament useful for treating cancer in an animal.

DETAILED DESCRIPTION

The exploitation of biological macromolecules, such as nucleic acids, for the fabrication of advanced materials is a promising area of research. Although a greater variety of structural and functional uses can be envisioned for protein-based materials, systematic approaches for their construction have yet to emerge.

As described herein, in the presence of dimeric methotrexate, dihydrofolate reductase molecules tethered together by a flexible peptide linker spontaneously form highly stable cyclic structures with diameters, e.g., ranging from 8 to 20 nm. The nanoring size is affected by the length and composition of the peptide linker, on the affinity and conformational state of the dimerizer, and on induced protein-protein interactions.

Figure 1:
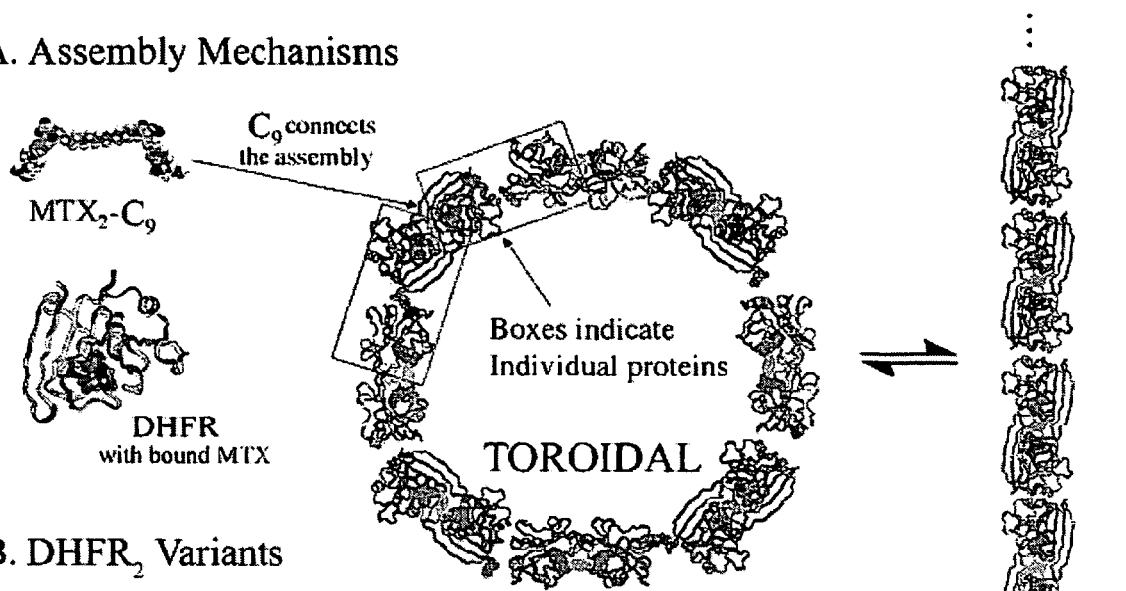
FIG. 1. Assembly of ecDHFR2 and MTX2-C9. (A) The individual components and proposed assembly mechanisms of the bisMTX and DHFR2 system are diagrammed. The conformational flexibility of the growing chain and thermodynamics of its connections will regulate the balance between cyclic and linear oligomers of 1DD-G and MTX2-C9. (B) Beginning with the 13DD plasmid ($GLG_5LVPRGT$) (SEQ ID NO: 1), the DNA encoding the inter-DHFR linker was successively truncated by QuikChange mutagenesis to yield 7DD ($GLG_4T$) (SEQ ID NO: 2), 3DD (GGT), 1DDG (G), and 1DDT (T). The images provide a graphical comparison of the relative linker proportions.
Figure 1:
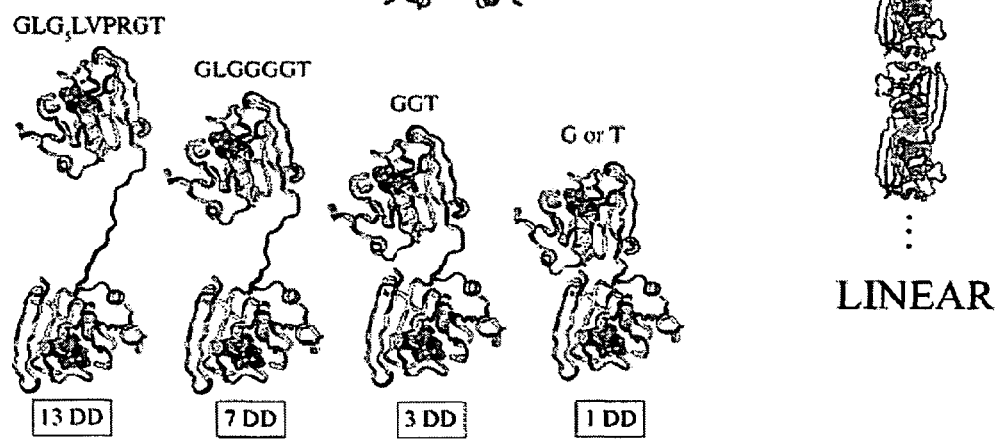

As described herein, the intrinsic ligand-binding ability of many proteins offers a means to direct nanostructure assembly. Just as DNA sequence recognition and protein-protein interactions have evolved to pick one target out of a complex background, so too have drug molecules been designed to target one protein among many. Thus, as described herein, the construction of reversible proteinaceous nanostructures was explored. This work relates to the use of chemical inducers of protein dimerization (CIDs), bivalent drug molecules that simultaneously bind and connect two proteins. As illustrated in FIG. 1A, by assembling a bivalent (or multivalent) protein and a bivalent ligand, protein-drug recognition creates a selective structural linkage and can produce cyclic or linear structures.

Nanorings

The control of protein-protein interactions is a necessary requirement for cellular biological processes. Protein oligomerization and dimerization initiated by small molecules and peptides plays an important role in regulating signal transduction, gene expression, and metabolic processes. Several examples of small molecule inducers of the intracellular dimerization of fusion proteins have been used to control gene expression, modulate cell membrane receptor signaling, and even to search for novel biocatalysts. Antibodies have also been used to cross-link cell surface receptors in order to modulate cell-cell interactions. Nevertheless, the use of small molecules for the induction and control of cell surface receptor or cell-cell interactions is largely unexplored. In principle, cell surface interactions could be directed or redirected by chemical self-assembly of receptor specific protein supramolecular complexes, such as polyvalent antibodies. Antibodies arrayed on homogenous nanostructures would provide a method for oligomerizing receptors in to precisely defined nanoassemblies on cell surfaces.

Designing and producing biological based assemblies that can be used for the fabrication of advanced materials is a rapidly advancing area of research. Self-assembling DNA and protein biomolecular building blocks have been used to produce a number of novel nanomaterials that may be applied to microelectronics, tissue engineering and drug delivery. Because of the well-understood set of rules governing nucleic acid duplex assembly, substantial advances have been made toward the development of DNA based nanostructures. However, the potential for a greater variety of structural and, therefore, functional uses exists for protein based materials.

To understand how to control protein supramolecular self-assembly, a general protocol for the chemical induction of stable protein dimers and oligomers has been developed, as described herein. Non-cytotoxic, homo-bifunctional dimers of methotrexate ($MTX^2$) were synthesized, and it was found that they are able to stably dimerize E. coli DHFR by relying on a set of induced cooperative protein interactions, as well as ligand binding. Based on these studies, it was determined that protein dimerizer or oligomerizer design should consider ligand binding, cooperative protein-protein interactions, and the conformational state of the ligand. This set of observations has been extended by demonstrating that E. coli DHFR molecules that have been tethered together by a 13, 7, 3, or 1 amino acid peptide linker (wtDHFR$^2$) are capable of spontaneously oligomerizing, in the presence of $MTX^2$, to form highly stable cyclic dimers, trimers, and larger rings from tetramers through octamers with diameters ranging from about 5 to at least 100 nm, e.g., from about 8 to about 30 nm.

Consequently, given the framework developed for understanding induced protein dimerization and the utility of a method for the controlled induction of cell surface receptor oligomerization, a general strategy for the design of chemically assembled antibody nanorings for the site specific delivery of potent anti-tumor drugs has been developed.

Small molecule-induced assembly of protein supramolecular complexes is thus affected by the induction of stabilizing protein-protein interactions, e.g., by a tight binding bivalent ligand capable of inducing persistent and durable monomer connectivity over a wide range of ligand concentrations. The methotrexate-dihydrofolate reductase CID system fulfills these characteristics: bivalent methotrexate (bis-MTX) derivatives bind to DHFR with picomolar affinity, forming robust complexes stabilized by protein-protein interactions. The ability of the free bisMTX ligands to adopt a stable folded conformation in solution significantly reduces the ligand-concentration dependence of induced protein assembly. A set of DHFR fusion proteins with varying inter-domain linker lengths was designed, and their bisMTX-mediated self-assembly into proteinaceous nanostructures was characterized. Thus, a method for the preparation of stable and homogeneous protein polygons, or nanorings has been developed. In particular, DHFR molecules, when fused together by a peptide chain of variable length, were found to spontaneously self-assemble in to protein macrocycles after treatment with a dimeric enzyme inhibitor ($MTX^2$) that efficiently dimerizes DHFR. The size of the nanoring (8-30 nm diameter) was affected by the length of the linker peptide between the two DHFRs. Since the amino and carboxy terminus of DHFR are on the opposite face of the MTX binding site, DHFR nanorings afford an excellent scaffold for arraying fusion proteins, such as recombinant single chain antibodies (scFV) and anticancer therapeutics linked to the chemical dimerizer. Among other utilities, the nanorings may be used to orient semiconductor binding peptides to chips, to prepare precisely bound and oriented metal particles, or for prodrug activation.

Recombinant Antibodies

The development by Kohler and Milstein of monoclonal antibodies (Mabs) by hybridoma production stands as one the major biomedical accomplishments of the last century. Mabs have been most extensively used as research tools for the selective identification and isolation of proteins from complex mixtures of biomacromolecules such as tissues. Recently, Mabs have begun to finally fulfill their promise as "magic bullets" for the treatment human diseases. Since 1986, fifteen monoclonal antibodies have been approved by the FDA for the treatment of tissue rejection, cardiovascular disease, viral diseases, breast cancer and leukemias. Up until the early 1990's, the development of therapeutic Mabs was hampered by the development of a human anti-mouse antibody (HAMA) immune response in patients dosed with these drugs. The escalating number of clinically approved Mabs has largely resulted from advances in protein engineering techniques capable of humanizing mouse antibodies.

For all of the advances that have been made with Mabs, there are limitations, particularly with regard to their specificity for a single antigen and size. In theory, antibodies capable of targeting more than one antigen would be very useful for enhanced specificity to a target tissue or in re-directing cell-cell interactions. The first bispecific antibodies were produced by a variation of hybridoma methods referred to as quadroma technology, in which two different hybridoma cell lines, which produce two different Mabs, are fused. Random pairing of the chains by the quadroma cells results in ten different antibodies, one of which is a true bispecific Mab. Although the antibodies generated by this method are truly monoclonal antibodies, the elaborate purification protocols required to obtain the bispecific Mab, as well as the need for continued maintenance of quadroma cell lines is a serious obstacle to the utility of this method for routine bispecific Mabs production. In addition, they contain the Fcγ region, which may or may not be biologically useful. Removal of the Fcγ region by proteolysis with pepsin, can reduce the deleterious side effects associated with the Fcγ region. Fabs from two different Mabs have also been isolated and their hinge regions chemically conjugated via the available terminal cysteines.

The ability to clone and express the variable ($V_H$ & $V_L$) and constant ($C_H$ & $C_L$) domains of Mabs has made the construction of genetically engineered and considerably smaller antibodies possible. Fabs have been fused to the leucine zipper regions of the transcription factors Jun and Fos, upon expression in E. coli bispecific Fabs could be isolated after dissociation and reassociation steps. Other associating protein domains, such as the $C_k$ and $C_{H1}$ domains of IgG have also been used successfully to produce bispecific Fabs in bacteria. Smaller antibodies fashioned from variable regions (Fv) have been constructed, expressed in E. coli and yeast and shown to be able to bind both small antigens, such as haptens, as well as proteins. Taking this a step further, a wide array of recombinant bivalent antibodies have been designed and prepared by fusing two or more Fv's. Diabodies have been assembled from $V_H$ and $V_L$ domains of two different Mabs that have been fused together by a peptide short enough to favor dimer association. E. coli and CHO cells have been shown to express substantial quantities of diabodies with yields of as much as 0.7 mg per liter of media and 15 mg per liter, respectively. Tetravalent antibodies, referred to as Tandabs, have been successfully produced by a similar design rationale. Besides their enhanced biological activity, these larger species have been shown to have a greater plasma half-life in mice than diabodies. Diabodies fused to the self-associating $C_{H3}$ domain of the Ig Fc region have been used to prepare tetravalent diabodies.

Single chain Fv's (scFv's) have been constructed by fusing the $V_H$ and $V_L$ domains of an Fv via a peptide linker. This advance has allowed diabodies consisting of a single polypeptide to be obtained. Bivalent scFv's have also been produced by capitalizing on their ability to selectively heterodimerize protein domains. Antibody $C_{H1}$ and $C_L$ domains have been fused to scFv yielding bivalent scFv's. The design of highly stable heterodimer protein interfaces as a means of controlling heterodimer formation has also been pursued. Re-engineering of the interface of one $C_{H3}$ domain to contain a bulky tyrosine, or "knob". which is able to fill a crevice or "hole" engineered into another $C_{H3}$ domain, has been a successful strategy for the self-assembly of bivalent scFv.

Although not a way of producing bispecific antibodies, scFv streptavidin fusion proteins, referred to as streptabodies, have been developed and used as pre-targeting agents for biotinylated radionuclei. In several cases this strategy has provided highly efficacious diagnostic and therapeutic tools. A variation on this theme has been the self-assembly of tetravalent streptabodies by the incubation of streptavidin with biotinylated scFv's.

Despite the success of the variety of approaches to produce multivalent antibodies mentioned thus far, the overall approach of relying on either sophisticated tissue culture techniques or recombinant genetic engineering impose a number of constraints on the future design of multispecific antibodies. Although a tetravalent diabody has been produced, in general it is difficult to produce heteromultimeric bispecific antibodies other than heterodimeric species. For each example, the desired protein must be individually isolated and purified, with little capability of altering antibody specificity, except by mutagenesis and protein engineering experimentation. Streptabodies have significantly increased the valency, but there is little ability to increase or reduce the valency beyond four. Streptabodies can somewhat address this issue, however, they must be monospecific and cannot be easily engineered to display more than one specify. In addition, the ability to use these agents, with the exception of streptabodies, to deliver a therapeutic drug requires the tedious use of chemical conjugation protocols, which can lead to heterogeneous materials.

Antibody-nanorings will be assembled with radionuclide chelating $MTX^2$ dimerizers that will provide a number of advantages over conventional radioimmunotherapeutics. Some of these advantages include; ease of polyvalent species preparation, pharmacologically controllable circulation half lives, molecular homogeneity, imaging and therapeutic capabilities, compatibility with immunoreactivity, lower in vivo toxicity, and the potential to incorporate bispecificity. accomplish this objective, we will carry out the following specific aims. Thus, described herein is the design and synthesis of methotrexate dimer (MTX2) conjugates of; a) the fluorophore, Alexa Fluor 488, and b) the radiolabeling chelator, 1B4M-diethylene-triaminepentaaceticacid (DTPA). Further described is the design, assembly and functional characterization of anti-CD22 DHFR-DHFR (DHFR2) based polyvalent Nanorings. Also described is the design and characterization of a set of DHFR2-MTX2 heterodimer building blocks for co-polymer nanoring assembly made by inserting ionic pair forming amino acids at the protein-protein interface.

The targeted delivery of radionuclides by MAB and recombinant antibodies is potentially powerful diagnostic and therapeutic approach, particularly for cancer. Radioimmunoscintigraphy with scFvs and diabodies attached to γ-emitters (Tc-99m, I-123, or In-111) or positron emitters (F-18, Cu-64, Ga-68, Y-86 or I-124) have proved to be excellent tumor imaging agents. Antibody target-delivery of α-emitters (Bi-213 or At-211) or β-emitters (I-131, Lu-177, Cu-67 or Y-90) to cancer tissues has also proven to be effective anticancer agents, particularly for the treatment of drug resistant tumors. For example, murine MABs coupled to Y-90 and I-131, respectively, have been recently FDA approved for the treatment of CD-20 positive B-cell non-Hodgkin lymphoma. Nevertheless, the slow blood clearance of MABs has contributed to non-target organ toxicities and their marginal utility as imaging agents. The design of smaller more rapidly cleared radiolabeled recombinant antibodies, such as scFvs and diabodies have proved to be better imaging agents than MABs, but ineffective as radioimmunotherapeutics. The addition of Fc regions to scFv's has shown promise as an approach to constructing dual imaging and therapeutic agents. In a clever strategy, fusion proteins of strepavidin and scFv's have been used to pre-target radionuclides to tumor tissues. Despite their success, the usefulness of radionuclide and drug conjugated antitumor antibodies would be greatly enhanced by the development of an approach that would; 1) facilitate preparation of antibodies with a range of valencies, while incorporating bispecificity, 2) allow for the pharmacological control of blood and tissue clearance rates, and 3) be amenable to the development of both imaging reagents and therapeutic drugs.

The approaches thus far described for antibody and radionuclide construction have a number of limitations. The ability to construct antibodies with valences above two has been limited and no antibodies with valences greater than four have been prepared. Moreover, the production of bispecific antibodies has not been straightforward, requiring substantial effort to produce a desired divalent bispecific combination. In principle, nanoparticles conjugated to antibodies could be used as drug/radionuclide delivery vehicles. A methodology is presented herein that allows for the controlled self-assembly of homogenous and stable antibody-nanoparticles that can incorporate bispecificity, while being amenable to pharmacological disassembly, thus advancing the utility of antibody based drugs and pharmacological tools.

To address this challenge, DHFR$^2$ molecules fused to a single chain antibody (scFv) and binds to the B-cell lymphoma and leukemia antigen CD22. (Vallera et al., 2005) DHFR$^2$-anti-CD22 scFv's fusion proteins will be prepared that are able to self-assemble into bivalent, tetravalent or octavalent species in the presence of a methotrexate dimerizer coupled to a fluorophore or chelated radionuclides. The antibody-nanorings will be able to selectively bind and undergo intracellular B-leukemia cell uptake and trafficking in vitro. In addition, the in vivo biodistribution of the antibody Nanorings will be determined, as well as the ability of timethoprim, a non-toxic *E. coli* DHFR inhibitor, to promote oligomer disassembly in vivo. The anti-tumor properties of the DHFR$^2$-anti-CD22 scFv nanorings will be determined with a mouse xenograft tumor model. Using molecular modeling and protein engineering principles, DHFR molecules capable of heterodimerization will be produced. These mutant DHFRs will be used to prepare self-assembling bispecific antibody nanorings. The antibody-radionuclide nanorings will be capable of detecting and treating a wide range of cancers.

Immunotoxin and Antibody Drug Conjugate

Monoclonal antibodies and recombinant antibodies have been used to deliver a variety of toxins, drugs and radionuclide to cancer tissues. Immunotoxins are generally prepared from antibodies or cytokines attached to catalytic toxins, such as diphtheria toxin. Toxins fused to scFv's have been made and shown to be highly potent anticancer agents. These are unique agents, since only one to two molecules are needed to kill a cell. Although hailed for their therapeutic potential, their toxicity and narrow therapeutic window have limited their therapeutic potential. Recently, because of their enhanced tumor targeting characteristics, bispecific scFv-immunotoxins have shown promise as anticancer agents. The targeting of drugs to tumors by conjugation to intracellularly cleavage linkers has been a successful antitumor approach. For example, Mylotarg is composed of an antibody to CD33 that has been conjugated to the potent DNA alkylation compound, calicheamicin through an acid-labile hydrozone. Mylotarg was the first FDA approved antibody drug conjugate and indicated for use against acute myeloid leukemia. Several other drugs, such as doxorubicin, maytansinoid, CC-1065, taxoids, and auristatin have been coupled to antibodies and shown potential efficacy as anticancer drug. Interestingly, scFv's coupled to drugs have not been reported. Nevertheless, fusion proteins of strepavidin and scFv's can be used to target radionuclides and potentially drugs to tumor tissues. Despite their success in animal tumor models, antibody drug conjugates suffer from a number of limitations, such as, inadequate potency, linker instability and molecular heterogeneity. Only recently have useful procedures become available for site-specifically conjugating antibodies to drugs.

The approaches thus far described for antibody construction have a number of limitations. The ability to construct antibodies with valences above two has been limited, and no antibodies with valences greater than four have been prepared. In principle, antibodies with a wide range of valences would allow an assessment of their differences in affinity, cellular uptake and in vivo pharmacokinetic properties to be investigated. In general, the production of bispecific antibodies has not been straight forward, requiring substantial effort to produce a desired bispecific combination. A procedure that would allow for the production of individual components to be produced and then self-assembled into a desired multivalent antibody with the ability to be mono- and bispecific would be of great value for the preparation of antibody based pharmacological tools and drugs.

This challenge can be addressed by employing the discovery of how to construct chemically induced protein nanorings. DHFR-DHFR (DHFR$^2$) fusion proteins with a propensity to form known ring sizes will be fused to two well described scFv's that bind to the B-cell antigens CD19 and CD22. scFv's to CD19 and CD22 are capable of delivering diphtheria toxin to cancer cells. DHFR$^2$-scFv's fusion proteins will be prepared with the scFv's for CD19 and CD22. Their ability to self-assemble, e.g., into bivalent, tetravalent or octavalent species, in the presence of a MTX$^2$ that may be coupled to anticancer drugs such as doxorubicin and auristatin will be assessed. The ability of the antibody-drug nanorings to selectively kill cancer cells such as B-leukemia cells will be demonstrated. Guided by molecular modeling, chemically induced DHFR heterodimers will be developed by re-designing the DHFR dimer protein interface. The heterodimers will then be used to build self-assembling co-polymer multivalent bispecific DHFR$^2$-scFv's for enhanced drug targeting.

Breast Cancer

Disruption of growth regulatory signaling in breast cancer has proven to be a successful therapeutic strategy. Activation of estrogen receptor-α (ER) by estradiol is growth stimulatory in breast cancer cells. In addition to hormonal agents, chemotherapy has been developed to disrupt cancer proliferation. Some agents depend on cellular entry into the cell cycle. Since estradiol stimulates progression through the cell cycle, there was an initial attempt to "prime" breast cancer cells with estrogens before instituting cell cycle specific chemotherapy. However, these strategies were largely unsuccessful because it was difficult to inhibit the growth regulator pathways initially activate by estradiol. Thus, approaches that increase the utility and efficacy of cell-cycle dependent drugs would clearly increase the number of therapeutic options available for breast cancer. The development of anti-IGF1R nanorings capable of the simultaneous delivery of the potent cell-cycle dependent drugs methotrexate and auristatin will address this unmet need in a unique and versatile way, while providing a general strategy for the future development of antibody-drug conjugate nanorings for other cancers as well.

Enhancing Chemotherapy Efficacy in Breast Cancer

The decline in breast cancer mortality over the last 15 years has been largely attributed to the use of systemic therapy after surgical resection of the primary tumor. Adjuvant chemotherapy and hormonal therapy reduces risk of recurrence and mortality, presumably by eradicating subclinical micrometastatic disease. Advances in adjuvant chemotherapy have included the use of combination chemotherapy, duration of chemotherapy, and scheduling of drug delivery.

Since cancer chemotherapy generally targets events required for progression through the cell cycle (nucleotide synthesis, DNA replication, tubulin function), there has been an attempt to increase the proliferative rate of breast cancer cells prior to administration of cell cycle specific cancer chemotherapies. In these early studies, patients with advanced metastatic disease were first treated with tamoxifen to arrest and synchronize cells. Cells were then "released" from this cell cycle arrest with Premarin followed by administration of chemotherapy. The bulk of these "estrogen priming" trials used cell cycle specific chemotherapies, such as fluorouracil and methotrexate, with the idea that entry of breast cancer cells into S-phase would be of benefit. While the initial reports of this combined chemohormonal therapy appeared promising, it was difficult to discern a clear benefit to estrogen priming. One potential difficulty with this strategy was the relatively cumbersome scheduling of drugs required to achieve the priming effect. Secondly, since tamoxifen is an incomplete antagonist of the estrogen receptor α (ER), there wasn't a facile way to turn off the signaling pathways activated by estrogens.

However, it is clear that hormonal therapy can affect chemotherapy function. The most recent example of this interaction is a clinical trial examining the concurrent use of chemotherapy and tamoxifen in the adjuvant setting was inferior to the use of tamoxifen followed by chemotherapy. It is felt that tamoxifen inhibits the effects of chemotherapy by arresting cells in G0 or G1 rendering cells relatively resistant to cell-cycle specific chemotherapy. Thus, manipulation of cell cycle kinetics could lead to enhanced efficacy of chemotherapy.

It is noteworthy that combination of chemotherapy with the monoclonal antibody trastuzumab has recently been shown to be superior to the use of chemotherapy alone in the adjuvant treatment of women with lymph-node positive disease. While the full data have not yet been published, it appears that the use of paclitaxel concurrently with trastuzumab was a superior treatment. While the exact mechanism for trastuzumab's clinical effects have not yet been fully elucidated, recent data suggest that this antibody induces apoptosis in primary breast cancers. Thus, administration of a pro-apoptotic antibody with a pro-apoptotic chemotherapeutic agent may maximize tumor response.

Self-Assembling Protein Nanorings

Antibodies have been used to cross-link cell surface receptors in order to modulate cell-cell interactions. In principle, cell surface interactions could be directed or redirected by the chemical self-assembly of receptor specific protein supramolecular complexes, such as polyvalent antibodies. Antibodies arrayed on homogenous nanostructures would provide a method for oligomerizing receptors in precisely defined nanoassemblies on cell surfaces. As described herein, a general protocol for the chemical induction of stable protein dimers and oligomers has been developed. Non-cytotoxic, homo-bifunctional dimers of methotrexate that contain a 9 or 12 methylene linker, ($MTX^2$-C9 or $MTX^2$-C12) have been synthesized and are able to stably dimerize E. coli DHFR by relying on a set of induced cooperative protein interactions, as well as ligand binding. E. coli DHFR molecules that have been tethered together by a linker (e.g., a 13, 7, 3, 1 amino acid peptide linker; $wtDHFR^2$) are capable of spontaneously oligomerizing, in the presence of $MTX^2$, to form highly stable ($t_{1/2}$>1 month) cyclic dimers, trimers, tetramers and octamers with diameters ranging from 8 to 30 nm. The ability to prepare supramolecular protein nanorings provides a unique ability for the self-assembly of tethered therapeutic proteins, such as antibodies.

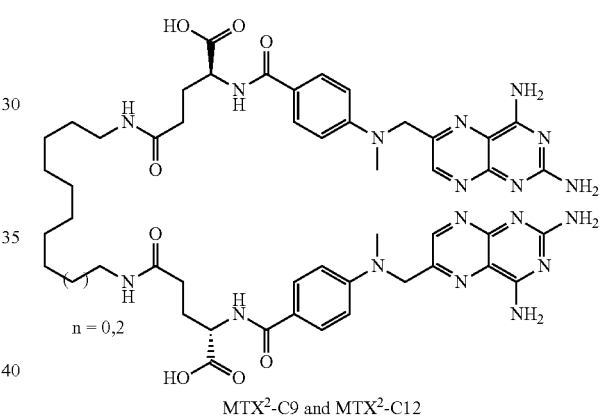

$MTX^2$-C9 and $MTX^2$-C12

Monoclonal antibodies and recombinant antibodies have been used to deliver a variety of toxins, drugs and radionuclide to cancer tissues. Recently, the targeting of drugs to tumors by conjugation to intracellularly cleavage linkers has been a successful antitumor approach. For example, the FDA approved antibody drug conjugate, Mylotarg, is composed of an antibody to CD33 that has been conjugated to the potent DNA alkylation compound, calicheamicin through an acid-labile hydrozone. Several other drugs, such as doxorubicin and auristatin have been coupled to antibodies and shown potential efficacy as anticancer drug. Despite their success in animal tumor models, antibody drug conjugates suffer from a number of limitations, such as, inadequate potency, reliance on monoclonal antibodies, inability to utilize higher avidity antibodies, and molecular heterogeneity.

To meet this need, an antibody and nanoring drug delivery system will be produced that allows interactions between cell cycle regulation, cell cycle specific chemotherapy, and a pro-apoptotic antibody. Data has shown that a chimeric single chain antibody (scFv-Fc) directed against the type I IGF receptor (IGF1R) first acts as an agonist and mitogen before downregulating receptor expression. A novel nanoring composed of this antibody and a linkage system using the cancer chemotherapeutic agent methotrexate will be produced. By coupling the anti-IGF1R antibody directly with the chemotherapeutic agent, the difficulty with complex scheduling and delivery of two or three different agents will be avoided. Also, the unique agonist property of this antibody to stimulate entry into the cell cycle followed by delivery of a cell cycle specific agent will be utilized IGF1R as a Target in Cancer Therapy Given the central role of IGF1R in cancer cell proliferation, survival, and metastasis, there has been a remarkable interest in targeting this pathway for cancer therapy. While there are potentially many ways to disrupt this receptor, a number of monoclonal antibodies have been described. Interestingly, the initial results show synergy between anti-IGF1R antibodies and cancer chemotherapy. Anti-tumor effects may be enhanced by appropriate sequencing. It is notable that inhibition of tumor growth by antibodies is due to induction of apoptosis.

scFv-Fc differs from all of the previously described antibodies in its initial agonist properties. (Sachdev et al., 2003) After binding the receptor, this antibody acts as a biochemical agonist and stimulates tumor cell growth in a fashion to similar to the receptor's cognate ligand IGF-I. However, over time the antibody down-regulates receptor expression by targeting IGF to the lysosome. In fact, this IGF down-regulation is induced by all of the monoclonal antibodies we have examined. Thus, this antibody is unique. It has the ability to stimulate cellular entry into S-phase, yet down-regulates the signaling pathway usually activated by IGF1R. This down-regulation of IGF1R disrupts an important cell survival pathway and may lower the threshold to induce apoptosis. These properties of scFv-Fc will be exploited by creating a self-assembling nanoring that includes scFv-Fc, E. coli dihydrofolate reductase, and methotrexate.

This nanoring should specifically deliver methotrexate and the anti-tubulin drug, auristatin to IGF1R expressing cells. Moreover, the agonist properties of the antibody should actually enhance methotrexate and auristatin cell mediated cytotoxicity. The subsequent down-regulation of IGF1R should enhance the pro-apoptotic effects on the cell.

A single chain chimeric antibody (scFv-Fc) directed against IGF disrupts IGF signaling by down-regulating IGF expression over time. Anti-IGF1R antibodies down-regulate cell surface receptor expression by targeting IGF1R to lysosomal degradation. Unlike other anti-IGF1R antibodies under development, scFv-Fc initially acts as an agonist of the receptor. Thus, scFv-Fc initiates an initial wave of mitogenesis, before ultimately down-regulating the receptor. While this could be viewed as a disadvantage, the agonist activity of scFv-Fc can be exploited in combination with cell cycle specific chemotherapy. Specifically, a nanoparticle drug will be produced to deliver scFv-Fc in combination with the antimetabolite methotrexate and the inhibitor of tubulin polymerization, auristatin. Since the efficacy of both drugs in cell-cycle dependent, the initial agonism of scFv-Fc to enhance breast cancer cell sensitivity to chemotherapy will be exploited.

Thus, as described herein, the following experiments will be performed: produce MTX-MTX(MTX$^2$) conjugates of; a) the fluorophore, Alexa Fluor 488 and b) the drugs, Doxorubicin and Auristatin; design, assemble and functionally characterize anti-CD19 and anti-CD22 DHFR-DHFR (DHFR$^2$) based polyvalent nanorings; and design and characterize a set of DHFR$^2$-MTX$^2$ heterodimer building blocks for co-polymer nanoring assembly by inserting ionic pair forming amino acids at the protein-protein interface.

Humanized anti-tumor anti-CD19 and anti-CD22 DHFR$^2$-scFv doxorubicin and auristatin Nanorings was also be produced, bispecific anti-tumor anti-CD19 and anti-CD22 scFv-DHFR nanorings will be constructed, and their in vitro and antitumor activity will be determined. Application of this approach to the design of antibody nanorings is useful, e.g., for detection of cancers, such as T-cell leukemia, lung cancer and breast cancer.

Thus, certain embodiments of the invention relate to self-assembling nanostructures that; 1) can be used for imaging and therapy, 2) can be disassembled by a small molecule drug, and/or 3) are effective against drug resistant and non-responsive neoplasms. Certain embodiments of the invention relate to radiotherapeutic nanorings that can be used as therapeutic agents, e.g., anticancer agents, as well as multifunctional tumor biosensors. A key feature of this approach is the ability to pharmacologically control the assembly and disassembly of the nanostructures. Certain embodiments of the invention relate to self-assembling heteromeric protein dimmers and the preparation of self-assembling copolymeric nanorings that are multivalent and multispecific.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers.

The terms "nucleic acid," "nucleic acid molecule," or "polynucleotide" are used interchangeably and may also be used interchangeably with gene, cDNA, DNA and RNA encoded by a gene.

Certain embodiments of the invention encompass isolated or substantially purified compositions, e.g., nucleic acid compositions. In the context of the present invention, an "isolated" or "purified" molecule is a molecule that exists apart from its native environment and is therefore not a product of nature. An isolated molecule may exist in a purified form or may exist in a non-native environment such as, for example, a transgenic host cell. For example, an "isolated" or "purified" molecule, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The term "gene" is used broadly to refer to any segment of nucleic acid associated with a biological function. Thus, genes include coding sequences and/or the regulatory sequences required for their expression. For example, "gene" refers to a nucleic acid fragment that expresses mRNA, functional RNA, or specific protein, including regulatory sequences. "Genes" also include nonexpressed DNA segments that, for example, form recognition sequences for other proteins. "Genes" can be obtained from a variety of sources, including cloning from a source of interest or synthesizing from known or predicted sequence information, and may include sequences designed to have desired parameters.

"Naturally occurring" is used to describe a composition that can be found in nature as distinct from being artificially produced. For example, a nucleotide sequence present in an organism, which can be isolated from a source in nature and which has not been intentionally modified by a person in the laboratory, is naturally occurring.

A "vector" includes viral vectors, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

An "expression cassette" as used herein means a nucleic acid sequence capable of directing expression of a particular nucleotide sequence in an appropriate host cell, which may include a promoter operably linked to the nucleotide sequence of interest that may be operably linked to termination signals. It also may include sequences required for proper translation of the nucleotide sequence. The coding region usually codes for a protein of interest but may also code for a functional RNA of interest, for example an antisense RNA, a nontranslated RNA in the sense or antisense direction, or a siRNA. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions. The expression cassette may additionally contain selectable marker genes.

"Functional RNA" refers to sense RNA, antisense RNA, ribozyme RNA, siRNA, or other RNA that may not be translated but yet has an effect on at least one cellular process.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Regulatory sequences" and "suitable regulatory sequences" each refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted above, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters. Examples of promoters that may be used in the present invention include CMV, RSV, polII and polIII promoters.

A "5' non-coding sequence" refers to a nucleotide sequence located 5' (upstream) to the coding sequence. It is present in the fully processed mRNA upstream of the initiation codon and may affect processing of the primary transcript to mRNA, mRNA stability or translation efficiency.

A "3' non-coding sequence" refers to nucleotide sequences located 3' (downstream) to a coding sequence and may include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

A "promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions.

"Constitutive expression" refers to expression using a constitutive promoter. "Conditional" and "regulated expression" refer to expression controlled by a regulated promoter.

"Operably-linked" refers to the association of nucleic acid sequences on a single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. In addition, expression refers to the transcription and stable accumulation of sense (mRNA) or functional RNA. Expression may also refer to the production of protein.

The term "altered level of expression" refers to the level of expression in transgenic cells or organisms that differs from that of normal or untransformed cells or organisms.

"Antisense inhibition" refers to the production of antisense RNA transcripts capable of suppressing the expression of protein from an endogenous gene or a transgene.

The following terms are used to describe the sequence relationships between two or more sequences: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, JMB, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)), are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, JMB, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, the invention also provides nucleic acid molecules and peptides that are substantially identical to the nucleic acid molecules and peptides presented herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

The structures of the linkers are not critical provided that the linkers do not interfere with the ability of the compound to function in its intended capacity. The linkers may be attached to the molecules at any synthetically feasible position provided that the linkers do not interfere with the ability of the compound to function in its intended capacity. For example, the linkers, and the attachment thereof, should allow for the formation of nanorings. In some embodiments, HINT is used as a linker.

The detectable groups may be, for example, a radionuclide or a fluorophore.

Thus, certain embodiments of the invention are directed to therapeutic and diagnostic utilities (e.g., anticancer and antiviral); the delivery of molecules such as drug molecules; the assembly of enzymes useful as chemical reactors and diagnostic agents; and the fabrication of electronic materials, e.g., in defined polyhedron-based nanostructures.

The invention will now be illustrated by the following non-limiting Examples.

EXAMPLE 1

Chemically Controlled Self-Assembly of Protein Nanorings

Figure 2:
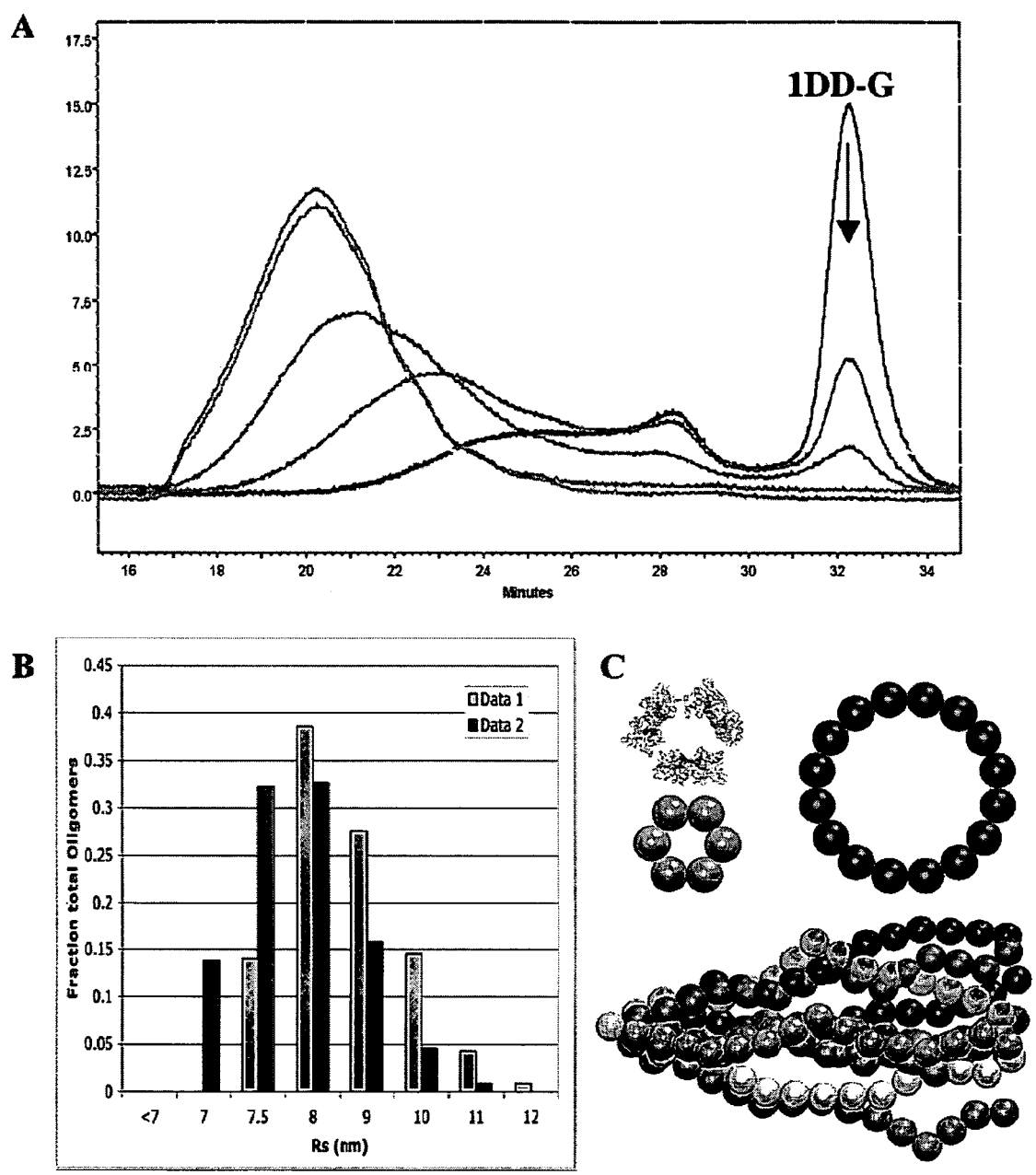
FIG. 2. Assembly of 1DD-G and MTX2-C9. (A) Gel filtration profiles for 1DDG with 0.25, 0.5, 0.75, 1.0, and 1.25 equiv of added MTX2-C9 overlaid. Data were collected in sequential runs, beginning with the 1.25× sample, 30 min after initial mixing. The disappearance of the monomer peak near 32 min as the concentration of dimerizer increases is indicated by an arrow. (B) Nonnegative least-squares fit DLS data for the 1DD-G:C9 mixture at 12 µM in P500 buffer. The calculated best-fit distributions of particle sizes for two independent data acquisitions on the same sample are plotted. The weighted averages of these two distributions yield an average particle size for the mixture, Rs) 8.3 nm. (C) Toroidal conformations for potential aggregates, with coordinates derived from regular polygon geometry, with overlay of 10 random conformations for the octameric linear chain evaluated in HYDRO.

To characterize the assembly of DHFR2-bisMTX oligomers, mixtures of 10 µM 1DD-G, the shortest and simplest of the DHFR2 fusion proteins, and MTX2-C9, a 9-methylene linked bisMTX dimerizer, were analyzed by gel filtration chromatography on a Superdex G200 column (GE Biosciences). As the relative ratio of MTX2-C9 was increased from 0.25 to 1.0 equiv, the peak corresponding to monomeric 1DD-G completely disappeared, with concurrent formation of a range of larger species (FIG. 2A). At stoichiometries approaching or exceeding 1.0 equiv of MTX2-C9 (also abbreviated C9), the smaller aggregates also disappeared, and assemblies of 1DD-G and MTX2-C9 were observed to elute in a broad peak centered at 20 min. This peak elution time corresponded to a calibrated Stokes radius (Rs) of 8.3 nm, substantially increased from the value of 3 nm observed for the monomer. The 1DD-G:C9 aggregates were remarkably stable. Kept in amber vials at room temperature, samples of assembled 1DD-G repeatedly analyzed by gel filtration over the course of 1 month showed no change in the observed size distribution. The 1DD-G:C9 aggregates also survived extreme dilution, remaining intact in transit through the gel filtration column at 50 nM total-protein concentration (the limit of detection in the gel filtration assay).

Following the formation of apparently robust assemblies, a theoretically rigorous characterization was pursued. The thermodynamics governing this mode of self-assembly have been investigated in the discipline of polymer chemistry, with particular attention given to ring-chain equilibria, and in immunology, where the assembly of antibody-antigen complexes has been considered in detail. In polymerization systems with suitable end-to-end connectivity, the growing polymer chain has the option to react with an uncoupled partner in solution and extend linearly, or with its own tail, terminating chain growth and forming a ring. The seminal work of Jacobsen and Stockmayer in the 1950s revealed that until the system reaches a critical concentration, only rings will be formed. At low monomer concentrations, ring formation is highly favored, because the intramolecular effective molarity is much higher than the solution concentration. Synthetic chemists have demonstrated these effects in small-molecule systems that rely on metal ion coordination or hydrogen bonding. Ercolani and co-workers have produced the most detailed theoretical description of ring formation, modeling the process in terms of the effective molarity (EMn) for each of the cyclic species and the association constant for connection of the subunits. Their model quantitates the significant degree to which ring formation is enhanced at low concentration and demonstrates that the propensity for ring formation increases in parallel with the association constant for the intermolecular connection. The extremely high affinity of DHFR-MTX binding, in tandem with micromolar protein concentrations, thus provides a strong driving force for ring formation. Ring size, in turn, is typically limited by entropic effects that strongly favor smaller oligomers. Introduction of conformational bias into the system can increase the EM of an individual oligomer, such as would be desired for the engineering of homogeneous self-assembled structures. Collectively, this theoretical framework strongly implies a cyclic conformation for the observed 1DD-G:C9 aggregates.

Static and dynamic light-scattering experiments were therefore carried out to evaluate the mass, dimensions, and solution geometry of these nanoparticles. The utility of light scattering in characterizing particle shape is well known, as the critical hydrodynamic parameters of Stokes radius and radius of gyration (Rg) provide two unique variables to robustly distinguish between oligomers of alternate shape. The ratio of the two parameters (Rg/Rs) yields a consistent descriptor of particle shape that is independent of absolute size: linear objects will have the highest Rg/Rs ratio and solid spherical ones the lowest, with other conformations falling at known discrete points on the spectrum between.

molecular weight of 240±12 kD, with a radius of gyration of 10.8±1 nm. This led to two conclusions: first, the molecular weight, 6.7-fold greater than that of 1DD-G, implied an average assembly containing seven 1DD-G subunits. Second, the SLS data indicate that the 1DD-G:C9 assemblies must adopt a shape with an average Rg/Rs ratio of 1.3±0.1.

To interpret these shape parameters, the program HYDRO was used to calculate the hydrodynamic properties for models of linear and toroidal 1DD-G:C9 assemblies. Toroidal structures with 3-9 subunits were generated, with the protein complexes approximated as rigid arrays of solid spheres (FIG. 2C).27 The calculated Rg/Rs ratios from HYDRO range from 1.17 to 1.29 for hexameric-nonameric toroids (Table 1A), in excellent general agreement with the experimental value of 1.27 derived from the light-scattering data. To contrast the cyclic and linear geometries, the octamer was chosen as a test case for further HYDRO calculations, and a set of 20 linear chains in random conformations was generated (FIG. 2C). Parameters governing the flexibility of the chain were derived from Charmm simulations of the DHFR dimer and 1DDG conformational variability. The calculated hydrodynamic data are summarized in Table 1B. While the mean Rs value for the linear conformer is very similar to that of a toroid, the linear chain Rg value is significantly higher (16.5 vs. 11.2 nm), yielding an Rg/Rs ratio of 1.75±0.04, significantly different from the experimental value of 1.3±0.1. Taken together, the calculated Rg/Rs ratios and experimental data strongly support a toroidal conformation for the 1DD-G:C9 nanostructures.

TABLE 1

HYDRO Modeling Data for Toroidal and Linear Assemblies
(A) Calculated Hydrodynamic Dimensions of Circular DHFR-C9 Toroids Ranging in
Size from n = 3 to n = 9 and (B) Calculated Properties of the Linear Octamer Compared
to the Calculated Octameric and Heptameric Toroids, and to the Experimental Data[a]

| (A) Hydrodynamic Dimensions of DHRR-C9 Toroids | | | | | |
|---|---|---|---|---|---|
| n | Rs | Rg | Rg/Rs | longest axis (nm) | Rs exp(GelF) |
| 9 | 9.72 | 12.49 | 1.28 | 29.1 | |
| 8 | 8.9 | 11.15 | 1.25 | 26.34 | 8.25 |
| 7 | 8.06 | 9.8 | 1.22 | 23.6 | 7.26 |
| 6 | 7.215 | 8.47 | 1.17 | 20.9 | 6.74 |
| 5 | 6.35 | 7.15 | 1.13 | 18.22 | 6.08 |
| 4 | 5.47 | 5.86 | 1.07 | 15.5 | 5.32 |
| 3 | 4.58 | 4.61 | 1.01 | 12.9 | 4.63 |

| (B) Properties of Linear Octamer and Octameric and Heptameric Toroids | | | |
|---|---|---|---|
| conformation | Rs | Rg | Rg/Rs ratio |
| linear octamer | 9.45 ± 0.1 | 16.5 ± 0.5 | 1.75 ± 0.04 |
| toroidal heptamer | 8.1 | 9.8 | 1.22 |
| toroidal octamer | 8.9 | 11.15 | 1.25 |
| experimental | 8.3 ± 0.3 | 10.8 ± 1 | 1.3 ± 0.1 |

[a]The Rg/Rs ratio strongly supports a toroidal conformation.

Figure 3:
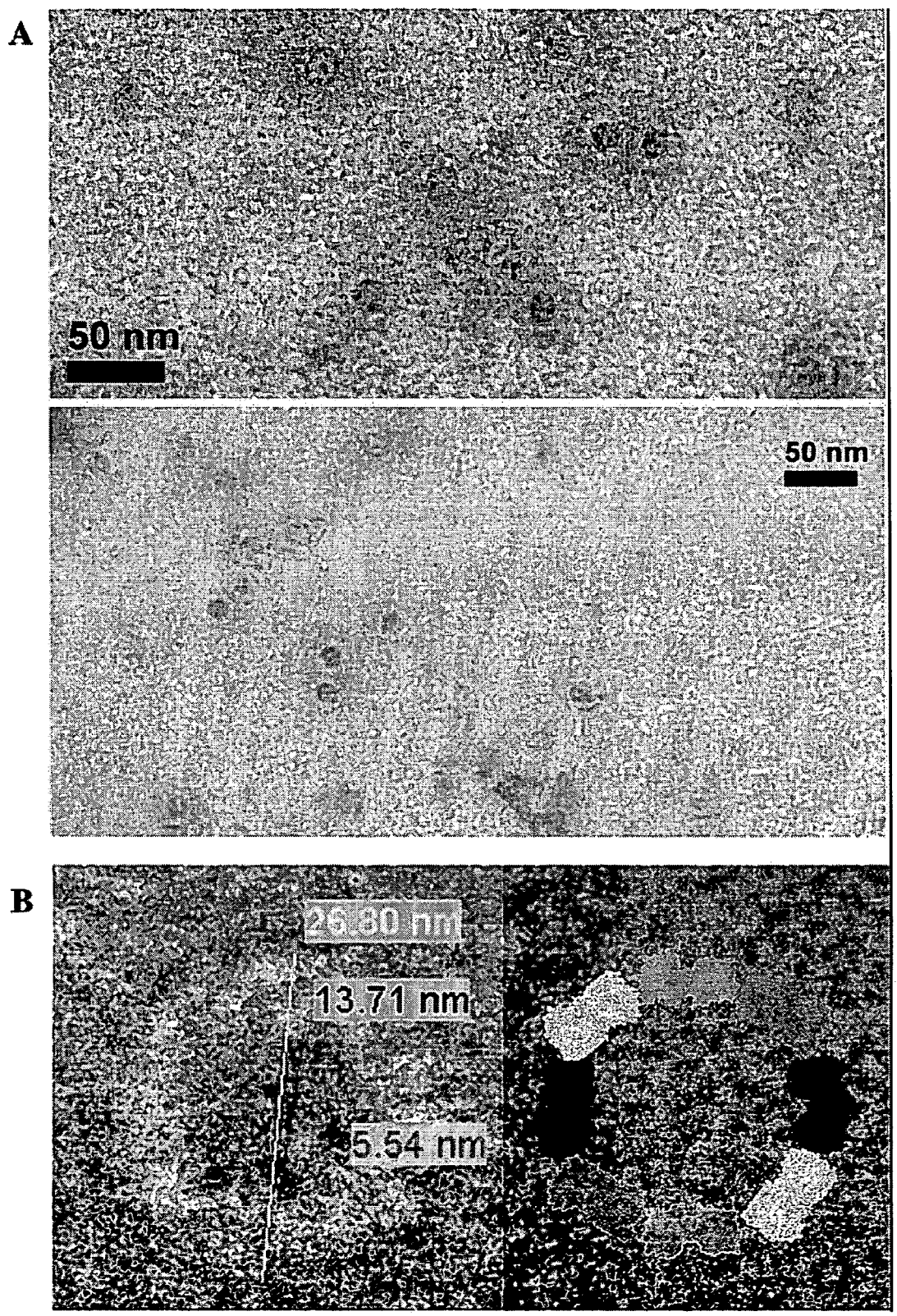
FIG. 3. TEM imaging of 1DD-G:C9. Uranyl acetate stained images of 1DD-G:C9 deposited on a carbon grid. (A) Representative fields at 20 000× magnification illustrate consistent size and appearance of nanorings. 50 nm scale bars indicate scaling of the images. (B) At left, a single nanoring viewed at 63 000× magnification; the dimensions of the toroid are indicated. On the right, a space-filling model of an octameric ring is scaled to match the size of the TEM image, illustrating the matching proportionality of the ring shape.

Dynamic light-scattering (DLS) data were collected at 90° to assess the Stokes radius of the 1DD-G:C9 assemblies at their peak size (1 equiv of added C9). For 12 μM 1DD-G:C9, the DLS results indicated a distribution of hydrodynamic diameters from 14 to 22 nm, corresponding to an average Stokes radius of 8.3 nm (range: 7.98-8.66 nm), consistent with radii derived from the calibrated gel filtration data (FIG. 2B). For static light-scattering (SLS) experiments, six samples were prepared, extending from 5 to 40 μM (0.17-1.41 mg/mL) total protein concentration. The scattering intensities were measured at regular intervals from 30° to 130°, and analyzed by the Zimm plot method, yielding an average The circular nature of these complexes was directly confirmed when the 1DD-G:C9 assemblies were examined by negatively stained TEM (FIG. 3). The structures observed were remarkably homogeneous, with no apparent linear fragments, fractured, or displaced toroids present; approximately 80% of the rings were geometrically circular, with minimal ellipticity seen in the remaining 20% (FIG. 3A). The visibility of the toroids was enhanced by apparent pooling of the uranyl acetate contrast reagent in the center of the rings. At extreme magnification, the close correspondence of the nanoring proportions to those expected for a DHFR-derived toroid is evident (FIG. 3B). These results provide another striking demonstration of the stability of the 1DD-G:C9 nanorings, which remain intact through the staining and imaging process (2% uranyl acetate stain, pH 4) and subsequent air-drying.

Figure 4:
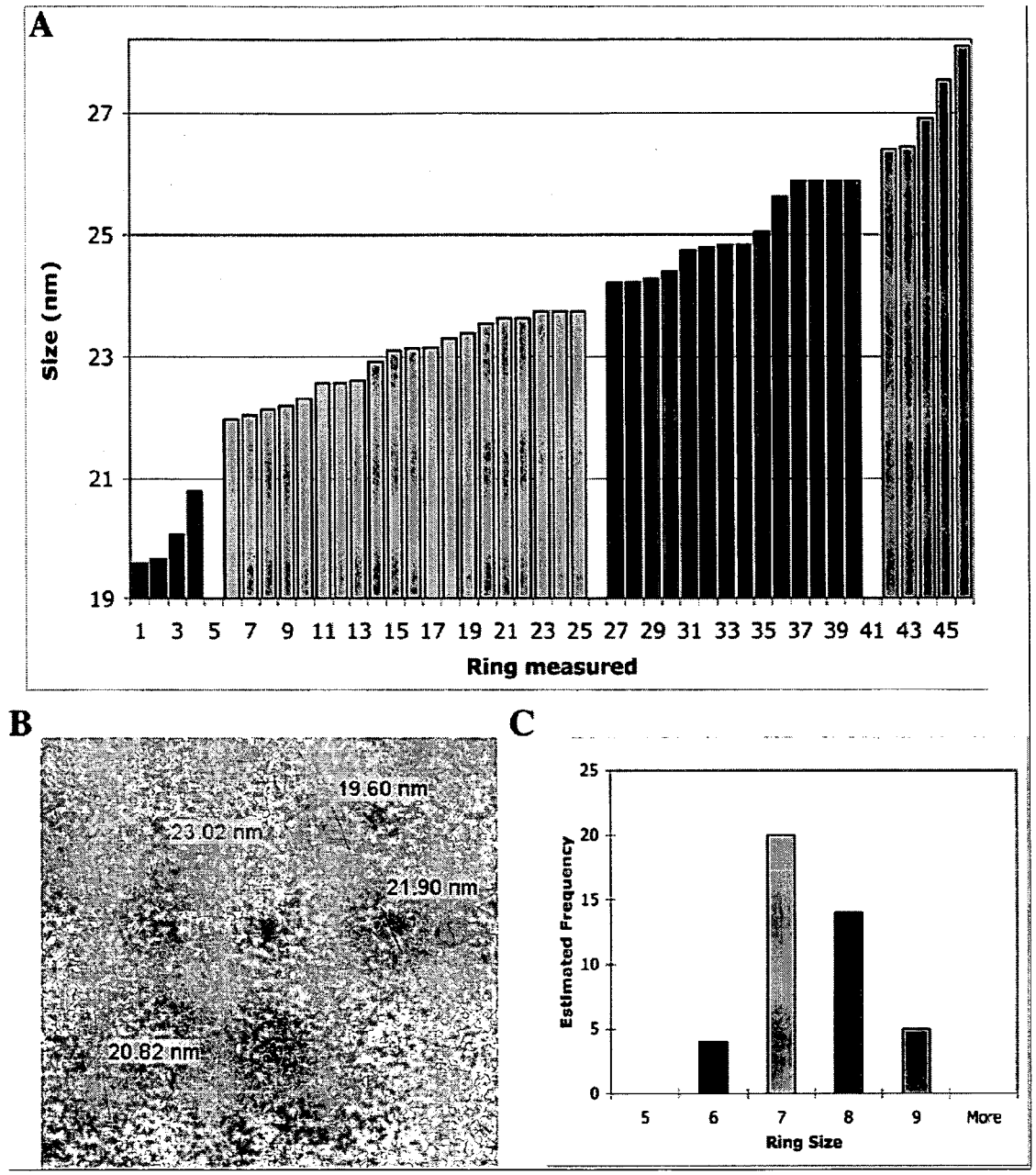
FIG. 4. Distribution of 1DD-G:C9 nanoring dimensions. (A) The diameters of 43 1DD-G:C9 nanorings, measured from three TEM wide fields at 20 000× magnification, are graphed. The coloration corresponds to approximate oligomer size ranges derived from the HYDRO calculations; the "longest axis" measurement calculated for each toroid is used as an upper limit for that oligomer size. (B) The dimensions of four nanorings are measured in this image field, illustrating the method. (C) Histogram of ring sizes, based on the estimated size cutoffs applied to the data in part (A).

Analysis of several wide-field images reveals that the observed toroids range from 20 to 28 nm in outer diameter (FIG. 4A). The measurement process is illustrated for a cluster of nanorings in FIG. 4B; in repeat trials, the error of the graphical sizing method was approximately 5%. By applying the HYDRO calculation of maximal toroid dimensions (Table 1) as a rough criterion, we sorted the distribution into four clusters, corresponding to oligomers of 6-9 subunits. The calculated longest axis was applied as the upper limit for each integer particle size; the resulting histogram of observed 1DDG: C9 oligomers appears in FIG. 4C. This distribution is appealingly consistent with the SLS data, which also suggested an average 7-subunit assembly.

Armed with this careful characterization, the structural analysis of the remaining DHFR2 variants (FIG. 1B) was determined, buttressed by the strong theoretical and mechanistic implication that these proteins will also form toroids. As the inter-DHFR linker is lengthened from a single amino acid to 3, 7, or 13 residues, the conformational flexibility of the DHFR2 dimer increases, and the effective molarity of smaller oligomers is expected to increase in parallel. In tandem, entropic forces will drive the formation of smaller toroids. Thus, the nanoring size-distribution may be tuned by adjusting the inter-domain linker length, a mechanism appealingly dependent not on intricate structural engineering but rather on fundamental biophysical chemistry.

Figure 5:
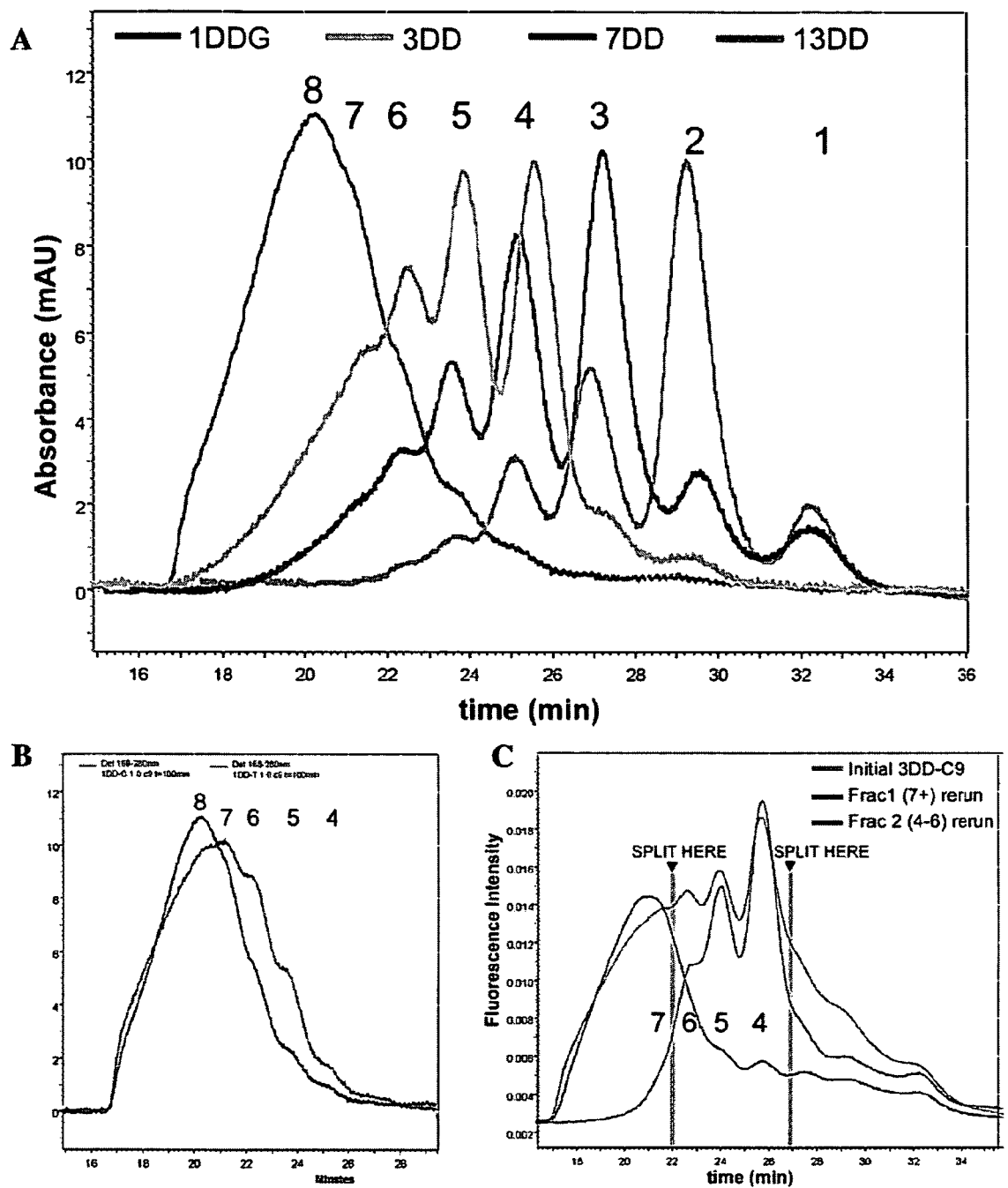
FIG. 5. Regulation of oligomer size as a function of linker. (A) In the top panel, the gel filtration traces for fully assembled (1:1) 1DD-G:C9, 3DD-C9, 7DD-C9, and 13DD-C9 are overlaid, illustrating the ability to assign each peak to a discrete nanoring size, from dimer to octamer. (B) The overlaid traces for 1DD-G:C9 and 1DDT-C9 illustrate the ability of a single amino acid substitution to tune the observed oligomer pattern. (C) The Superdex G200 elution profile of 40 μM 3DD-C9 (1:1). The material from the start of the peak until the first split point was collected in one fraction, representing oligomers of n≧7. The complexes that eluted between the first and second split points (n=4-6) were collected into a second fraction. When each of the collected fractions was reinjected onto the column, the segregated oligomer sizes remained stable.

Full assembly profiles for each of the DHFR2 variants with MTX2-C9 was collected, and it was found that the observed nanoring size was indeed dependent on the length of the inter-DHFR linker. In FIG. 5A, the elution profiles for MTX2-C9-assembled 13DD, 7DD, 3DD, and 1DDG are overlaid. Starting with the monomer peak at 32.4 min, which is constant for all five proteins, a landscape of discrete peaks marches leftward, enabling enumeration of each oligomer, indicated in FIG. 5A by superimposed integer assignments for each peak. Unlike the elution profile for 1DD-G:C9, the oligomer distributions for 13DD:C9, 7DD:C9, and 3DD:C9 are well resolved, a consequence of the selectivity curve of the Superdex G200 matrix, which has much higher resolving power at Stokes radii of 2-6 nm. SLS and DLS data collected for the 3DD:C9 and 13DD:C9 aggregates were consistent with the toroidal geometry implied by 1DD-G:C9 data and HYDRO modeling.

Whereas the longer 13DD forms principally dimers, with progressively smaller quantities of trimer, tetramer, and pentamer, the 7DD dimer forms a spectrum of toroids spanning dimers to heptamers. In contrast, when the linker is shortened to 3 amino acids, virtually all of the assemblies are tetrameric or larger, with a preponderance of tetrameric nanorings. In FIG. 5B, the gel filtration profiles of 1DDG and 1DDT are compared. The role of a single amino acid change in tuning the obtained distribution of rings is apparent. The 1DDG peak spans oligomers from n=6 to n>9 (with sizes greater than 8 unresolved) and includes just traces of pentameric and tetrameric aggregates. In contrast, although the distribution of larger-sized oligomers at the left edge of the peak is quite similar, 1DDT forms a significantly increased amount of hexameric and pentameric rings.

Figure 6:
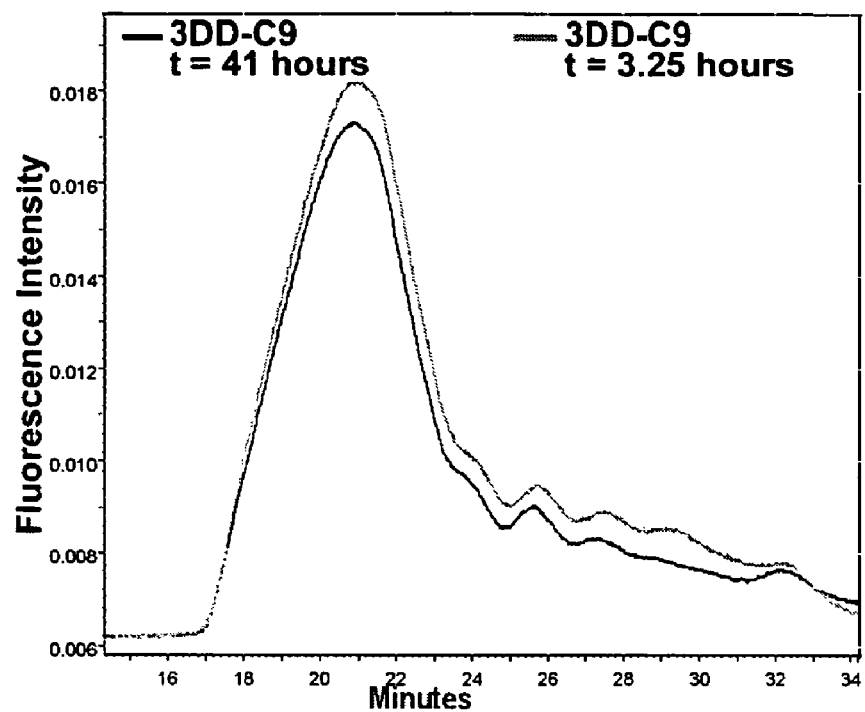
FIG. 6. Stability of isolated 3DD-C9 oligomer fractions. (A) The composition of the n≧7 fraction remains essentially unchanged after 41 hrs at 4° C. (B) With only a slight increase in the amount of tetramer, the n=4-6 fraction is also very stable under these conditions.
Figure 6:
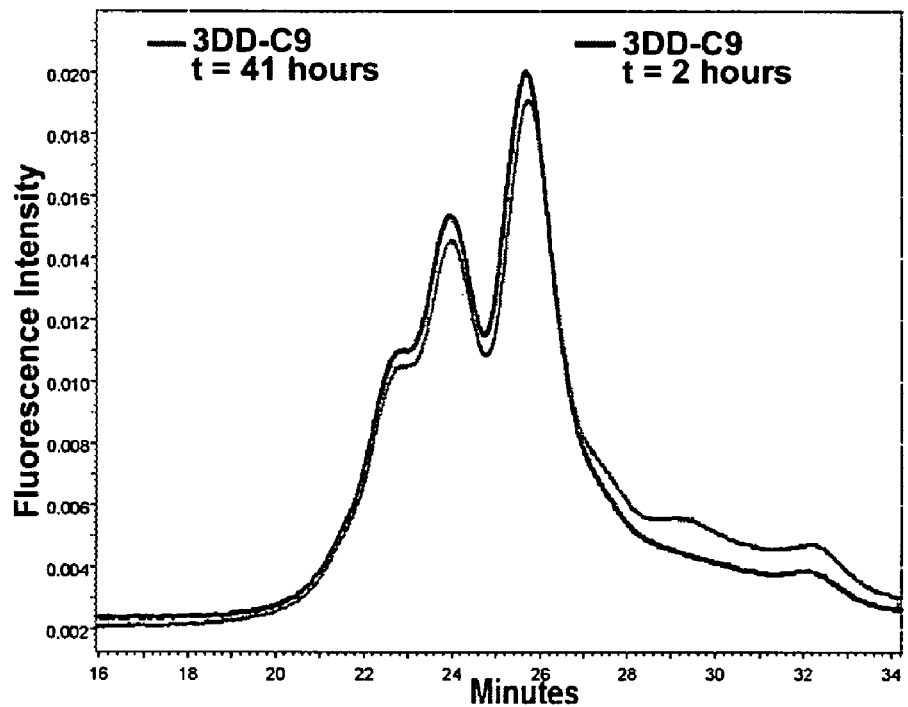
Figure 7:
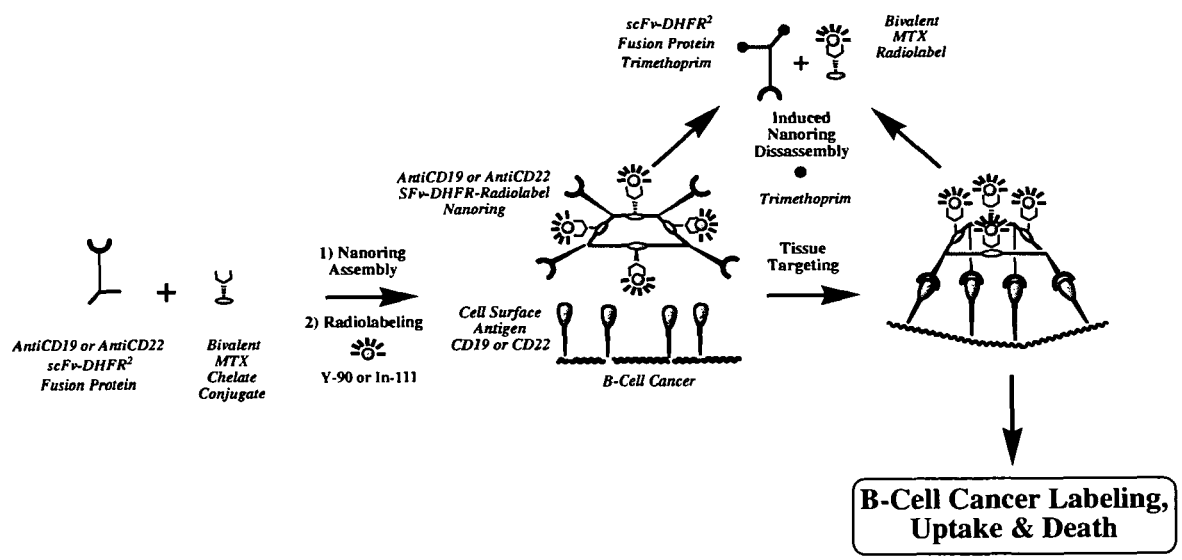
FIG. 7. Anti-Cancer Drug Delivery by Self-Assembling Polyvalent Antibodies.
Figure 8:
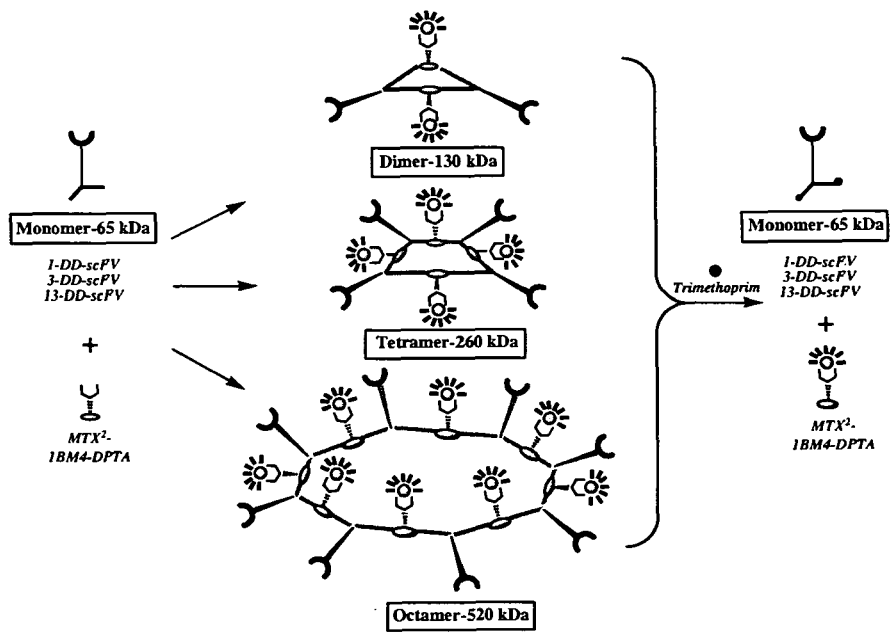
FIG. 8. DHFR2 scFV Assembly and Dissassembly.

To investigate the dynamic equilibrium of the observed oligomer distributions, gel filtration was used to purify a discrete subpopulation of nanorings. 3DD was tested because of the excellent resolution of the tetramerhexamer peaks. FIG. 5C illustrates the results of these fractionation stability experiments. A fully assembled 3DDC9 mixture was injected onto the G200 column, and the eluted material was collected in two fractions, one containing heptameric and larger assemblies, the other tetramers-hexamers. Reanalysis of these separate fractions via gel filtration revealed that the segregated oligomer populations retained their original sizes; the individual nanorings were stable to purification. Further testing demonstrated that both purified nanoring fractions remained stable in dilute solution at 4° C. for days (FIG. 6).

These experiments demonstrate the creation of exceptionally stable proteinaceous nanorings, resistant to both adverse environmental conditions and high dilution. The dimensions of these rings can be tuned by changing the length of the intramolecular protein linker, and individual size ranges of oligomers can be purified. When the rules for the design of ligand-induced dimerization systems (Carlson et al., 2003) are combined with recent theoretical models of supramolecular assembly, (Ercolani, 1998 and 2003) these results establish the underlying principles required for the design of stable self-assembling protein-based nanoarchitectures. Appealingly, the intrinsic conformational flexibility of the DHFR2 building block allows equilibrium and kinetic factors to dictate nanoring geometry, resulting in structures such as the stable tetramer observed for 3DD:C9. Consistent with the theoretical framework outlined by Ercolani, the size distribution of the assembled toroids depends on the balance between entropy and conformational dynamics. The entropic factors that favor the smallest feasible oligomer are offset by the ring strain imposed by the intrinsic stiffness of the DHFR2 building blocks, which dictates the EM of the individual toroids. As the design of fusion proteins with controlled intramolecular orientations remains difficult, this robust biophysical mechanism is a valuable tool.

Ultimately, the properties of the dimerizing ligand are also important in regulating the energetics and geometry of self-assembly. The ability of the bisMTX dimerizers to adopt a folded conformation in solution should promote stable assemblies by the same mechanisms operative for simple dimerization. In parallel with the effects of protein engineering, modifications in the dimerizer linker length will also alter the geometric characteristics regulating DHFR2 nanoring formation, thus providing a route to synthetic bio-polymeric materials, in addition to discrete oligomers. A proteinaceous or hybrid protein-organic polymer with noncovalent bisMTX linkages represents a pharmaceutically reversible material. In the presence of excess concentrations of an appropriate competitive drug molecule, the connections stitching the polymer together could be specifically dissolved, particularly once an initial competitive binding event has reduced the macrocyclic oligomers to linear species. This drug-responsive material will be useful for many biomedical applications.

The set of DHFR2 constructs is well suited for development of more elaborate self-assembling architectures. The N and C termini of the proteins, as discussed previously, are 180° removed from the dimer interface, permitting ready construction of trimeric and tetrameric fusion proteins. In this manner, assembly of DHFR2 nanorings may create circular clusters of other structural or functional proteins, such as artificial antibodies or templates for nano-molecular gears. In addition, the ability to prepare protein polygons provides a means for the preparation of self-assembling protein polyhedra.

Materials and Methods

Protein Expression and Purification. The procedure for construction of the DHFR2 plasmids is described in detail herein. JM-105 *E. coli* containing the engineered DHFR2 plasmid of interest were cultured in LB or TB broth containing ampicillin (100 ug/mL). Cultures were grown at 37° C. in 2 L flasks with stirring and aeration to an $OD_{600}$ of 0.6-0.8, whereupon IPTG was added to a concentration of 0.35 mM. The cultures were returned to the shaker and incubated for another 4-6 h, at which point the $OD_{600}$ was typically >1.5. Cells were harvested through centrifugation at 7500 g for 30 min at 4 C. Typically, 3-4 g of cell paste was obtained per liter of LB culture, and 5-6 g per liter of TB culture.

The cell paste (approximately 7 g) was suspended in 6-7 mL of lysis buffer plus lysozyme (10 mM $KH_2PO_4$, 0.1 mM EDTA, 1 mM DTT, pH 8, 1 mg/mL lysozyme) and incubated at room temperature with gentle shaking for 30 min. The partially lysed cells were then cooled in an ice bath and sonicated 12×30 s, with ≧2 min between each repetition to allow the lysate to cool to 4-6° C. The slurry was centrifuged at 40 000 g for 45 min at 4° C. The supernatant was decanted and saved. Unlike the methods described for purification of monomeric DHFR, a second round of sonication was not performed; this maximized the protein concentration, important for the MTX-column loading step. Finely ground ammonium sulfate was added with vigorous magnetic stirring to the combined supernatants to reach 30% saturation over 75 min at 4° C. The slurry was centrifuged at 40 000 g for 25 min at 4° C. The supernatant was dialyzed for 2 or more hours in 2 L of equilibration buffer (10 mM KH2PO4, 0.1 mM EDTA, 0.5 M KCl, 1 mM DTT, pH 6).

In the optimized method, the dialyzed protein solution was loaded (2 mL/min) at full concentration onto a methotrexate column that had been prepared with phosphate buffer (50 mM KH2PO4, 1 mM EDTA, 1 mM DTT, pH 6). Once the retentate was fully loaded, the column was washed with high salt buffer (50 mM KH2PO4, 1 mM EDTA, 1 mM DTT, 1 M KCl, pH 6) until A260 and A280 of the flow-through were less than 0.05. The partially purified protein was initially eluted with 200 mL of 1 mM folate buffer (10 mM KH2PO4, 0.1 mM EDTA, 1 M KCl, 1 mM folate, 1 mM DTT, pH 9) at 1 mL/min, collected in 8 mL fractions. The gradient program then increased the elution buffer to 15 mM folate over the next 100 min, and finished with a further 200 mL of 15 mM folate buffer. The eluted fractions were assayed for DHFR activity via the assay described below. The high-folate fractions with DHFR activity were held in reserve, and the low-folate fractions with activity were combined and dialyzed four times against 2 L of dialysis buffer (50 mM Tris, 1 M NaCl, 1 mM EDTA, 0.5 mM DTT, pH 8) for 4 h each to remove folate. One final dialysis against 2 L of DEAE column equilibration buffer (10 mM Tris, 1 mM EDTA, 1 mM DTT, pH 7.2) for 4 h in preparation for loading onto column was completed. The dialyzed retentate was then loaded onto a DEAE Cellulose column prepared with equilibration buffer (above) at 1.5 mL/min. The column was washed with 200 mL of the same equilibration buffer and then eluted in a 500-min linear gradient between equilibration buffer and DEAE elution buffer (10 mM Tris, 0.5 M KCl, 1 mM EDTA, 1 mM DTT, pH 7.2) with 8 mL fractions collected. Collected fractions were assayed for DHFR activity as previously described and analyzed for A280 and A260.31 Fractions containing pure DHFR2 were combined and concentrated with a Millipore Amicon Ultrafiltration YM-3 Membrane to approximately 2 mg/mL. The purity of the protein and progress of the purification was assayed with 12% SDS-PAGE (Invitrogen) and gel filtration chromatography (see below).

Gel Filtration. Gel filtration samples were prepared in P500 buffer (0.5 M NaCl, 50 mM KH2PO4, 1 mM EDTA, pH 7.0) with 5% (v/v) glycerol. Samples were mixed in 200 μL vial inserts (Chromtech, MN), with the components added in a specific order to ensure reproducibility: first buffer, then DHFR2, and then dimerizer. Samples were incubated at room temperature for a minimum of 20 min prior to analysis. The mixture was fractionated with a Superdex G200 size exclusion column (GE Biosciences), eluted with P500 buffer, and the relative peak sizes quantitated by absorbance at 280 nm. Samples were stored in amber vials and carefully shielded from direct light to avoid long-term MTX photodegradation. The Superdex G200 column was calibrated with a molecular weight standards kit (GE Biosciences). The test reagents were Blue Dextran (MW=$2\times10^6$), used to determine the void volume of the column, thyroglobulin (669 kDa), ferritin (440 kDa), catalase (232 kDa), aldolase (158 kDa), and bovine serum albumin (66 kD). To extend the calibration curve to the lower molecular weight range, DHFR2-3DD (36.2 kD), DHFR (18.0 kDa), and cytochrome C (12.4 kDa) were also included. The calibration curves were calculated as recommended by the manufacturer. The linear molecular weight calibration plotted Log MW versus Kav, where Kav) (VE–Vo)/(Vt–VE); VE is the elution volume of the MW standard; Vo is the void volume (elution volume of blue dextran); and Vt is the total column volume (24 mL). The R2 value for the line of best fit was 0.986. The Stokes radius calibration was determined by plotting (–log(Kav))0.5 versus Stokes radius, yielding a straight line with an R2 of 0.994.

Sample Preparation for Light Scattering. All samples for lightscattering experiments were prepared by methods designed to maximally reduce dust contamination. Water used for cleaning the sample tubes was triple-filtered through a 0.2 μm PES membrane (Corning). The acetone used for rinsing and drying the sample tubes was filtered through a 0.2 μm nylon filter membrane (Chromtech, MN), then triple filtered through a 0.02 μm aluminum oxide membrane (Anopore, Whatman, UK). Sample tubes (10×100 mm) and plastic caps were initially cleaned by 5 min of sonication in a water bath (Fisher Scientific). All subsequent sample preparation was conducted inside a laminar flow tissue-culture hood to reduce ambient dust burden. The clean sample tubes and caps were rinsed thoroughly with 0.2 μm-filtered water, rinsed a minimum of two times with 0.02 μm-filtered acetone, and left open inside the hood until the acetone evaporated, when they were recapped.

Stock solutions of DHFR2 proteins were equilibrated with P500 buffer at pH 7 via dialysis or by serial concentration/dilution in an Amicon concentrator (Millipore, MA). The concentration of the protein solution was then determined spectrophotometrically; an extinction coefficient of 62 200 M-1 cm-1, double the literature value for DHFR, was employed.31 This raw concentration was corrected for the optical purity of protein (the fraction of the total A280 accounted for by the protein), as determined by gel filtration chromatography. MTX2-C9 stock solutions were prepared in DMSO and assayed spectrophotometrically to determine their concentration. An extinction coefficient of 47 400 M-1 cm-1 in pH 13 NaOH, double the value observed for a MTX γ-amide, was employed. The stock concentration was calibrated so that the final samples contained less than 2% DMSO. The dimerizer solution was then diluted 1:2 or 1:3 into P500 buffer. The protein and dimerizer solutions, inside the tissue-culture hood, were each filtered three times with a 0.02 μm Anopore syringe filter (Whatman, UK).

Autoclaved micropipet tips, rinsed three times in 0.02 μm-filtered buffer immediately prior to use, were used in all subsequent sample preparations. Appropriate volumes of the DHFR2 and MTX2-C9 stocks to yield a 1:1 stoichiometric mixture were combined and thoroughly yet gently mixed in a rigorously cleaned screw-top vial with a Teflon lid liner.

This mixture was incubated at room temperature for 15-20 min, whereupon aliquots were withdrawn, added to the clean sample tubes, and diluted in varying ratios with ultrafiltered P500 buffer to yield the experimental samples.

Laser Light Scattering. Light-scattering studies employed a custom-built apparatus with a variable-power 488 nm argon ion laser light source (Lexel Laser, Inc., CA) and a goniometer-photodetector system (Brookhaven Instrument Corp., NY). Laser power, adjusted as necessary to sample the range of concentrations and particle sizes, ranged from 50 to 200 mW. For the dynamic light-scattering (DLS) experiments, the autocorrelated data were analyzed by both cumulant and non-negative least-squares (NNLS) regression analysis. For the static lightscattering experiments, data were collected across a range of angles from 30° to 130°:30°, 35°, 40°, 45°, 50°, 60°, 70°, 80°, 90°, 100°, 110°, 120°, and 130°. The instrument was calibrated with a toluene standard sample.

Hydrodynamic Calculations. For calculations made with HYDROPRO, a model of DHFR2-1DDG was constructed in InsightII (Accelrys, CA) by rearranging and linking (N-term-C-term) the two DHFR subunits from the 4DFR crystal structure. Calculations on monomeric DHFR used the B chain from the 4DFR dimer structure. HYDROPRO employs a two-stage bead-shell modeling process to calculate hydrodynamic properties of globular proteins on the basis of their atomic structure. In the first stage, a spherical bead of calibrated size replaces each heavy atom in a crystal structure. The space defined by these larger beads is used to create a hollow shell, composed of smaller spheres, that is successively refined to yield accurate hydrodynamic properties. The atomic element size was set to 3.1 Å for construction of the initial bead model; for the extrapolated shell-model calculation, a bead-diameter range of 2.05-1.05 Å and sampling interval of 0.2 Å were employed.

HYDROPRO calculations on DHFR aggregates used bead radii of 2.15 and 2.0 nm. The coordinates for the toroidal structures were initially calculated trigonometrically in Microsoft Excel by deriving the geometric spacing for the appropriate regular polygon. To test the effect of bead size on calculated toroid parameters, a Fortran program was written to automatically generate the appropriate coordinates and HYDRO input file for the n=3 to n=9 toroids. A second Fortran program was written to derive coordinates and produce HYDRO input files for the randomly sampled linear chains. This code applied a simple algorithm to three-dimensionally randomize the intramolecular bend angle of each element of the virtual DHFR2 chain. The randomization function was tuned to produce a range of outside bend angles from about 108° (matched to the vertex angle of a pentagon) to 180° (linear). The calculated Rs and Rg values of 20 structures generated by this means were tabulated for summary statistics. To verify the geometric accuracy of the computer-generated structures, the pseudo-PDB file generated by HYDRO was loaded into VMD for visual inspection.

Transmission Electron Microscopy. Samples of MTX2-C9 and 1DDG in P500 buffer were filtered by the methods described for the light-scattering experiments above, then mixed in 1:1 stoichiometry at 40 μM concentrations. These samples were stored on ice and shipped to Montana for microscopy. The 1DD-G:C9 oligomer solution was passed through a Superose 200 gel filtration column to reduce the salt concentration and the protein peak collected in one band. This material was concentrated by centrifugation and stored at 4° C. prior to TEM analysis.

The 1DD-G:C9 oligomer mix was deposited on 300-mesh copper grids that had been sequentially Formvar and carbon coated. The grids were blotted and stained with 2% uranyl acetate by standard techniques.

In screening and annotating the wide field 1DD-G:C9 TEM images, rare rings with more than 10% apparent ellipticity were excluded from the dimensional analysis. In cases where minor ellipticity was observed, the reported diameter is the average of the perpendicular long and short axes.

Work related to Example 1 was published as Carlson et al., 2006.

EXAMPLE 2

Dimerization Studies with MTX2-C9 and MTX2-C12

To elucidate the role of ligand conformation in induced protein dimerization, we synthesized flexible methotrexate (MTX) dimers, MTX$^2$-C9 and MTX$^2$-C12, and investigated their ability to selectively dimerize E. coli dihydrofolate reductase (DHFR). Typically, ecDHFR and mDHFR (5 μM) were incubated in P500 buffer (0.5M NaCl, 50 mM potassium phosphate, 1 mM EDTA, pH 7.0) with 5% (v/v) glycerol for a minimum of 3 hr with varying amounts of MTX$^2$-C9 or MTX$^2$-C12 in final stoichiometric ratios of dimerizer:protein ranging from 0.1:1 to 50:1. The mixture was then fractionated on a Sephadex G-75 size exclusion column eluting with P500 buffer, and the amount of monomeric and dimeric protein quantitated by absorbance at 280 nm. Dimerization was shown to have reached equilibrium, as incubations conducted for as long as 5 days gave identical results. In spite of known entropic barriers, both MTX dimers proved to possess substantial conformational stability in aqueous solution ($\Delta G_{fold} \geq -3.8$ kcal/mol), exerting a dominant influence on the thermodynamics of dimerization: in order to dimerize DHFR, each MTX dimer must shift from a folded to an extended conformation. From this conclusion, the strength of favorable protein-protein interactions in DHFR-MTX$^2$ dimers ($\Delta G \geq -3.1$ kcal/mol), and the selectivity of dimerization for E. coli DHFR relative to mouse DHFR ($>10^7$) could be determined. Consequently, the secondary structure of the minimal foldamers regulates their ability to dimerize dihydrofolate reductase in solution, providing insight into the complex energy landscape of induced dimerization.

EXAMPLE 3

X-Ray Crystallographic Studies with MTX$^2$-C9 and MTX$^2$-C12

To explore the molecular basis for the induction of DHFR dimerization, we have crystallized and carried out the structure determination of ecDHFR as a binary complex with MTX$^2$-C9 and MTX$^2$-C12. The diffraction data were collected at various temperatures for the ecDHFR complexes. Crystals were prepared in MnCl$_2$, PEG6K at ph 7.0. Data for the ecDHFR-MTX$^2$-C12 dimer at 2.4 Å resolution showed a dimeric structure with clear density for MTX but not the linker regions, and no density for the cofactor. These data also showed the binding of Ca at the dimer interface, as observed for the native structure previously reported. The crystals were difficult to freeze and thus only room temperature data was collected. Based on these results, new crystals of both the MTX$^2$-C12 and MTX$^2$-C9 complexes were grown in the presence of MnCl$_2$ and data collected to 1.8 Å resolution under cryogenic conditions on a RaxisIV area detector. Analysis of these data revealed the same dimer orientation with clear density for the MTX in each case, but again no evidence for the cofactor, NADPH, even though the sample was incubated in the presence of NADPH.

Again, in the case of the MTX²-C12 analogue, there was no clear indication of bridging linker density. However, in the case of the MTX²-C9 analogue there was an indication of linker electron density that did bridge across the dimer interface as expected from modeling studies. Additional results from another data set were unable to establish sufficient electron density for the linker. Thus, these results indicate a disordered model in which each ecDHFR monomer clearly bound one MTX, but no cofactor. Analysis of yet another data set did not reveal better electron density for the bridging linker. These data indicate a dynamic dimerization process and further indicate the design of a MTX² analogue with a less flexible linker could result in a better trace of the bridging density.

EXAMPLE 4

Dimerizer Synthesis

Two MTX molecules linked by a nine methylene (MTX²-C9) or twelve methylene (MTX²-C12) linker are efficient dimerizers of DHFR and are able to induce the self-assembly of DHFR-DHFR fusion proteins into protein nanorings. To expand the number and capability of available MTX² dimerizers, two new polyethylene glycol based dimerizers, MTX²-PEG5 and MTX²-PEG6 were constructed. (Scheme 1) It is now possible to evaluate (14 and 17 atoms) with enhanced water solubility. PEG5 or PEG4 were each tosylated with tosyl chloride in the presence of triethylamine in 95% yield. Conversion of the PEG tosylated to the corresponding diamine was accomplished by diazotization with sodium azide, followed by reduction of the alkyl azide product with triphenyl phosphine in an overall yield of 80%. Next, diprotected glutamate was coupled to the PEG diamine via the gamma carboxylate in 66% yield. Following removal of the Cbz groups by hydrogenation, coupling to 2,4-diamino-6-pteridylinyl N-methyl-aminobenzoic acid and saponification with barium hydroxide afforded MTX²-PEG5 and MTX²-PEG4 in a yield of 80-90%. Both dimerizers were shown to be considerably more water soluble than MTX²-C9 or MTX²-C12 and to efficiently and stably dimerize *E. coli* DHFR.

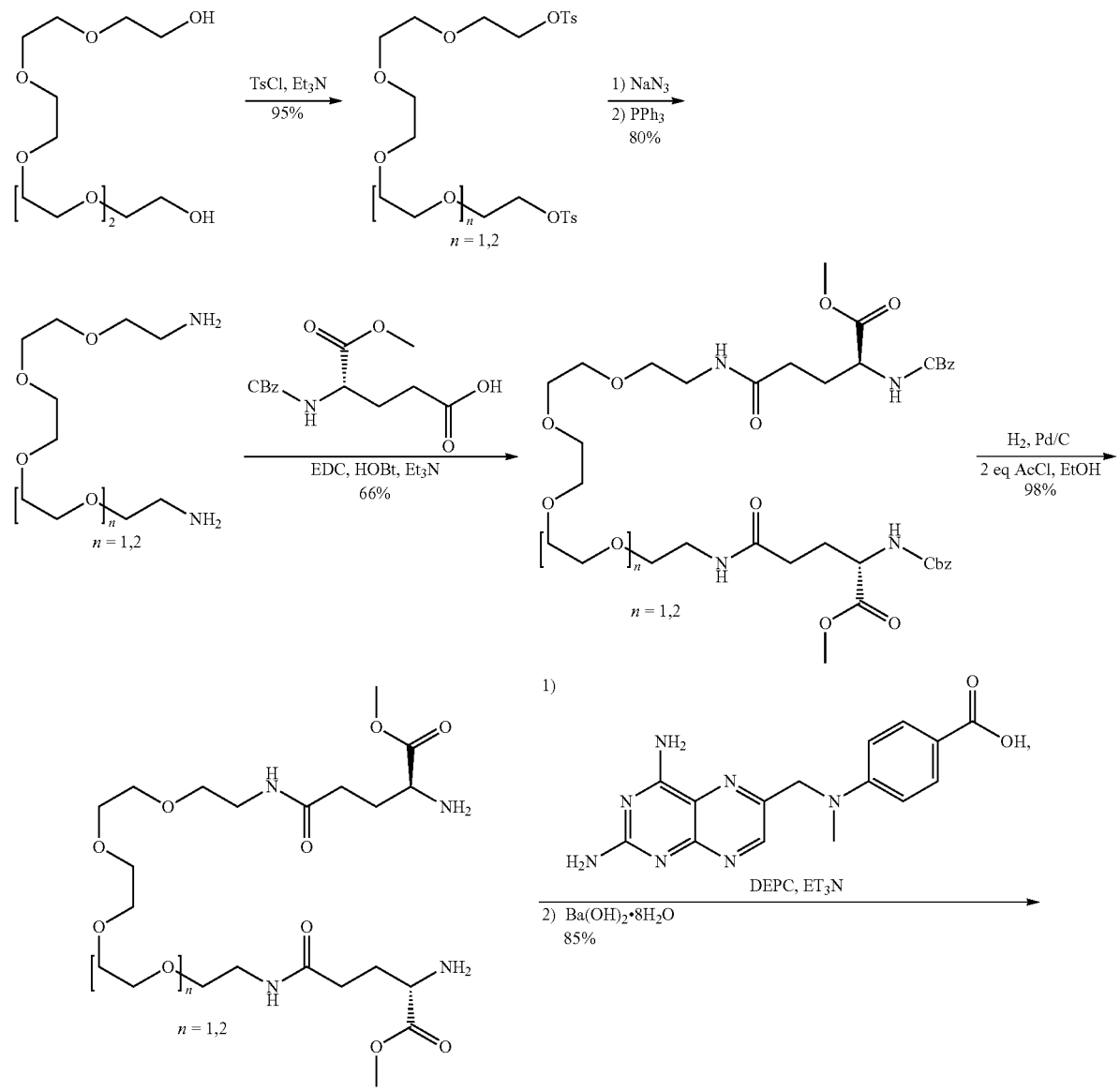

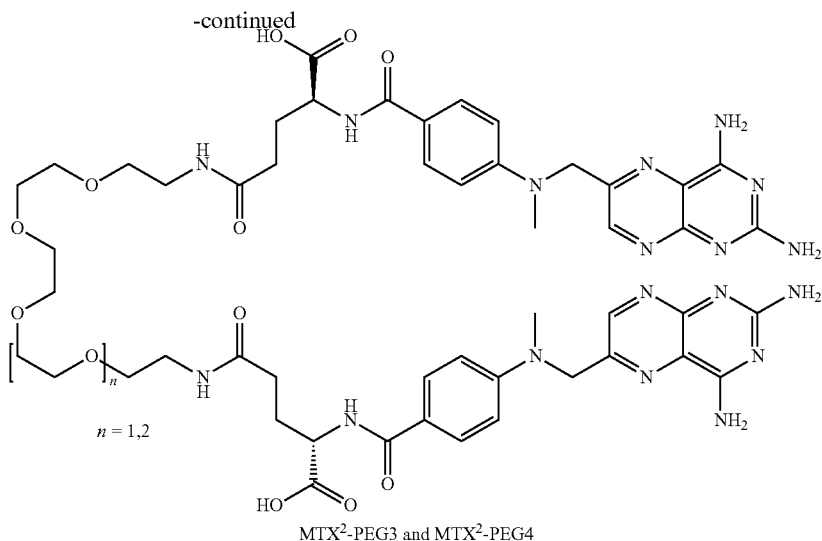

MTX²-PEG3 and MTX²-PEG4

EXAMPLE 5

Biological Activity of Anti-CD19 and Anti-CD22 Immunotoxins

Anti-CD19 and anti-CD22 based immunotoxins have been engineered and prepared. (Vallera et al., 2005) To summarize, a novel bispecific scFV fused to the diphtheria toxin catalytic and translocation domains (DTCD19CD22) that is capable of recognizing CD19 and CD22 can be expressed in bacteria and purified in high yield after refolding using a sodium N-lauroyl-sarcosine air oxidation method. DTCD19CD22 exhibited greater anticancer activity than the immunotoxins incorporating monovalent or bivalent anti-CD19 and anti-CD22 scFvs. The bispecific immunotoxin, also, exhibited a greater avidity for CD19+, CD22+ human leukemia Daudi and Rajj cell lines. Site-directed mutagenesis was used to further enhance binding to these cell lines, as well as patient cells. In vivo, DTCD19CD22 was effective in a flank tumor therapy and systemic SCID tumor model at significant inhibiting tumor growth (p<0.05), while prolonging survival.

EXAMPLE 6

DHFR-DHFR Fusion Protein Construction and Purification

Paired DHFR fusion proteins were constructed using a plasmid template previously described based on the pFLAG-ATS expression vector. (Sticha et al., 1997). The wild type *E. coli* DHFR gene was amplified from the plasmid ptZ19R; the PCR primers supplied the KpnI (GGTACC) and XbaI (TCTAGA) restriction sites at the 5' and 3' termini, respectively. The amplified DNA was inserted into a TA cloning vector (Invitrogen, Inc.) and transformed into Xl1Blue cells (Stratagene, Inc.); recombinant colonies were identified by the blue/white screening method and the DHFR-containing plasmids were isolated via miniprep (Promega) and sequenced. Sequential digestion of the purified plasmid DNA with KpnI and XbaI yielded the appropriate sticky ended fragment for ligation into the double-digested (KpnI-XbaI) pPH70D vector. Ligation with T4 DNA ligase followed by transformation into supercompetent XL1-Blue cells yielded colonies bearing the ligated plasmid. The identity of the assembled plasmid was initially not confirmed by DNA sequencing; rather, the IPTG inducible expression of a 36 kD protein was verified by polyacrylamide gel electrophoresis. Later DNA sequencing and restriction analysis were consistent with expression of the DHFR dimer. This plasmid containing encoding the FLAG peptide sequence at the N-terminus followed by two wild-type DHFR modules separated by a 13 ($GLG_5LVPRGT$) (SEQ ID NO: 1) amino acid linker was designated pF13DD and the expressed protein $DHFR^2$-13. As it became evident from oligomerization experiments that the length and composition of the peptide linker is a major determinant of nanoring size and shape, four additional dimeric DHFRs with shortened linkers were prepared. Plasmids encoding a 7 ($GLG_4T$) (SEQ ID NO: 2), 3 ($G_2T$), 1 (G), and 1(T) amino acid linker were constructed by Quick Change Deletion Mutagenesis, affording the plasmids pF7DD, pF3DD, pF1G-DD, and pF1T-DD. DNA sequencing confirmed that the desired linker had been incorporated. Similar levels of over-expression for the proteins $DHFR^2$-13, $DHFR^2$-7, $DHFR^2$-3, $DHFR^2$-1G, and $DHFR^2$-1T were observed. Typically, after cell lysis, each of the proteins was loaded on to a MTX-resin affinity column, washed with a high salt buffer to remove non-specific binding proteins, then eluted with 2 mM folate. After dialysis and passage through a DEAE ion-exchange column, 20-40 mg of purified protein could be obtained per liter of terrific broth. The functional status of the DHFR dimers was established by determining the enzymatic activity with dihydrofolate and NADPH. In addition, active site titration with MTX established the concentration of functional protein, when compare to solution protein concentrations determined by the Bradford method. As expected the enzyme activity of the DHFR dimers was found to be exactly twice that of wild type DHFR.

EXAMPLE 7

SEC of DHFR-DHFR Fusion Protein Oligomerization

SEC was employed to initially assess the degree of $DHFR^2$ induced oligomerization by $MTX^2$. The purified $DHFR^2$-13 (10 uM) and $MTX^2$-C9 were mixed at a range of stoichiometries, allowed to equilibrate for one hour, and assayed by size exclusion chromatography on a Superdex G75 Column (Amersham). In the absence of MTX$^2$-C9, the protein was observed to elute at 20.9 minutes, which, when related to a standard calibration curve, corresponded to a calculated molecular weight of 44.6 kD, in good agreement with the actual molecular weight of 381(D.

As the relative ratio of MTX$^2$-C9 was increased from 0.25 to 1.0 equivalents, the formation of two distinct larger species was observed. Comparison to the standard curve revealed that the observed retention volumes of these new peaks corresponded to dimeric (89.9 kD) and trimeric (120.5 kD) assemblies. A shoulder on the trimer peak suggested the formation of a small amount of tetrameric or larger oligomers. Assemblies of this size, however, approach or exceed the exclusion limit of the G75 matrix, preventing definitive assignment of the molecular weight and oligomer number. The dimeric fraction increased at the expense of the larger oligomers with time, becoming the dominant species. The incubation of either DHFR$^2$-3, DHFR$^2$-1G or DHFR$^2$-1T and 1 or 2 equivalents of MTX$^2$-C9 for 30 min revealed preferential formation of larger oligomers. For DHFR$^2$-3, tetramers were the dominant species, further increasing with time. Oligomerization of DHFR$^2$-1G revealed that formation of octamers was preferred, while substitution of the glycine linker for a threonine linker resulted in an increased amount of septamer, hexamer, pentamer and tetramer. These results demonstrate the importance of linker length and composition on the chemical induction of DHFR$^2$ oligomers. When either the dimers for DHFR$^2$-13, or tetramers for DHFR$^2$-3 or octamers for DHFR$^2$-1G were isolated by SEC and stored for 2 weeks at 4° C., no change in the oligomer composition could be observed on re-injection. In addition, in contrast to the expected result from linear oligomers, no observable change in composition was observed when oligomer samples were dilution to a concentration of 5 nM. These results are consistent with highly stable and circular rings and not linear oligomers.

EXAMPLE 8

Dynamic and Static Light Scattering Studies of DHFR-DHFR Fusion Protein Oligomerization The assembly of DHFR nanoclusters was characterized with dynamic and static light scattering. Initial dynamic light scattering (DLS) studies employed a custom-built apparatus with a 50-200 mW 488 nm argon laser light source. Data collection and analysis employed software from Brookhaven Instruments. Solutions of purified DHFR$^2$ were successively ultrafiltered with 0.2 μm and 0.02 μm membranes to remove dust, then mixed with equivalently filtered solutions of MTX2C9 in phosphate buffer. For concentration studies, the assembled mixture was allowed to equilibrate for 15-20 minutes and then diluted with appropriate volumes of ultrafiltered buffer into individual aliquots.

TABLE 2

Calculated and Determined Radii of Gyration and Hydration for the Octomer.

| Oligomer | Rg | Rh | Rg/Rh |
|---|---|---|---|
| Linear | 18.5$^a$ | 9.7$^a$ | 1.9 |
| Ring | 10.4$^a$ | 8.3$^a$ | 1.25 |
| Sphere | 7.0$^b$ | — | — |
| Experimental | 11.4 | 8.7 | 1.31 |

$^a$Calculated with Hydro—Garcia de la Torre, et al. (REF),
$^b$Calculated from Rg = 0.77 * Rh

TABLE 3

Oligomeric Dimensions by DLS and SLS.

| Oligomer | Rg (nm) | Rh (nm) | Rg/Rh |
|---|---|---|---|
| Linear | 18.5$^a$ | 9.7$^a$ | 1.9 |
| Ring | 10.4$^a$ | 8.3$^a$ | 1.25 |
| Sphere | 7.0$^b$ | — | — |
| Expt. | 11.4 | 8.7 | 1.31 |

$^a$Calculated with HYDRO$^2$
$^b$Rg = 0.77 * Rh for solid sphere.

In DLS experiments, scattered counts at 90 degrees were collected for 60-90 seconds and the autocorrelated data analyzed by both cumulant and non-negative least squares (NNLS) regression analysis. For the NNLS calculation, the measured and calculated baselines were compared, and the measured baseline was used to derive the distribution of hydrodynamic radii. Raw scattering data for each sample were collected a minimum of three times and analyzed independently, to control for the influence of dust-related, electronic, or photodynamic noise.

Static light scattering experiments were conducted with the same apparatus, and the scattering intensity sampled at 10 degree increments from 30 to 130 degrees. Ultrafiltered toluene and phosphate buffer served as the reference and blank controls, respectively. Five to seven concentrations were used for each experimental dataset, with concentrations spanning a minimum 4-fold range, typically from 0.2 to 1.2 mg/mL total protein concentration. The collected data were analyzed by the Zimm plot method to determine the average molecular weight and radius of gyration for each sample.

The results of both SLS and DLS were consistent with analysis by SEC that revealed the predominant oligomer as a cyclic octamer. The ratio of the Rg/Rh was found to be 1.31, which is with in the experimental error of the calculated values for a ring with a diameter of 22-26 nm. The low polydispersion found by DLS indicates that the species found in the sample are reasonably homogenous. This is also consistent with SEC analysis of these oligomers.

EXAMPLE 9

TEM and Cryo-TEM Studies of DHFR-DHFR Fusion Protein Oligomers

Given that analysis of the chemically induced DHFR$^2$ oligomers were determined to likely be rings or polygons, transmission electron microscopy (TEM) and Cryo-TEM images of samples of octamers prepared from DHFR$^2$-1G and MTX$^2$-C9 were collected.

TEM

Samples of DHFR$^2$-1G-MTX$^2$-C9 octamers were prepared for transmission electron microscopy (TEM) by air drying of droplets (4 mg/mL) onto carbon-coated, Formvar-covered 200 mesh Cu TEM grids and negatively stained with a 1% w/w solution of uranyl acetate. Images, electron diffraction patterns and energy-dispersive X-ray spectra were recorded in a JEOL 1200EX or 2000FX electron microscope operating at 120 or 200 kV, respectively. A relatively homogeneous number of rings can be observed. The dimensions of the rings ranged in diameter from 22 to 30 nm in size. No linear oligomers were observable, consistent with the results found from LS experiments.

Cryo-TEM

CryoTEM samples were prepared in a controlled environment vitrification system (CEVS) which contained saturated water vapor to prevent the evaporation of water from sample solutions. All the samples were prepared at room temperature. Typically, a micropipette was to use to load a drop of micelle solution (5 µL) onto a lacey carbon supported grid. The excess solution was blotted by a piece of filter paper, resulting in the formation of freely spanning thin films of 100–300 nm thickness on the holes. After about 30 seconds the samples were quickly plunged into a reservoir of liquid ethane (cooled by liquid nitrogen) at its melting temperature. The vitrified samples were mounted on a cryogenic sample holder (Gatan 626) and examined with a JEOL 1210 TEM (120 Kv) at approximately −175° C. A minimal dose procedure was employed to reduce radiolysis. The phase contrast was enhanced by underfocus in the range of 1 mm to 20 mm. The images were recorded on a Gatan 724 multiscan CCD and processed with DigitalMicrographs version 3.3.1. The ramp-shaped optical density gradients in the background were digitally corrected. Analysis revealed a number of circular structures with diameters ranging from 18 to 28 nm. Consistent with our previous analysis of $DHFR^2$-$MTX^2$ oligomers by LS and TEM.

EXAMPLE 10

MTX-MTX($MTX^2$) Conjugates of: a) the Fluorophore, Alexa Fluor 488, and b) the Drugs, Doxorubicin and Auristatin Based on x-ray structure analysis of DHFR dimerized by $MTX^2$, the linker remains flexible and does not interact with the protein. Consequently, MTX dimers that contain at least one additional linker emanating from a central amino group will provide a route to the construction of multi, e.g., tri-functional protein dimerizers. $DHFR^2$-scFv nanorings containing the additional cargo molecule will then be assembled. Tri-functional MTX DHFR dimerizers will be constructed that can serve as; 1) fluorescent probes for cellular uptake studies and 2) delivery vehicles for compounds such as the anticancer drugs, doxorubicin and auristatin.

The design of the tri-functional MTX dimerizers incorporates a number of important features. First, an 11 atom polyamine linker will be used to connect to two MTXs. This should be of sufficient length, since no significant difference in the dimerization of DHFR by MTX dimers containing from 9-18 atoms has been observed. Second, to improve water solubility and reduce possible ligand-ligand induced nanoring aggregation, the third linker will be a polyethylene glycol (PEG) chain. Next, a lysosomal protease sensitive spacer will be appended that upon cell uptake will release the drug. Senter and coworkers have recently shown that immunoconjugates of auristatin incorporating the cathepsin B cleavable valine and citruline based linkers are highly stable in mouse plasma and potent anticancer agents, both in vitro and in vivo.

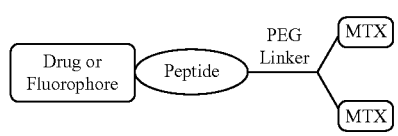

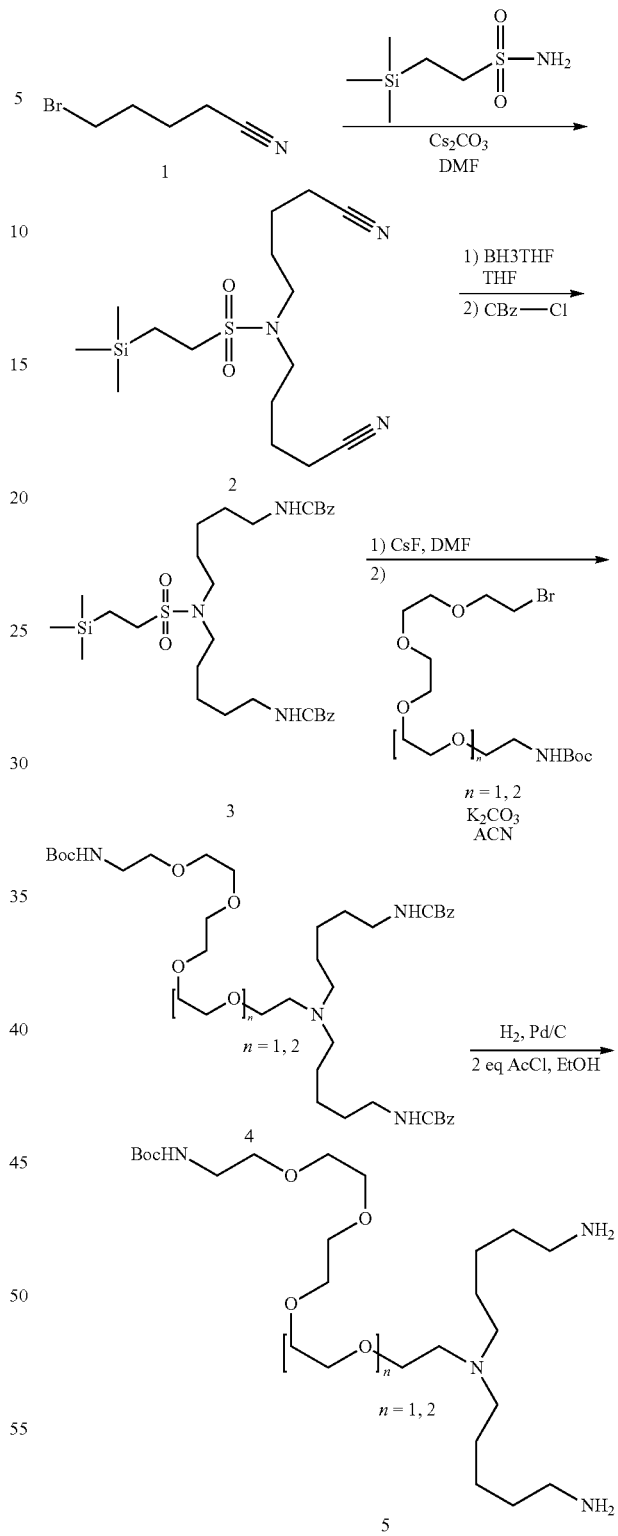

As the drugs to be delivered, two representative compounds were chosen, doxorubicin and auristatin, because they are highly potent, have substantial dose limiting toxicities and operate by differing mechanisms of action. Doxorubicin is a broadly active clinically used anticancer drug, whose utility has suffered due to dose limiting cardiotoxicities. Doxorubicin initiates cell death by the dual processes of binding to genomic DNA, while contributing to cellular oxidative stress. Auristatin is a member of the dolastatin family of natural products with potent anticancer activity. Like taxol, auristatin is an inhibitor of tubulin polymerization and may also cause damage to the vasculature of solid tumors. Auristatin is broadly active in vitro ($IC_{50}$=3.2±0.51 nm against 39 human tumor cell lines), lacks sufficient clinical efficacy. To enhance the efficacy of doxorubicin and auristatin, Mab conjugates have been prepared and shown to be potent and selective anticancer agents in vitro and in vivo. Consequently, given the wealth of data that exists already on antibody conjugates of these drugs and their effectiveness against B-cell leukemias, $MTX^2$ conjugates of doxorubicin and auristatin will be constructed and their ability to dimerize DHFR and assemble $DHFR^2$ nanorings will be determined.

10.a. Synthesis of Trivalent Linker.

A part of the synthesis of our $MTX^2$-conjugates will be the preparation of the trivalent linker, 5. (Scheme 2) Based on the methodologies of Parker (Parker et al., 2003) for the synthesis of linear and cyclic triamines, the trimethylsilyl-ethane-sulfoamide SES protected bis-cyanobutylamine, 2, will be prepared from 5-bromovaleronitrile and $SES-NH_2$ in the presence of cesium carbonate. After reduction of the cyano groups with boran-THF, the amines will be protected by treatment with carbobenzyloxy chloride (CBZ-Cl) yielding the compound 3. After removal of the SES protecting group by cesium fluoride, the third arm of the trivalent linker will be installed by alkylation with PEG5-NHBoc bromides (4). (Phanstiel et al., 2000) If it becomes apparent that it would enhance nanoring formation and cellular uptake, PEG linkers of greater length and water solubility can be incorporated. Removal of the Cbz groups by hydrogenation will yield the appropriate differentially protected tetramine, 5.

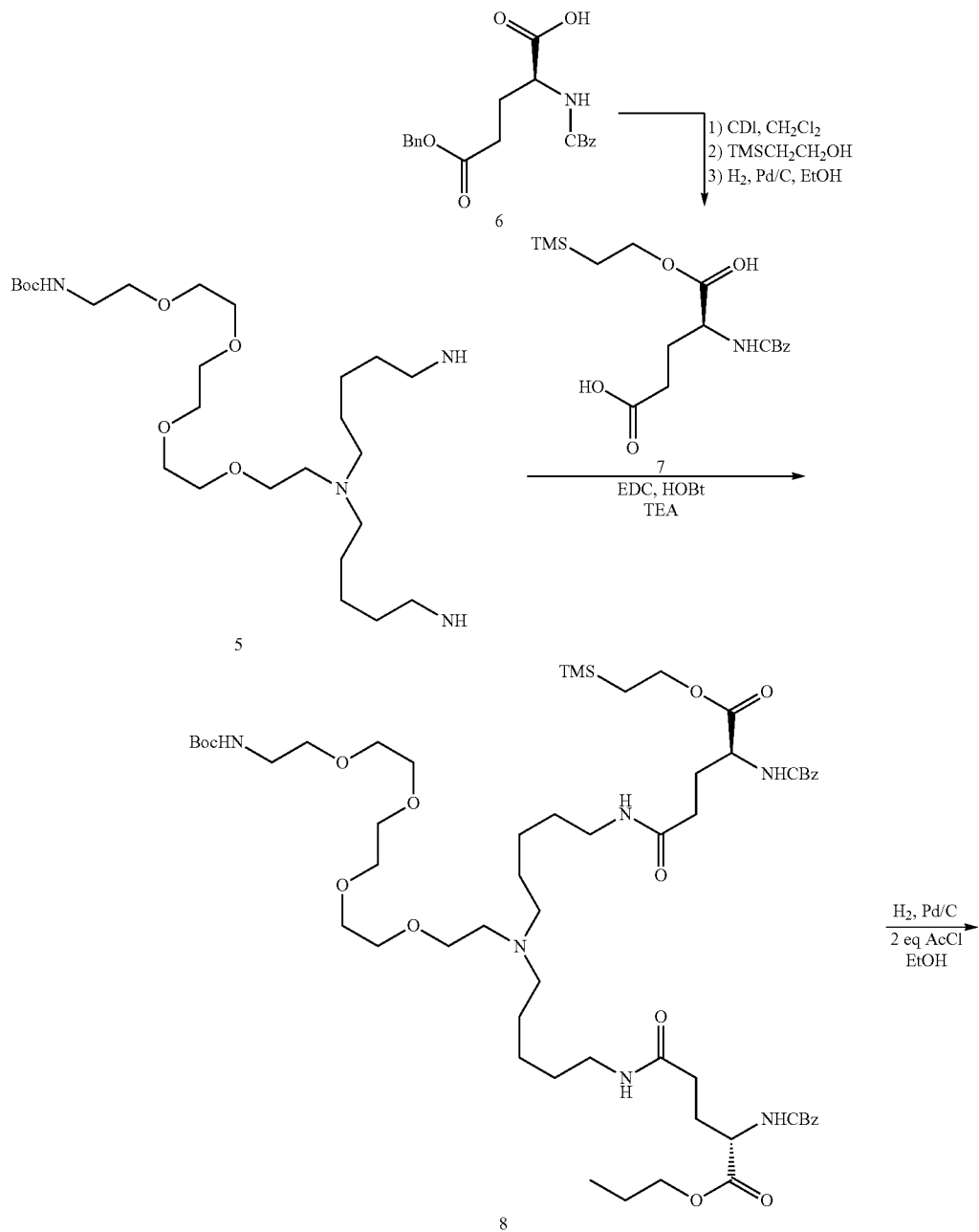

-continued
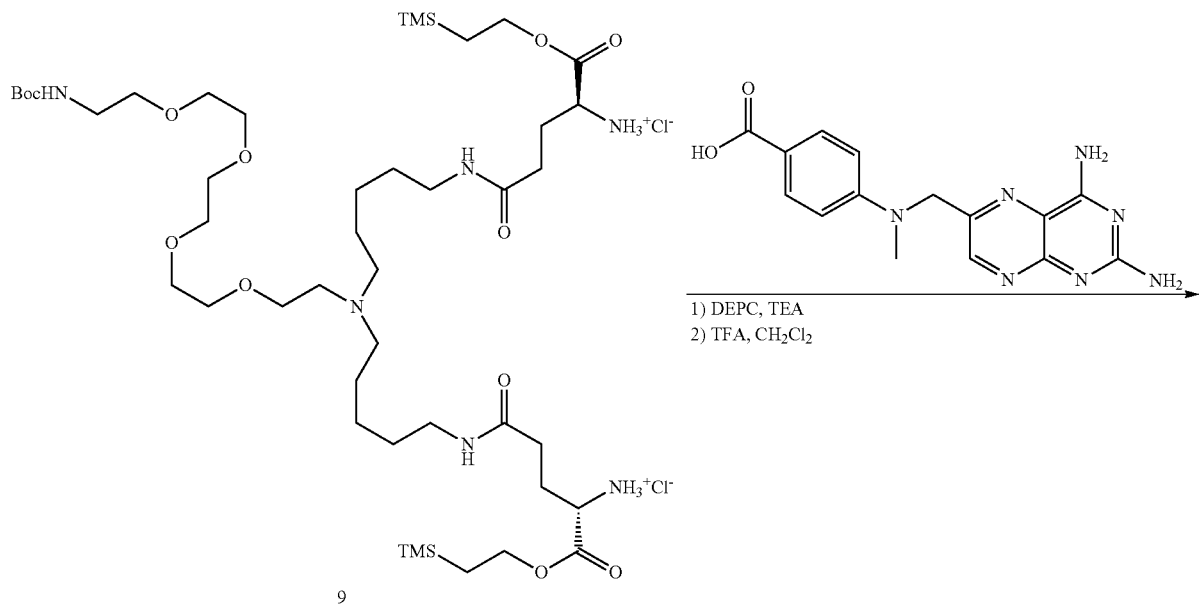
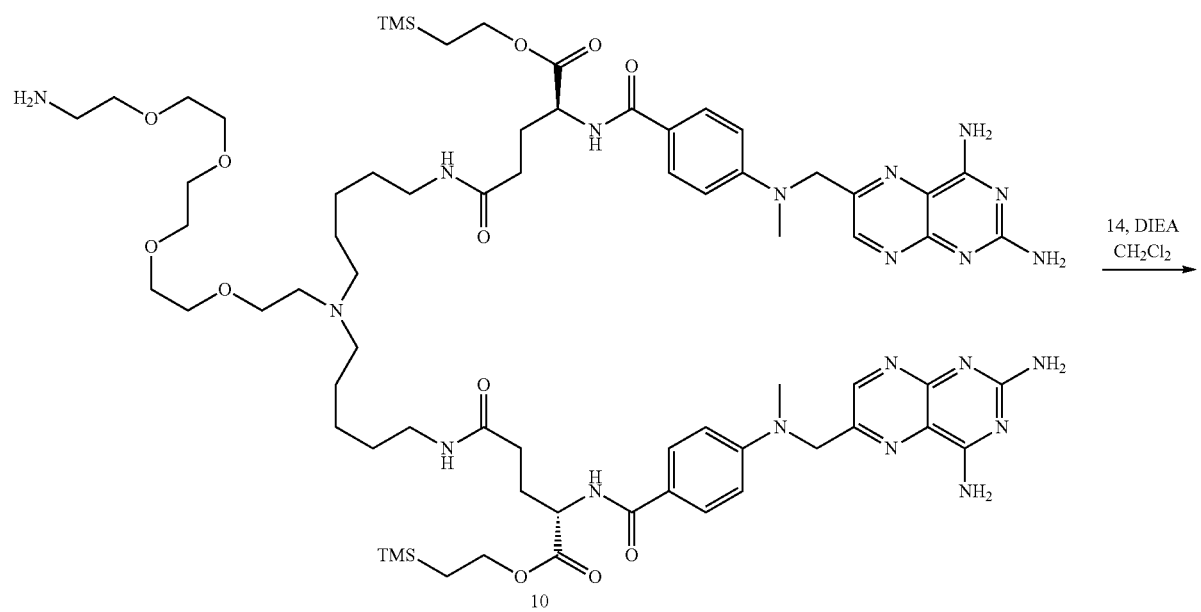

-continued

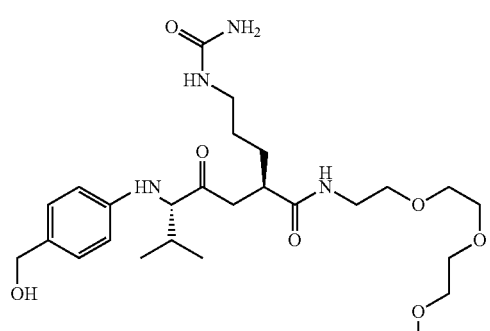

11

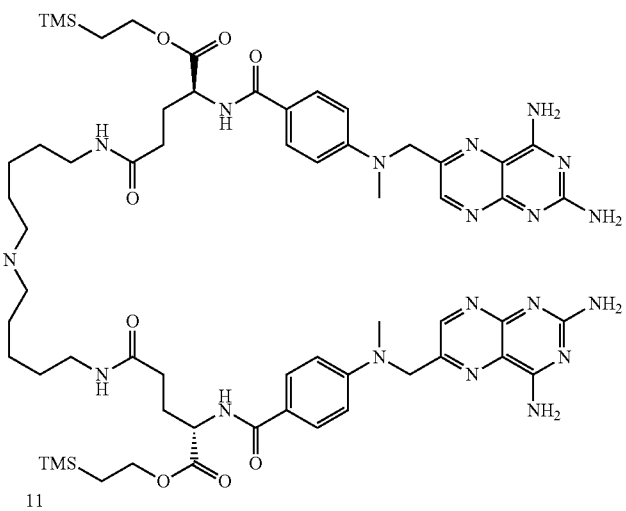

Because of the need for greater flexibility with regard to protecting group removal, the previous MTX$^2$ synthesis (Carlson et al., 2003) to include the protection of the di-protected glutamate, 6, with a trimethylsilyl ethyl moiety, instead of as a methyl ester. (Scheme 3) This strategy has been successfully applied to the synthesis of folate-drug and folate-phosphoramidite conjugates. Compound 7 will be prepared from 6 by treatment with the coupling agent carboxy-dimmidazole (CDI) and trimethylsilyl ethanol, followed by removal of the benzyl protecting group by hydrogenation, yielding 8. The silyl-protected glutamate will be coupled to 5 in the presence of EDC and HOBT and the Cbz protecting groups removed by catalytic hydrogention to yield 9. Next, 10 will be prepared by DEPC assisted coupling of to the free amine, followed by removal of the Boc group. We have found that this procedure is superior to standard EDC or DCC based methods.

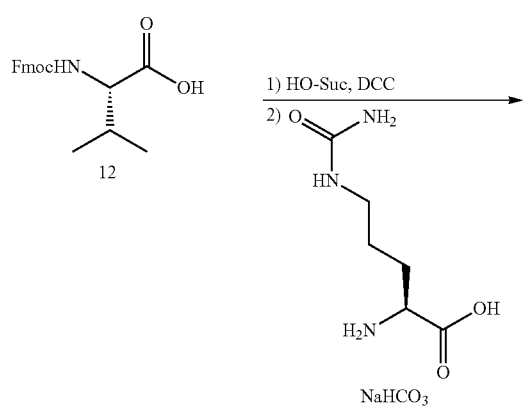

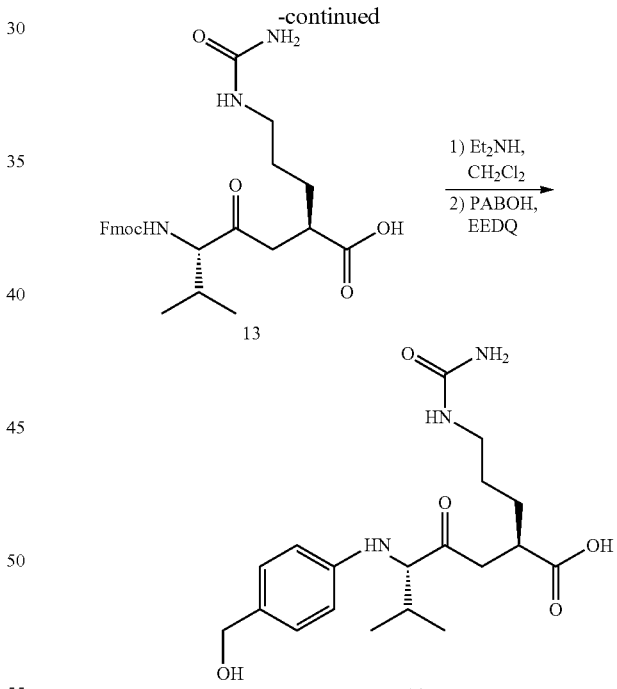

To prepare the trivalent linker with the cathepsin B cleavable linker, the valine citruline p-aminobenzyloxycarbonyl (PABOH) peptide spacer (14) will be prepared. (Dubowchik et al., 2002) (Scheme 4) Starting with Fmoc protected valine (12), the Fmoc valine-citruline dipeptide will be synthesized by first activating 12 with N-hydroxy succinimide, followed by the addition of citrulline in sodium dicarbonate. The dipeptide, 13, will be coupled to PABOH in the presence of EEDQ, after removal of the Fmoc group by diethylamine, yielding 14. The final protease sensitive trivalent linker, 15 will be synthesized by coupling 14 and 10 in the presence of DIEA.

10. b. Synthesis of MTX²-Alexa Fluor 488

The preparation of a MTX dimer conjugated to a fluorophore will be carried out with Alexa Fluor 488 (Invitrogen-Molecular Probes, Inc.). Although fluoresceine is widely used for cell based fluorescent ligand experiments, Alexa Fluor 488 will be used instead of fluoresceine because of its greater fluorescence brightness, greater photostability, excellent water solubility and enhanced pH (4-10) insensitivity. These qualities make it an excellent reagent for monitoring the cellular uptake of scFv-nanorings, particularly by FACS analysis and fluorescence microscopy. After removal of the Boc protecting groups with trifluoroacidic acid and the silyl protecting groups by TBAF from 10, the primary amine of the PEG5 linker will be conjugated to the succiniyl ester of Alexa Fluor 488 to yield 15. (Scheme 5)

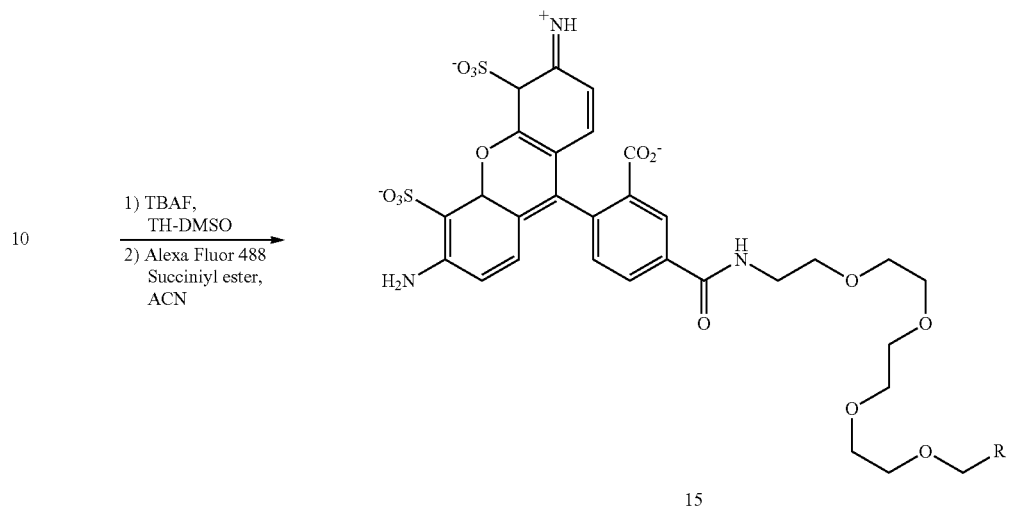

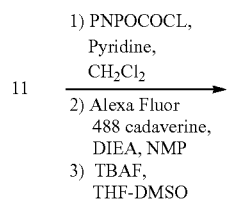

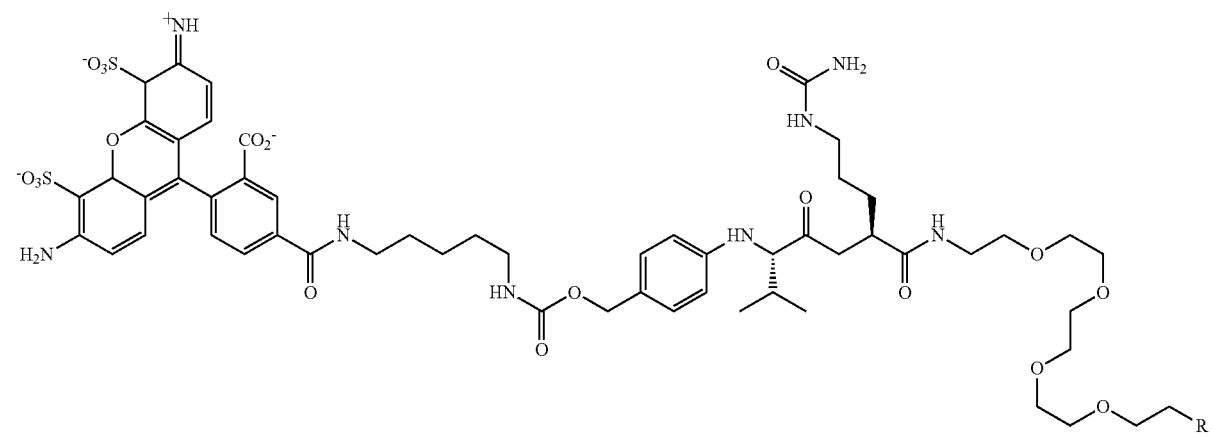

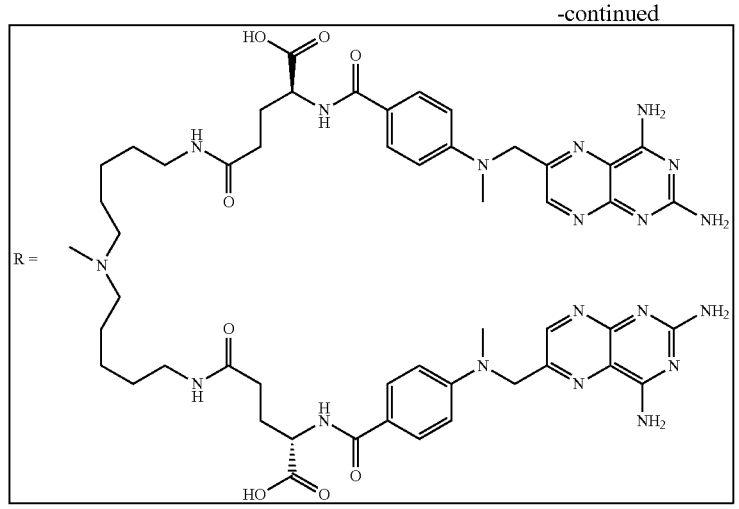

In order to monitor not only cellular uptake but lysosomal release, fluorogenic cathepsin B sensitive MTX$^2$ conjugates will be prepared. In a procedure similar to that reported previously for immunoconjugates, 11 will be treated with p-nitrophenyl chloroformate in pyridine and reacted with Alexa Fluor 488-cadaverine (Invitrogen-Molecular Probes, Inc.) Yields from 65-75% have been observed for conjugations with primary and secondary amines. Removal of the remaining silyl protecting groups with TBAF should afford quantitatively compound 16.

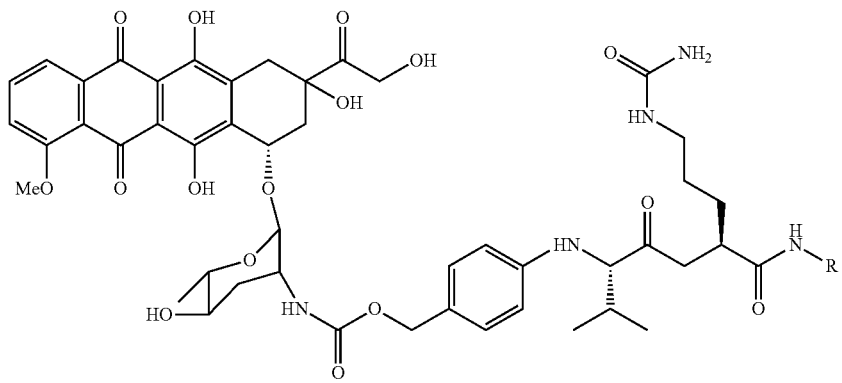

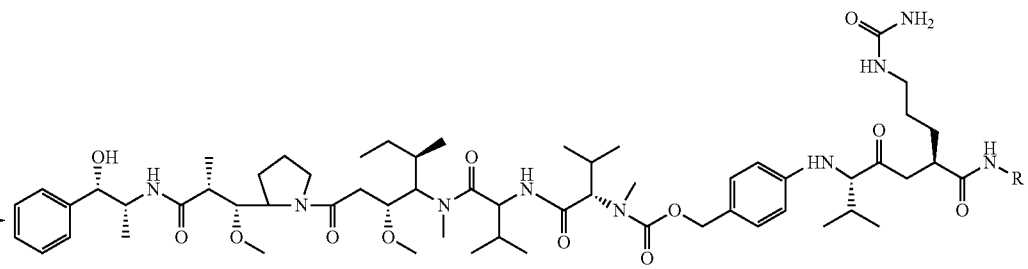

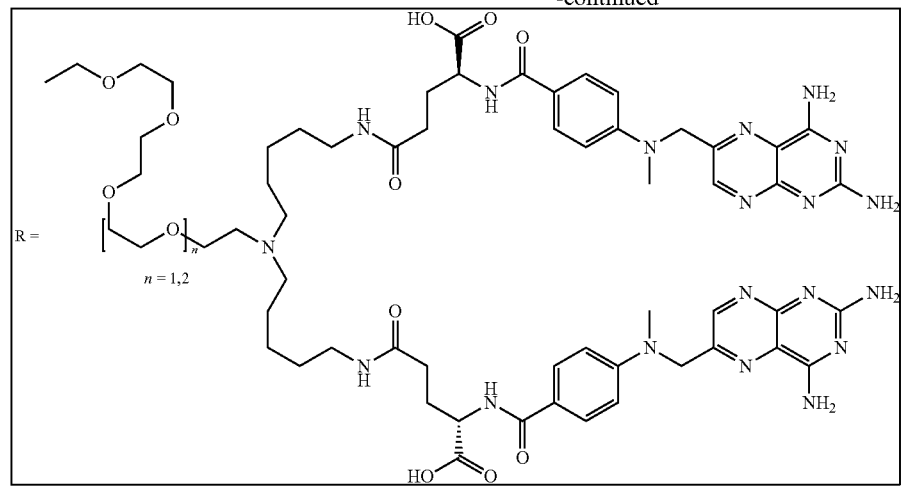

10. c. Synthesis of MTX²-Doxorubicin and Auristatin

Preparation of the MTX dimer conjugates to the Doxorubicin and Auristatin will be carried out by a procedure similar to that reported previously for immunoconjugates of these drugs. (Scheme 6) Doxorubicin (Sigma-Aldrich, Inc.) is commercially available and monomethyl auristatin E (MMAE) will be prepared as previously reported by Dr. Senter and coworkers. Compound 11 will be treated with p-nitrophenyl chloroformate in pyridine and reacted with either doxorubicin or MMAE. Yields for this reaction with doxorubicin or MMAE range from 65-75%. Removal of the remaining silyl protecting groups with TBAF should afford quantitatively either compound 13 or 14. To monitor the necessity of cathepsin B activation on antitumor activity, an alternative linker will be constructed with D-valine and D-citruline. Peptides containing D-amino acids have been shown not to be substrates for cathepsin.

$$[E] = \frac{-(1 + K_{a1}[D_a]) + \sqrt{(1 + K_{a1}[D_a])^2 + 8K_{a1}K_{a2}K_c[D_a]E_t}}{4K_{a1}K_{a2}K_c[D_a]}$$

10. d. DHFR Dimerization Studies with Compounds 15-18

The ability of the MTX² compounds 15-18 to dimerize E. coli DHFR will be determined and compared to the previous results for MTX²-C9 and MTX²-C12. E. coli DHFR (5 uM) will be incubated in P500 buffer (0.5M NaCl, 50 mM potassium phosphate, 1 mM EDTA, pH 7.0) with 5% (v/v) glycerol for a minimum of 3 hr with varying amounts of the compound in final stoichiometric ratios of dimerizer:protein ranging from 0.1:1 to 50:1. The mixtures will fractionated on a Sephadex G-200 size exclusion column eluting with P500 buffer, and the amount of monomeric and dimeric protein quantitated by absorbance at 280 nm. Incubations from 30 min to 5 days yield identical results, indicating that equilibrium is reached with in one hour. Microsoft Excel will be used to model the dimerization data as a function of free ligand concentration. The expression for free enzyme concentration below is the basic expression from which the concentrations of the remaining species will be derived with equation 1. It is expected that all of the compounds will efficiently and stably dimerize E. coli DHFR in a manner similar to that found for MTX²-C9 and MTX²-C12. If this does not occur, it is likely that the drug may be interfering with protein dimerization. Additional analogs incorporating longer PEG linkers (e.g., PEG6) will be synthesized and evaluated.

10. e. Cleavage DHFR-MTX²-Drug Cathepsin B Linker

The efficacy of eventual drug delivery by the antibody-drug nanorings will be affected by the efficiency with which the incorporated protease sensitive linker can be cleaved. Previously, immunoconjugates bearing this Val-Cit site have been shown to be excellent substrates for cathepsin B. Since each subunit of a nanoring is chemically dimerized DHFR, these experiments will be conducted by determining the ability of DHFR dimerized by compounds 15-18 to release Alexa Flour 488, doxorubicin and auristatin. E. coli DHFR will be incubated with a final stoichiometric ratio of dimerizer:protein of 0.5:1. Non-bound dimerizer will be removed from the DHFR-Dimerizer complexes by centrifugation with PD-10 SEC column. Assay conditions will be chosen to approximate those of an intracellular lysosome. The DHFR-dimerizer complexes will be dissolved in PBS (pH 7.0) and diluted into the acetate/EDTA (pH 5.0) reaction buffer, followed by the addition of either human and mouse cathepsin B (R&D Systemes). At various time points aliquots will be removed and the amount of MTX²-Drug or MTX²-Fluorophore, Drug or Fluorophore, and MTX² determined by HPLC after centrifugation. Half-lives will be calculated by calibration of the released Drug/Fluorophore peak areas with a standard curve of known Drug or Fluorophore concentrations. Previously, >90% of a drug has been shown to be released from immunoconjugates that have incorporated cathepsin B sensitive linkers.

10. f. X-Ray Crystal Structure Analysis of DHFR²-15-18 Complexes.

Full characterization of the molecular structure of the DHFR-MTX²-Drug/Fluorphore complexes will be important to understanding the effect of the tri-functional dimerizer on DHFR oligomerization and drug release. The potential for either Alexa Fluor 488, Doxorubicin or Auristatin to stably bind at an alternative site on DHFR is a possibility given their size and hydrophobicity. In addition, the impact of these moieties on DHFR dimerization will play a role in predicting the impact of our ligand design on the development of novel heterodimerizing DHFRs.

Protein Crystallization

DHFR enzymes and their inhibitor complexes will be submitted to a high-throughput robotic screen. This screen is comprised of 1536 different crystallization cocktails in an incomplete factorial matrix. The solutions are derived from mixtures of inorganic salts and buffers, various polyethylene glycols, MPD and other organics. The matrix also includes crystal screens 1 and 2 (Hampton Research Inc.). The crystallizations occur in 0.4 µL drops by the batch method under oil. In addition to the robot screening, manual screening to optimize crystal growth conditions will be carried out. DHFR samples are generally concentrated to between 10~20 mg/mL in buffers promoting mondispersity as assessed by light scattering.

X-Ray Diffraction

Initially, crystals will be screened and data collected using a $CuK_\alpha$ rotating anode source with an R-axis IV detector. All data will be collected at low temperature after cryopreservation conditions have been determined for each crystal. HWI scientists also have experience collecting data at the APS, Brookhaven, Cornell and Stanford synchrotron beamlines. Two different methods of data collection and phasing can be used to solve the DHFR inhibitor complexes: Multi-wavelength anomalous dispersion (MAD) and Multiple Isomorphous Replacement (MIR). Since the DHFR enzyme family is highly homologous, it is anticipated that the majority of the structures will be solved by molecular replacement or difference Fourier techniques. However, the complete complement of phasing methods can be used if necessary. Should the need arise, expression of seleno-methionine substituted protein for crystallographic phasing can be carried out. The protocol used for growing the selenomethionine derivative is based on Van Duyne and coworkers.

Data Processing and Phasing

Data sets will be integrated using DENZO and scaled and averaged using SCALEPACK as implemented by the HKL2000 package. BnP, a new hybrid program based on the HWI Shake and Bake algorithm, will be used to determine the substructure (S or Se) by direct methods (SnB) and then generate MAD phases (PHASES). BnP has a distinct advantage in solving protein structures with large substructures through the direct methods algorithm used in SnB. In addition, SOLVE will be used as a backup for structure solution, which can be more successful using Patterson correlation in cases of small substructure. RESOLVE can also be used to automatically fit the experimental electron density map.

Structural Refinement and Analysis.

The positions of substructure atoms will be refined and initial electron density maps calculated using CNS. Cycles of refinement using combined model and experimental (Hendrickson-Lattman coefficients) phases will be combined with manual fitting of residues in electron density maps using TURBO-FRODO. Typically, reiterative cycles of model building and refinement are used to determine the complete structure with suitable refinement statistics. At least 10% of the reflections will be reserved for calculation of R-free as it has been shown a good indicator of the correctness of the refinement. Programs such as PROCHECK will be used to evaluate the correctness of the model geometry. Progress will be monitored by referencing $R_{free}$ and calculating omit maps and a real space R-factor by residue. All DHFR complexes obtained will be thoroughly analyzed with regard to tertiary structure, cavity makeup, and structural motifs. Calculations of salt links, hydrogen bonds, solvent-accessible surface area and root mean square differences (RMSD) will be performed with CNS. GRASP will be used to calculate properties related to the molecular surface, such as the surface to volume ratio, electrostatic potential, and cavity identification. Molecular dynamics and ligand docking and analysis will take place within the SYBL (Tripos) suite of programs.

EXAMPLE 11

Anti-CD19 and Anti-CD-22 $DHFR^2$ Based Polyvalent Nanorings

A variety of antigens have been used to develop immunotoxin as well as antibody drug conjugates. For B-cell leukemias, several cell surface antigens, including CD19 and CD22 have been investigated as immunotherapy targeting antigens. CD19 is a 95-kDa membrane glycoprotein and one of the most ubiquitous markers expressed on B-cells. It is expressed only on late pre-B-cells and mature B-cells and is broadly expressed on B-cell leukemias and lymphomas, such as B lineage lymphoblastic leukemia (B-ALL) the most common form of childhood leukemia. Knock-out and over-expression studies have demonstrated the importance of CD19 to B-cell activation, proliferation and differentiation. CD22 is a 135-kDa B lymphocyte specific glycoprotein and member of the sialoadhesin protein family. It functions as a regulator of B-cell responses, most probably by recruiting key signaling molecules to the antigen receptor complex. Late pre-B-cells, mature cells and 60%-70% of B-cell leukemias and lymphomas express CD22. Knockout mice experiments have demonstrated the importance of CD22 to modulating the B-cell antibody responses and expansion of peritoneal B-1 cell populations.

The high level of CD19 and CD22 expression on B-cell malignancies have made them attractive targets for the development of anti-cancer immunotoxins. Anti-CD19 and anti-CD22 scFv diphtheria toxin fusion proteins are potent and selective anti-B-cell leukemia agents, both in vitro and in vivo. In addition, the simultaneous treatment of B-cell leukemia cells in vitro and in vivo with anti-CD19 and anti-CD22 immunotoxins is more potent than when they are given singularly. In addition, an anti-CD19 and anti-CD22 bispecific immunotoxin is more potent than mono- or divalent immunotoxins incorporating only one of the respective scFv specificities. Consequently anti-CD19 and anti-CD22 scFv-$DHFR^2$ fusion proteins capable of self-assembling, e.g., into of di-, tetra- and octavalent anti-CD19 and anti-CD22 scFv's when mixed with MTX dimer drug/fluorophore conjugates will be prepared and characterized, e.g., to assess their ability to be internalized and determine their in vitro and in vivo anti-cancer activity.

11.a. Plasmids for Expression of Anti-CD19 and Anti-CD22 sFv's with $DHFR^2$ Capable of Forming Bivalent, Tetravalent and Octavalent sFv-Nanorings.

$DHFR^2$-scFv fusion proteins that predominately form cyclic dimers, tetramers and octamers will be prepared. The $DHFR^2$-scFv fusion proteins will be constructed by altering the plasmids that encode the $DHFR^2$ 13 amino acid (pF13DD), 3 amino acid (pF3DD) and glycine (pF1-GDD) linkers. The stop codon will be removed and a 13 amino acid linker (AGENLYFQ\GIGLD) (SEQ ID NO: 3) containing a TEV protease site inserted between the Xba I site and the end of the $DHFR^2$ gene by Quick Change™ insertion mutagenesis. After amplification of the gene for either the anti-CD19 scFv from pUM19 or the anti-CD22 scFv from pUM22 with primers containing a 5'-XbaI site and 3'-Sac-I site, the respective PCR products will be double digested and ligated to the respective double digested plasmids. All plasmid sequences will be verified by double digestion with either XhoI, XbaI or SacI, followed by automated DNA sequencing of the linker and scFv regions.

11.b. Expression and Purification of DHFR²-scFv Fusion Proteins

After transformation of the *E. coli* strain BL21(DE3) (Novagen) with the plasmids, p13CD19, p3CD19, p1G-CD19, p13CD22, p3CD19 and p1G-CD22, a purification protocol will be used. (Scheme 7) The DHFR² fusion proteins will be expressed after the addition of IPTG for two hours and harvested by centrifugation. These conditions have been found to be optimum for the DHFR² proteins and scFv's. Although the DHFR² proteins are solubly expressed, the anti-CD19 and ant-CD22 scFv's are expressed in inclusion bodies. Regardless of the expression form, the DHFR²-scFv fusion proteins will be refolded using a sodium N-lauroyl-sarcosine air oxidation method. This method has been successfully used before for the incorporation of the internal disulfide bonds necessary for the correct refolding of scFv's, including the scFv's used in this proposed study. Extensive protein folding and refolding studies have demonstrated that DHFR can be fully refolded after denaturation, without lose of enzymatic activity or the ability to bind MTX. In addition, DHFR when appended to another protein will fully refold independently of the adjacent protein. MTX affinity chromatography will be used to purify the soluble refolded protein in a single step and the percentage of fully functional DHFR assessed by MTX inhibitor titration of DHFR enzymatic activity.

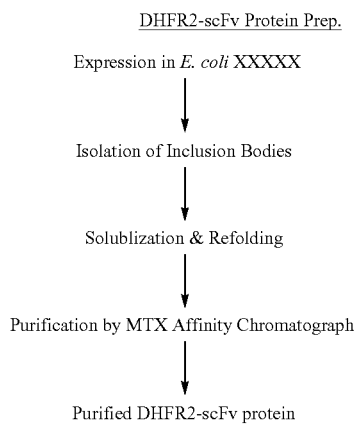

DHFR2-scFv Protein Prep.

Expression in *E. coli* XXXXX

↓

Isolation of Inclusion Bodies

↓

Solublization & Refolding

↓

Purification by MTX Affinity Chromatograph

↓

Purified DHFR2-scFv protein 11.c. EVALUATION of sFv-Nanoring Formation by Size Exclusion Chromatography (SEC), Light Scattering (LS) and Transmission Electron Microscopy (TEM).

Although this mechanism of polymerization differs from both conventional non-reversible chemical polymers and from reversible biopolymers such as actin or tubulin, the fundamental descriptors of polymer shape, size, and kinetics apply. Size-Exclusion Chromatography (SEC), Light Scattering (LS) and Cryo-TEM techniques will enable the characterization of DHFR²-scFv's-bisMTX oligomers under equilibrium conditions in solution. It is expected that the MTX chemical dimerizers of DHFR²-scFv's that have; 1) a 13 amino acid linker will form dimers, 2) a 3 amino acid linkers will form tetramers and 3) a glycine linker will form octamers.

Size-Exclusion Chromatography

For SEC analysis, the purified proteins and MTX²-C9 and compounds 15, 16, 17 and 18 will be mixed at a range of stoichiometries, allowed to equilibrate for one to twelve hours, applied to a Superdex G200 Column (Amersham) and eluted with P500 phosphate buffer. Deconvolution of the chromatogram will allow the amounts of the oligomeric species to be determined, when compared to a standard curve relating molecular weight to elution time.

Light Scattering

Static and dynamic light scattering are powerful tools that allow the size and shape of oligomeric species to be determined. Measurements of the average radius of gyration and hydrodynamic radius will be determined by static and dynamic light scattering. Initial dynamic light scattering (DLS) studies will employ a custom-built apparatus with a 50-200 mW 488 nm argon laser light source and data collection and analysis carried out with software from Brookhaven Instruments. Solutions of purified anti-CD19 or anti-CD22 DHFR²-scFv's will be ultrafiltered to remove dust and particulate, then mixed with equivalently filtered solutions of MTX²-C9 and the compounds 15, 16, 17, 18, in phosphate buffer. For concentration studies, the assembled mixture will be allowed to equilibrate for 15-20 minutes and then diluted with appropriate volumes of ultrafiltered buffer into individual aliquots.

For the DLS experiments, scattered counts at 90 degrees will be collected for 60-90 seconds and the autocorrelated data analyzed by both cumulant and non-negative least squares (NNLS) regression analysis. For the NNLS calculation, the measured and calculated baselines will be compared, and the measured baseline used to derive the distribution of hydrodynamic radii (Rh). Raw scattering data for each sample will be collected a minimum of three times and analyzed independently, to control for the influence of dust-related, electronic, or photodynamic noise.

Static light scattering experiments will be conducted with the same apparatus, and the scattering intensity sampled at 10 degree increments from 30 to 130 degrees. Ultrafiltered toluene and phosphate buffer will serve as the reference and blank controls, respectively. Five to seven concentrations will be used for each experimental dataset, with concentrations spanning a minimum 4-fold range, typically from 0.2 to 1.2 mg/mL total protein concentration. The collected data will be analyzed by the Zimm plot method to determine the average molecular weight and radius of gyration (Rg) for each sample.[52] Low polydispersion and a Rg/Rh ratio of 1.3 will indicate homogenous nanoring formation. High polydispersion and a Rg/Rh ratio approaching 1.9, will either indicate non-homogeneous nanoring formation or linear oligomer assembly. The results of these experiments will be correlated with the results from SEC.

Transmission Electron Microscopy

Cryogenic transmission electron microscopy is a powerful technique for the direct imaging of nanoscopic structures in aqueous solution. It exploits the nanometer resolution attainable with more routine EM methods, but without staining, shadowing, replicating, or otherwise perturbing the sample structure. This aspect is crucial for the analysis of characteristically "soft" structures, such as micelles and protein complexes held together by non-covalent interactions. A drop of sample solution is spread onto a porous grid, usually carbon or formvar-coated carbon. Excess solution is blotted away by hand, and then the grid is mechanically inserted extremely rapidly into a suitable cryogen (liquid ethane at 90 K is a good example). At the achieved cooling rates (in excess of 1000 degrees per sec) the water is vitrified rather than frozen, and thus the sharp volume change that accompanies ice formation is avoided. At this stage the sample is imaged with a very low electron dose. Typically the micron sized pores in the grid are filled with liquid menisci varying between 100 and 200 in thickness. The presence of undesirable ice crystals is easily detected, and samples are routinely imaged at various exposures to assess the extent of beam damage.

CryoTEM samples of the DHFR$^2$-scFvs nanorings will be prepared at room temperature in a controlled environment vitrification system (CEVS), which contains saturated water vapor to prevent the evaporation of water from sample solutions. Typically, a micropipette will be used to load a drop of micelle solution (5 µL) onto a lacey carbon supported grid. The excess solution was blotted by a piece of filter paper, resulting in the formation of freely spanning thin films of 100~300 nm thickness on the holes. After about 30 seconds the samples were quickly plunged into a reservoir of liquid ethane (cooled by liquid nitrogen) at its melting temperature. The vitrified samples will be mounted on a cryogenic sample holder (Gatan 626) and examined with a JEOL 1210 TEM (120 Kv) at approximately −175° C. A minimal dose procedure will be employed to reduce radiolysis. The phase contrast was enhanced by underfocus in the range of 1 mm to 20 mm. The images were recorded on a Gatan 724 multiscan CCD and processed with DigitalMicrographs version 3.3.1. The ramp-shaped optical density gradients in the background will digitally corrected. The size and shape of the DHFR$^2$-scFv nanorings will be determined and compared to the results from SEC and LS experiments.

11.d. Anti-CD19 and Anti-CD22 sFv Nanorings for B-Cell Leukemia Cells.

Binding (Kd) of the DHFR$^2$-scFv's nanorings assembled with MTX$^2$-C9 will be measured by homologous competition binding using radiolabeled parental antibodies anti-CD19 HD37 and anti-CD22 RFB4. During these experiments the radioligand concentration will be held constant and the non-labeled ligand varied. The preparation of radiolabeled antibodies is a well established technique. GraphPad Prism software (GraphPad Software, Inc., San Diego, Calif.) will be used to analyze the binding data using non-linear regression analysis. The technique and its use are discussed in the Prism manual entitled Analyzing data with GraphPad Prism (GraphPad Software, Inc.) Daudi cells will be used as targets since they are human lymphoma cells that express similar numbers of CD19 and CD22 receptors (e.g., about 20,000 to 40,000). The cell cultures will contain added thymidine as protection against the potential toxicity of the internalized MTX dimer. Kd's for the DHFR$^2$-scFv nanorings will be determined for each of the di-, tetra- and octavalent scFv nanorings and compared to the DHFR$^2$-scFvCD19 and DHFR$^2$-scFvCD22 monomers, as well at the control parental antibodies, anti-CD19 HD37 and anti-CD22 RFB4. Comparing the binding constants generated in these studies will tell whether oligomerization has reduced or enhanced binding affinity relative to the parental antibodies and DHFR$^2$-scFv monomers.

Antibody-nanoring binding will also be evaluated by flow cytometry. DHFR$^2$-scFv's that have been assembled with the Alexa Fluor 488 MTX dimer, 15, will be prepared and incubated with the Daudi cell line for 30 mins at 4° C. Cells treated with the each of the six anti-CD19 and anti-CD22 DHFR$^2$-scFv's nanorings induced by 13 will be analyzed on a FACSCalibur with CellQuest Software (BD Biosciences, Mountain View, Calif.). Data will be expressed in standard histogram form showing cells verses increasing fluorescent intensity. The results will be compared to those for a control FITC-anti-CD7, the FITC labeled parental antibodies and FITC labeled DHFR$^2$-scFv monomers. E. coli DHFR can be efficiently FITC labeled (100%, 3 hr) at cysteine-108 without loss of binding affinity, activity or the ability to be dimerized by MTX$^2$. Therefore, FITC labeling of DHFR$^2$-scFv monomers prior to nanoring assembly should be straightforward.

Based on the results of the binding experiments, if binding has been enhanced or is unchanged compared to the parental antibodies, we will proceed to prepare oligomers of the DHFR$^2$-scFv's assembled with the drug conjugates, 17 and 18, and characterize them as outlined herein.

11.e. Determine the Ability of the Anti-CD19 and Anti-CD22 sFv Nanorings to be Internalized by B-Leukemia Cells Understanding the trafficking of immunoconjugates is important to being able to predict biological activity. The efficacy of internalization for the tightest binding DHFR$^2$-scFv nanorings and their organelle association will be determined. Daudi cells will be incubated with saturating amounts of DHFR$^2$-scFv nanorings that have been assembled with either MTX$^2$-C9 or the fluorescent conjugates 15 or 16, or the drug conjugates 17 and 18. At various time points, cells will be stained with mouse anti-FLAG IgG-FITC and analyzed by flow cytometry to detect the remaining level of surface bound nanorings. A progressive lose in the amount of surface fluorescence will be consistent with cellular uptake. In addition, the surface bound levels for antibody assemblies containing Alexa Fluor 488 conjugates 15 and 16 will also be monitored. Since the chemical dimerizer can dissociate from the complex when not bound to two DHFRs simultaneously, the rapid lose of Alexa Fluor 488 fluorescence relative to anti-FLAG-FITC fluorescence, would indicate cell surface nanoring instability. However, if the degree of cell surface nanoring lose is similar, then the antibody nanorings are likely internalized intact.

To further verify this and to gain insight into the internalization mechanism, Daudi cells will be incubated with the previously mentioned antibody nanorings at various time points, fixed and permeabilized to allow cellular localization to be determined by indirect fluorescence microscopy. Antibodies against the lysosomal marker Lamp-1/CD107a and the Golgi marker GM120 will be used to examine potential co-localization to these organelles, while mouse anti-FLAG will be used to detect the antibody nanorings. The possible importance of endocytosis by clathrin-coated pits or lipid raft pathways will be addressed with antibodies against the clathrin heavy chain or caveolin-1, respectively. Two possible results of microscopic analysis of localized fluorescence signals are likely to be observed. First, the signals could be well segregated and non-overlapping, indicating that the antibody nanorings are not efficiently internalized. Second, co-localization with Lamp-1, the clathrin heavy chain and/or caveolin-1 would be consistent with cellular internalization by endocytosis and trafficking to the lysosomal compartment. In addition, the loss with time of Alexa Fluor 488 fluorescence as well as co-localization with Lamp-1 will demonstrate that the protease sensitive linker is a substrate for cathepsin B. Thus drug delivery by this mechanism is likely. Redesign of this linker may be necessary if lose of fluorescence and therefore cleavage is not observed.

111 The In Vitro Cytotoxicity of the Anti-CD19 and Anti-CD22 sFv Nanorings to B-Leukemia Cells Tumor cells will be evaluated for their sensitivity to the DHFR$^2$-scFv-Doxorubicin and DHFR$^2$-scFv's-Auristatin nanorings. The sensitivity of Daudi cells to a 2 hr incubation with doxorubicin ($IC_{50}$=225±35 nm) and auristatin ($IC_{50}$=4.6±4.3 nm) has already been established. To evaluate the potency of the antibody-drug nanorings, cells will be incubated for 2 hr, washed to remove unbound antibody-drug conjugate. The cells will be replated in fresh media, incubated for 96 hr and the cell viability assessed with Alamar Blue. To assess the role of the MTX dimer on cell viability, a parallel set of experiments will be carried out with media supplemented with thymidine. Control experiments will be conducted with antibody nanorings assembled with deprotected 11, which only bears the protease cleavable linker. $IC_{50}$ values will be determined by plotting the percent cell viability relative to a non-treated control verses antibody-drug nanoring concentration.

To determine the mechanism of cellular toxicity induced by the antibody-drug nanorings, the degree of apoptosis and cell death will be determined by surface Annexin V binding and loss of PI exclusion, respectively. At 24 hr post drug exposure, the cells will be removed from culture and stained with Annexin V-FITC and PI. The amount of apoptotic cells (Annexin $V^+/PI^-$) and of dead cells (Annexin $V^+/PI^-$) will be determined by flow cytometric analysis of the each cell population. As was the case for cellular toxicity, drug conjugated and non-drug conjugated antibody nanorings will be compared.

To further probe the mechanism of toxicity, the effect on the antibody-drug nanorings on the cell cycle will be assessed by treating the cells as described above. However, shortly before harvesting the cultures will be treated with bomodeoxyuridine (BrdU) for 20 min. The cells will be fixed, permeabilized and the amount of nascent DNA synthesis determined by anti-BrdU-FITC, followed by staining with PI for total DNA content. Previously, doxorubicin antibody conjugates have been shown to produce either potent $G_2$ arrest or to have little effect, while auristatin antibody conjugates have been shown to potently induce $G_2$-M phase arrest. Since the degree of toxicity is highly dependent on the targeting antibody and the induced cellular trafficking, we cannot predict at this time what result is likely to be observed. Again, the effect of drug conjugated and non-drug conjugated antibody nanorings will be compared.

11.g. The In Vivo Pharmacokinetics and Biodistribution of the Anti-CD 19 and Anti-CD22 sFv Nanorings To measure pharmacokinetics/biodistribution, the most potent $DHFR^2$-scFv-drug nanorings will be injected into groups of mice and pharmacokinetics determined by ELISA with anti-FLAG-HRP by serial blood measurements and 1-125 labeling. Linear compartment models will be fit to data to estimate pharmacokinetic parameters, such as $t_{1/2}$, AUC, $Vd_{ss}$, Cl, MRT. SAS nonlinear regression program (PROC NLIN) and SIPHAR program will be used for computer modeling. Tissue and organ doses for the nanorings will be computed using biodistribution data for tumor and normal tissues over time. In all studies, $DHFR^2$-scFv fusion proteins and $DHFR^2$-scFV nanorings assembled with $MTX^2$-C9 will be studied as controls so we can determine the effect on scFv oligomerization and drug loading on the clearance. Free drug plasma concentrations will be determined by HPLC by monitoring the MTX fluorescence. Correlation of the amount of nanoring dosed with the amount of free drug-$MTX^2$ will assess nanoring stability in vivo. The half-life of *E. coli* DHFR and *E. coli* DHFR bound to MTX in 80% mouse and human plasma at 37° C. is 10 hr and 22 hr, respectively. At 0° C., *E. coli* DHFR was found to be indefinitely stable in both mouse and human plasma. The plasma stability of DHFR is evidently dependent on its intrinsic stability at 37° C. (i.e., unfolded vs. folded states), which the slow off rate of MTX enhances. Although, the nanorings should have a substantially longer half-life, the protein may be further stabilized by site-directed mutagenesis.

The way a targeted protein distributes throughout a tumor indicates if further modifications are necessary. Immunohistochemical studies with anti-FLAG-FITC will be performed to determine how the antibody-drug nanorings distribute throughout tumors. Some antibodies distribute homogeneously and some bind to the first wall of antigen that they encounter after diffusion from the blood into the parenchyma. This data will be used to correlate affinity to the quality of tumor penetration. If the data reveal that the antibody is distributed homogenously throughout the tumor, the affinity of the antibody nanorings is sufficient.

11.h. The In Vivo Toxicity of the Anti-CD19 and Anti-CD22 sFv Nanorings

Biological evaluation will begin by determining the side effects in animals prior to determining their anti-tumor potency. Animals will be given a dose exceeding the maximum tolerated dose (MTD) determined by injecting groups of mice with the antibody-drug nanorings until lethality is observed.

In the liver, damage can be accurately quantitated and significance determined using histology analysis plus a functional assay that measures increases in the liver enzyme, alanine transferase (ALT). ALT values of groups of mice (n=10/group) can be averaged to determine if variances differ significantly by Student t test. Histology damage to the liver usually is the form of necrosis, mononuclear cell infiltration, and even formation of fatty vacuolization. Past studies have shown a direct correlation between functional data and histology findings.

For renal toxicity studies, the same strategy can be used as described for the liver. Histology studies are combined with a functional assay. In this case the assay is assessment of Blood Urea Nitrogen (BUN) levels and an additional and independent test for creatinine. Both tests serve as indicators of renal injury. Groups of mice (n=10/group) are treated with drug and compared to mice given PBS. All results are verified by histologic analysis since there is a direct correlation between the functional damage and histologic findings. Examination of tissues in a mouse with kidney impairment usually reveals damage to the proximal or distal tubules, and glomeruli. Histology testing will also include other organ systems such as the GI tract, heart, brain, lung, and stomach.

Vascular toxicity will also be assessed. However, these measurements can be complex in rodents and are sometimes misleading. Therefore, several measurements based on different assays will be included. Histology combined with a system developed by Baluna and Vitetta will be used to assess vascular leak. In this model, a combination of wet/dry tissue ratios and dye tests are used assess VLS. To perform the tests, C57BL/6 mice, 6-10 weeks old, are injected and at various time periods, the lungs are removed and analyzed for fluid accumulation and leak into the interstitium as follows.

A shift in fluid content signifying VLS can be detected by determining wet/dry tissue ratios. Punch biopsies are obtained from mouse skin. Both skin and lungs are recovered from the treated mice for the measurement of water content. The organs are weighed, frozen at −80 C., and then freeze-dried. The water content of the organs is calculated as the wet/dry weight ratio. Data is averaged for groups of 5 mice. Baluna and Vitetta clearly demonstrated a consistent increase in the fluid content of the grafts from immunotoxin treated versus control mice and the magnitude of the changes in wet/dry weight ratios were comparable to other murine models of vascular leak induced by IL-2 or LPS.

Histologic assessment will also be used as a direct means of assessing vascular damage and will be carried out. The histologic effect of the antibody-drug nanorings on endothelial cells lining large vessels of target organs will assessed. Evidence of red blood cell infiltration in the sinuses of blood-filtering organs such as liver will be determined. Vessel morphology, leukocyte infiltration, and interstitial edema will also be evaluated.

Bone marrow effects will be addressed by taking mice treated with the anti-tumor nanorings and then removing the two femurs. Bone marrow will be removed from one of the femurs by standard bone marrow processing techniques and the number of mononuclear cells that still remain within the marrow will be calculated. Data will be reported on cell/femur basis. By comparing groups of mice given drug to groups of mice that are untreated, whether therapy has induced a hypocellularity will be determined. The extent of the suppression and the nature of the cells affected will be determined by analyzing the histology of the other femur.

Taken together, these toxicity studies as a whole will be used to anticipate the toxicities that might be observed in a phase 1 clinical study. Statistical comparisons mostly in the form of Student t tests will tell us if these differences are indeed meaningful.

11.i. The In Vivo Antitumor Potency of the Anti-CD19 and Anti-CD22 sFv Nanorings Efficacy studies are another goal for the development of an anti-leukemia drug. A therapeutic index (TI) for the most potent antibody-drug nanorings will be determined and then a dose for therapy studies will be selected. The purpose of finding the TI is the selection of a "safe" dose since the TI is the range of safe doses that are between the MTD dose and the dose that will give an anti-tumor response without toxicity. Based on previously reported studies we expect this to be somewhere between 3 and 6 mg/kg. The dosing schedule will be determined after the pharmacokinetic parameter for the nanoring is established. Once this dosage is established then efficacy studies will be conducted.

For the efficacy studies, an aggressive CD19+CD22+ hematopoietic tumor in Daudi will be used that can be used in two different models that gives different information. The first model permits the assessment of the ability of the anti-body-drug nanorings to penetrate into large primary tumors on the flank. Because it is possible to measure the growth of the tumor with calipers, the daily drug's effect on the size of the tumor can be determined. The primary tumor will eventually kill the mouse unless the experiment is terminated.

The best dose and a safe maintenance dose schedule will be determined that will prevent relapse. The dose will be increased until a dose that causes tumor regression is found. Then a maintenance regimen will be developed. Since a weight loss of more than 25% of the total mouse body weight over two days results in death, weight loss will be used to monitor toxicity and develop safe maintenance regimens. To determine the effect against larger tumors, we will simply wait longer to begin treatment after the initial tumor dose in the flank and then test the effect of giving multiple doses to large tumors that exceed 1 cm$^3$ in volume.

Because route of inoculation can impact tumor growth, the effects of ip verses iv dosing will be determined. In addition, since direct injection creates spikes of concentration that peak and ebb quickly, the use of pump delivery will also be explored, e.g., using the micro-osmotic pump model 1007D (Durect Corp, Cupertino, Calif.). This pump allowed 0.5 µl per hour to be administered over 7 days.

One important question is whether relapsing tumors express CD19, CD22, or both. In order to investigate this issue, flank tumors will be removed from animals that originally underwent a complete clinical regression and subsequent relapse. The tumor cells will be isolated by standard protocols and tested with fluorochrome labeled anti-CD19 and anti-CD22 antibodies by flow cytometry. The data will be used to determine whether it will be important to combine the antibody-drug nanorings with other treatment modalities such as chemotherapeutic agents as has been done in other combination studies involving anti-CD19 and anti-CD22 immunotoxins. For example, if relapsing tumors do not express CD19 and CD22, it will be important to look at other modalities to combine to enhance the effect. Several additional logs of tumor kill have been gained by adding cytoxan or camptothectin.

Lastly, a second in vivo animal model will be used that measures the effect of the antibody-drug nanorings on the systemic spread of tumor since it propagates in vivo more like a human hematopoietic malignancy. The last stage of the disease is hind limb paralysis indicating that the tumor has entered the CNS. The growth of tumor in mice in this manner is unique to scid. To infect scid mice, Daudi will be injected intravenously. Animals typically die between 30-40 days and histology shows that the tumor metastasizes into all major organs.

EXAMPLE 12

DHFR$^2$-MTX$^2$ Heterodimer Building Blocks for Co-Polymeric Nanoring Assembly

The development of DHFR$^2$-MTX$^2$'s assembled from heterodimeric monomers will provide a means to prepare bispecific multivalent antibody nanorings. The ability of charge complementary double mutants at Ala-19 and Gln-23 to enforce chemically induced DHFR heterodimerization will be examined. Based on computer modeling analysis, these two residues are the mostly likely to facilitate side chain high pairing by the protein interface. Double mutants; Lys-19-Lys-23, Arg-19-Arg-23, Lys-19-Arg-23, Arg-19-Lys-23, Asp-19-Asp-23, Glu-19-Glu-23, Asp-19-Glu-23 and Glu-19-Asp-19 will be prepared. The ability of each to dimerize in the presence of MTX$^2$-C9 will be determined, as well as the ability of the "positively" charged mutants to heterodimerize with the "negatively" charged mutants.

12. a. Construction of Double Mutants.

To enable the characterization of both homo and heterodimeric pairs of DHFR, mutants will be prepared from a plasmid encoding the expression of a DHFR green fluorescence protein (GFP) fusion protein. Because the molecular weight of GFP is approximately 30 kDa, unique dimer species will be resolvable by SEC when a mutant DHFR-GFP is paired with a complementary mutant DHFR. The expression plasmid, p13DGFP will be constructed by amplifying the GFP gene from and in house plasmid, pMSCV-MIGR1-IRES-eGFP, with primers encoding the XhoI and XbaI restriction sites. Both pF13DD and the GFP PCR product will be digested, the products purified and ligated. The double mutants, Lys-19-Lys-23, Arg-19-Arg-23, Lys-19-Arg-23, Arg-19-Lys-23, Asp-19-Asp-23, Glu-19-Glu-23, Asp-19-Glu-23 and Glu-19-Asp-19 of DHFR-GFP will be obtained in one step by Quick Change™ Mutagenesis. The same mutants will of DHFR will also be prepared with the expression plasmid, p-TZ. Primers will be designed that are sufficiently long enough to insert both mutations simultaneously.

12. b. Analysis of Mutant Dimerization

Characterization of mutant dimerization will be carried by SEC as outlined herein. Unique values for $K_{eq}/K_c$ can be obtained from MTX competitive DHFR$^2$ disassembly experiments. Since the relative free energy of binding ($\Delta\Delta G$) for one monomer to another is proportional to the ratio of the $K_c$(wt)/$K_c$(mutant) and the value of $K_{eq}$ is non-dependent value, the $\Delta\Delta G$ for binding can be calculated from the following equation.

$$\Delta\Delta G = -RT \cdot \ln(K_{eq}/K_c \text{mut}) - (-RT \cdot \ln(K_{eq}/K_c \text{wt}))$$

Consequently, the impact of the mutations will be determined on protein-protein interface thermodynamics by comparing the $K_{eq}/K_c$ for each mutant to the value for wild-type. Typically, DHFR dimers will be pre-equilibrated (3+ hours) in GP500 buffer and mixed with increasing concentrations of monomeric MTX. Samples will be incubated for 48 hours after the addition of MTX, then assayed by SEC as described above. Data will be fit to equation 3 with Mathematica (Wolfram Research), with manual optimization to obtain the best fit, $R^2=0.998$.

$$[E_2 D^*_{active}] = \frac{K_c K_{a1} K_{a2}(0.5 - [E_2 D^*_{active}])(1 - 2[E_2 D^*_{active}])^2}{K_{eq} K^2_{aMTX}(M_t - E_t + 2[E_2 D^*_{active}])^2}$$

12. c. Analysis of Mutant Heterodimerization with Fluorescently Labeled DHFR's

The ability of the "positively" charged mutants Arg-19-Arg-23, Lys-19-Arg-23 or Arg-19-Lys-23 to form heterodimers with the "negatively" charged mutants, Asp-19-Asp-23, Glu-19-Glu-23, Asp-19-Glu-23 and Glu-19-Asp-19 will be determined by SEC as outline above. A positively charged mutant DHFR will be mixed with a negatively charged mutant DHFR-GFP, the solution allowed to reach equilibrium and the amount of homodimer and heterodimer determined. The complementary pairs will be ranked based on their ability to form 100% heterodimers at a $MTX^2$-C9 to protein ratio of 0.5:1.0. The relative free energy of binding will be determined for heterodimers meeting this criteria by competitive $DHFR^2$ disassembly with MTX as described above.

12. d. Computer Modeling of Homo and Heterodimerization

Despite the importance to understanding how proteins interact with one another, the development of effective ways of modeling protein-protein interfaces is still in its infancy. One of the major hurdles has been the inability to study structurally well-characterized systems in which the free energies of binding can be accurately determined for relatively weak (3-5 kcal/mol) sets of interactions. Even if this were the case, the modeler must still develop methods that will not result in the two proteins simply dissociating from one another, particular in explicit water. $DHFR^2$-$MTX^2$ provides an excellent system to develop approaches to modeling protein-protein interactions since; 1) high resolution structures of $DHFR^2$-$MTX^2$ complexes have been and will be determined, 2) free energy of binding calculations can be validated by competition binding experiments, and 3) the individual monomers are tether together by the bivalent MTX with a picomolar dissociation constant.

Two methods will be implemented in order to estimate the stability of DHFR protein-protein interactions: calculating relative free energies of binding for wild-type and mutant DHFR dimers by means of molecular dynamics (MD) simulations followed by Poisson-Boltzmann continuum electrostatics; and calculating relative complexation energies of those dimers using MD followed by molecular mechanics (MM) minimizations. In both methods, each MD simulation will run for 1-3 ns in 1 fs increments, at constant pressure and volume with temperature ramped from 100 K to an approximately physiological 310 K. All MD calculations will be done using CHARMm version c31b1 in the InsightII molecular modeling environment, with explicit solvent (modified TIP3P water model[110]), a periodic box of 70×70×95 Å, and a van der Waals cutoff of 10 Å. Neutral charge will be obtained by placement of $Na^+$ counterions, and dielectrics will be treated by particle-mesh Ewald summation. The lowest-energy conformation will be extracted from each trajectory for further calculations. Relative Free Energies of Binding. The binding free energy $DG_{bind}$ for each DHFR dimer is defined as $$\Delta G_{bind} = \Delta G_{ab} - \Delta G_a - \Delta G_b$$

where $DG_{ab}$, $DG_a$, and $DG_b$ respectively correspond to the electrostatic solvation free energies of the dimer and each individual monomer. Electrostatic free energies for the dimer and monomers will be determined by the method of Roux et al., in which the Poisson-Boltzmann equation is solved numerically for the lowest-energy conformation of DHFR (wild-type and mutant) with a van der Waals radius of 25 Å. Relative Complexation Energies. The relative complexation energy $E_{compl}$ for each DHFR dimer is defined as $$E_{compl} = E_{ab} - E_a - E_b$$

where $E_{ab}$, $E_a$, and $E_b$ respectively refer to the molecular mechanics (MM) energies of the dimer and each individual monomer. A major advantage of this approach is that differences in entropy and solvation terms can be assumed to cancel out for structurally related compounds, which contributes to the accuracy of the calculated energies. A three-stage minimization process will be implemented in CHARMm in order to avoid unnatural or strained molecular conformations: first, the entire system is held rigid except for the hydrogens; second, only the sidechains are permitted to relax; and finally the entire structure is optimized. The TIP3P water model will be used for purposes of consistency. Each minimization will employ steepest descents to an energy change convergence criterion of 100 kcal/mol per iteration, and conjugate gradients (Polak-Ribiere[114]) thereafter until a convergence is reached at 0.001 kcal/mol per iteration.

The relative free energy of binding calculated from modeling experiments will be compared to the experimentally determined values. The modeling strategy will then either be validated or will be further modified to accommodate discrepancies. These methods will be applicable to the further engineering of the protein interface to create additional heterodimeric pairs, thus expanding the range of potential co-polymeric scFV-nanorings.

12. e. X-Ray Structure Analysis of Homo and Heterodimerized DHFRs

To fully characterize the molecular interactions necessary for heterodimer protein-protein interface design and to validate our modeling strategy, the structure of the monomer-monomer side-chain interactions will be determined. The x-ray crystal structures of the dimerized mutant DHFR's will be determined

EXAMPLE 13

Methotrexate Dimmer Conjugates to a Fluorescent Probe and an Anti-Tubulin Drug $MTX^2$ dimerizer—Alexa Fluor 488 conjugates will be prepared that allow the monitoring of anti-IGF1R nanoring interactions with breast cancer cells by FACS and fluorescence 1 microscopy. $MTX^2$ dimerizer—auristatin conjugates will be prepared, which will be used to assemble anti-IGF1R nanorings for the delivery of auristatin.

Based on x-ray structure analysis of DHFR dimerized by $MTX^2$, the linker remains flexible and does not interact with the protein. Consequently, MTX dimers that contain an additional linker emanating from a central amino group should provide a route to the construction of tri-functional protein dimerizer. The design of the tri-functional MTX dimerizers incorporates a number of important features. First, an 11 atom polyamine linker will be used to connect to two MTXs. This should be of sufficient length, since no significant difference in the dimerization of DHFR by MTX dimers containing from 9-18 atoms has been observed. Second, to improve water solubility and reduce possible ligand-ligand induced nanoring aggregation, the third linker will be a polyethylene glycol (PEG) chain. Next, a lysosomal protease sensitive spacer will be appended that upon cell uptake will release the drug. Senter and coworkers have recently shown that immunoconjugates incorporating the cathepsin B cleavable valine and citruline based linkers are highly stable in mouse plasma and potent anticancer agents, both in vitro and in vivo.

Auristatin is a member of the dolastatin family of natural products with potent anticancer activity. Like taxol, auristatin is an inhibitor of tubulin polymerization and may also cause damage to the vasculature of solid tumors. Auristatin is broadly active in vitro ($IC_{50}$=3.2±0.51 nm against 39 human tumor cell lines, including breast cancers), but lacks sufficient clinical efficacy. To enhance the efficacy of auristatin, Mab conjugates have been prepared and shown to be potent and selective anticancer agents in vitro and in vivo. In particular, the growth of breast cancer cell lines that express the Le(Y) antigen can be inhibited by anti-Le(Y) conjugates to auristatin.

Involved in the synthesis of the $MTX^2$-conjugates will be the preparation of the trivalent linkers, 4 and 5. (Scheme 7) Based on the methodologies of Parker et. al. for the synthesis of linear and cyclic triamines, we will prepare the trimethylsilyl-ethanesulfoamide SES protected bis-cyanobutylamine, 2, from 5-bromovaleronitrile and SES-$NH_2$ in the presence of cesium carbonate. After reduction of the cyano groups with boran-THF, the amines will be protected by treatment with carbobenzyloxy chloride (CBZ-Cl), and the SES protecting group removed with cesium fluoride. The third arm of the trivalent linker will be installed by alkylation with PEG5 and PEG6-NHBoc bromides, yielding 4 and 5. Removal of the Cbz groups by hydrogenation will yield the appropriate differentially protected tetramines (6 and 7). Next, the silyl-protected glutamate will be coupled to 6 and 7 in the presence of EDC and HOBT, followed by removal of the Cbz groups by catalytic hydrogention. Compound 6 will be prepared by DEPC assisted coupling of MTX to the free amine, followed by removal of the Boc group. The valine citruline p-aminobenzyloxycarbonyl (PABOH) cathepsin B sensitive peptide spacer will be prepared as previously described and coupled to compounds 8 and 9 in the presence of DIEA (26B). Alexa-Fluor cadaverine and auristatin will be coupled to the free PABOH hydroxyl group by treatment with p-nitrophenyl chloroformate in pyridine. The final products, 10-13, will be obtained after removal of the silyl groups with TBAF. The structure and purity of 10-13 will be verified by NMR and LC-MS analysis.

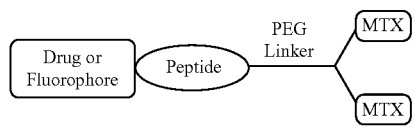

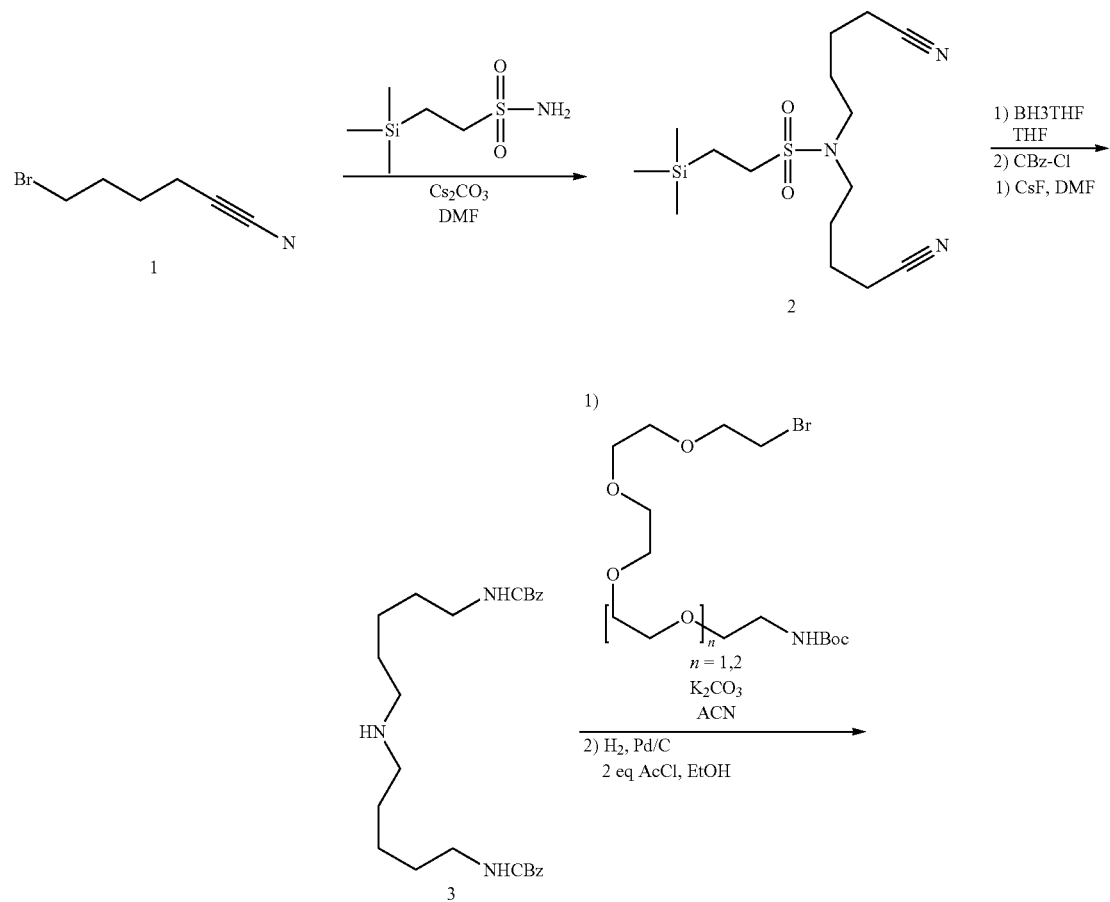

-continued
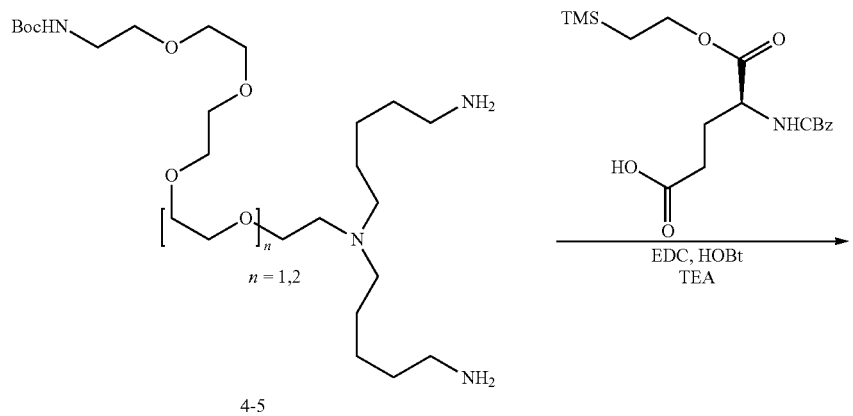
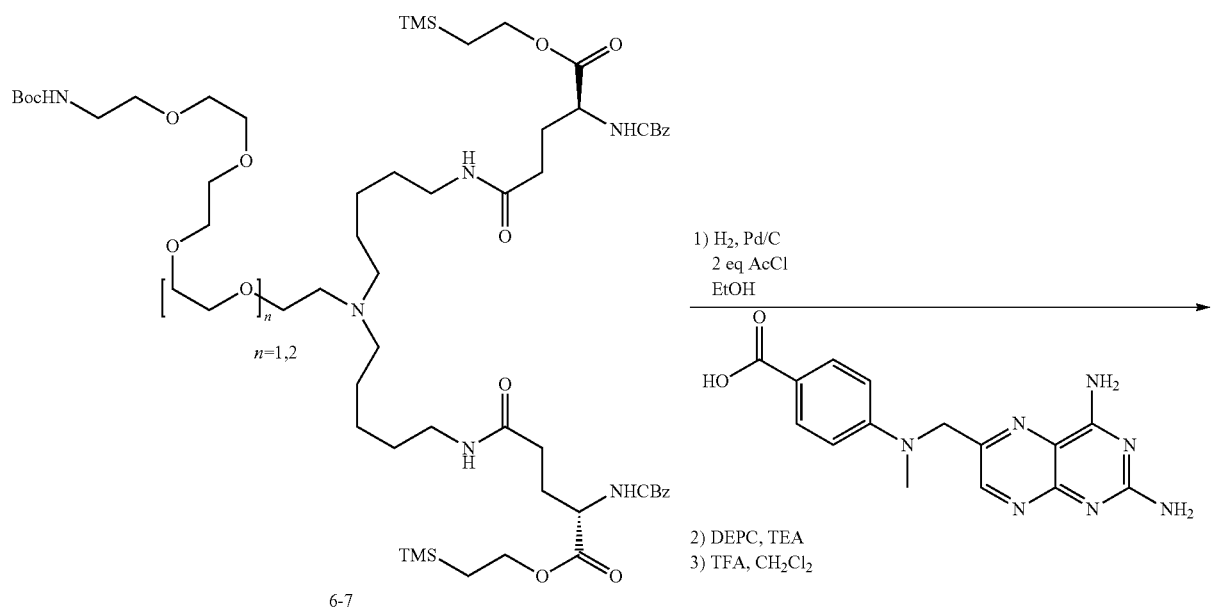
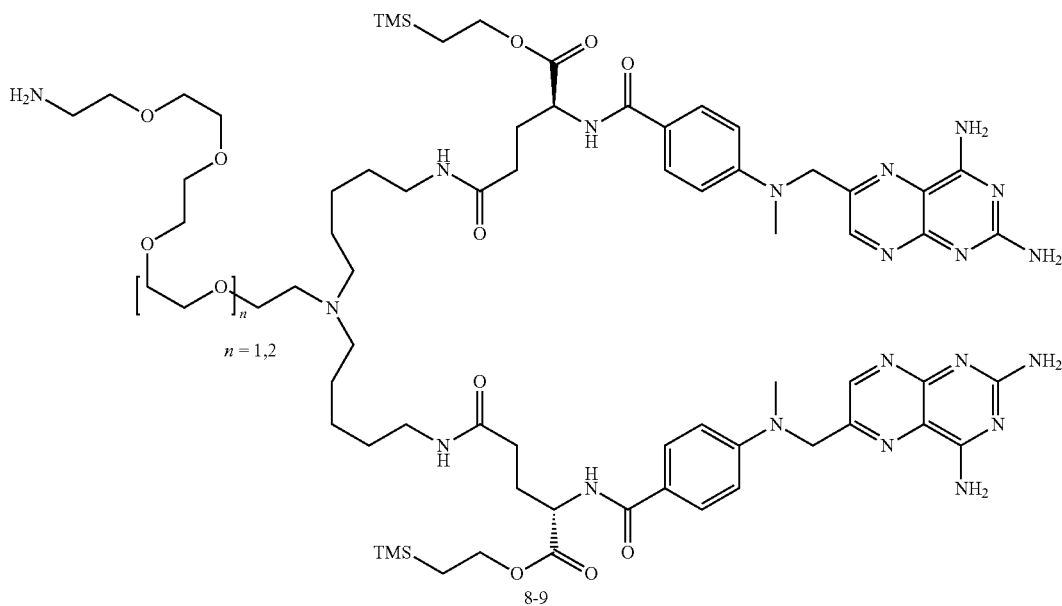

-continued
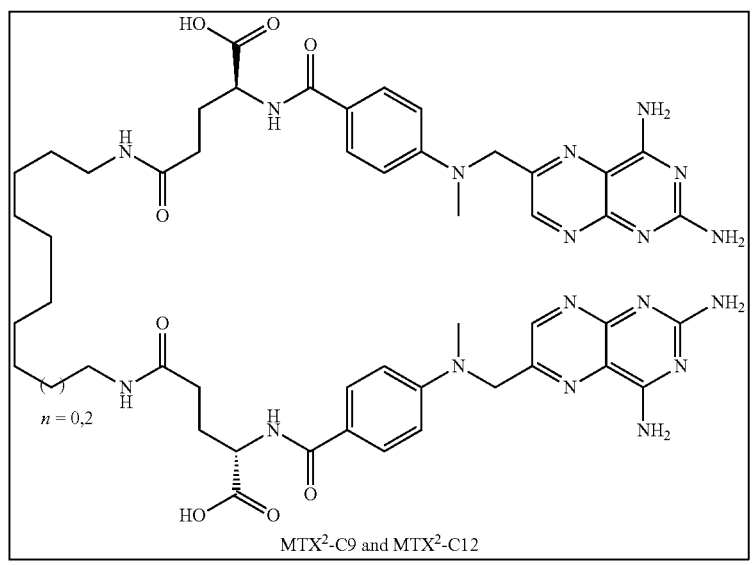
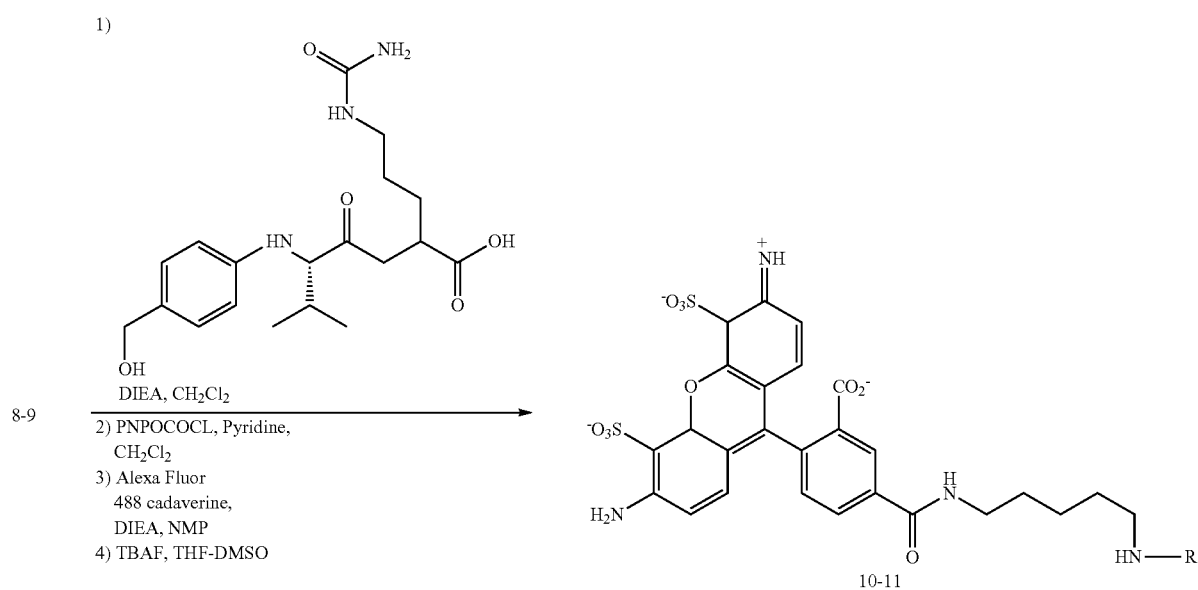
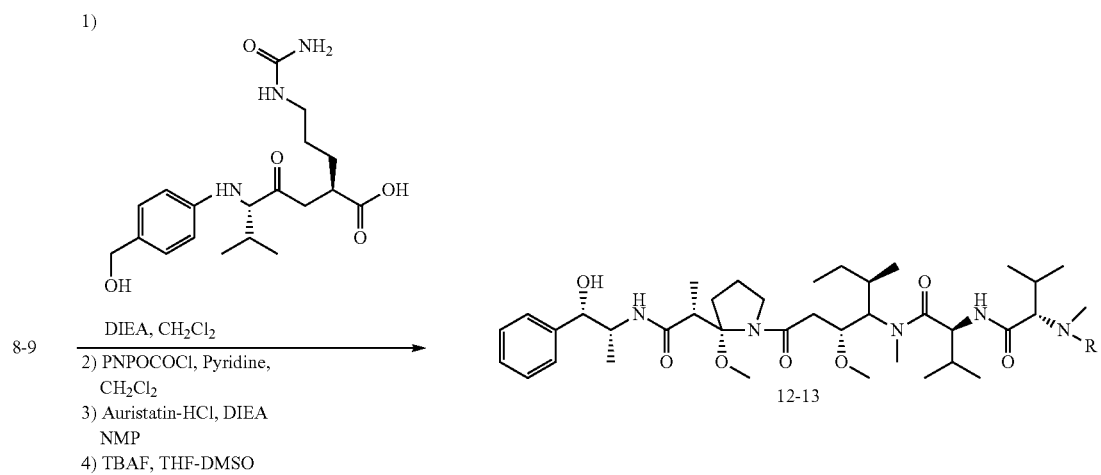

-continued

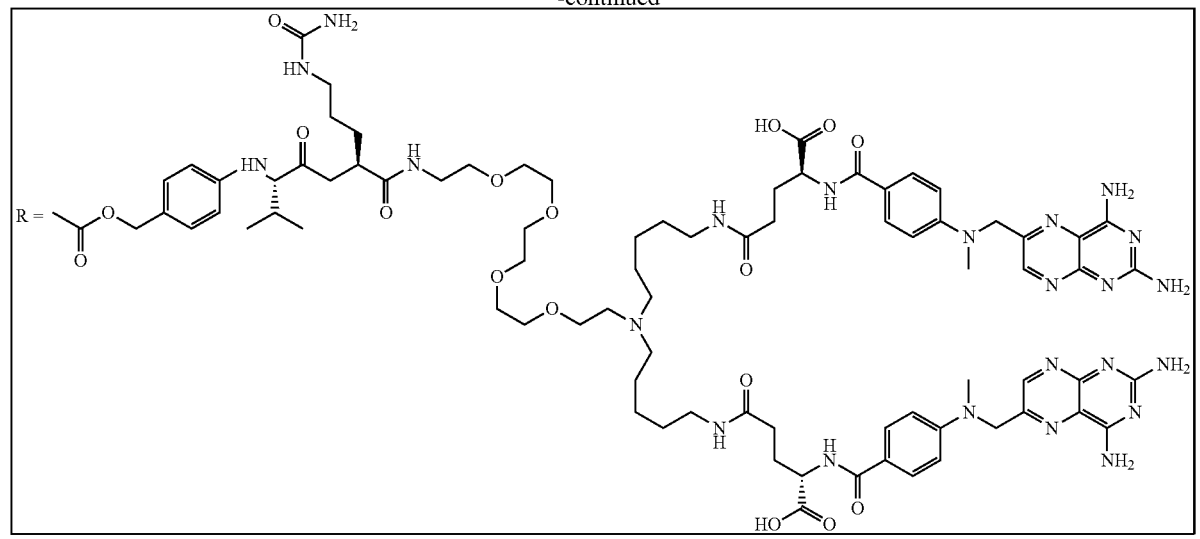

EXAMPLE 14

IGF1R scFv Nanorings Bind to Breast Cancer Cells and Alter Proliferation and Survival Anti-IGF1R scFV-DHFR-DHFR fusion proteins will be prepared that will be assembled into bi-, tetra- and octavalent anti-IGF1R nanoring capable of delivering $MTX^2$, $MTX^2$-Alexa Fluor 488 and $MTX^2$-auristatin to breast cancer cells. Their ability to alter the cell-cycle of breast cancer cells, induce down regulation IGF1R and induce apoptosis will be determined.

Anti-IGF1R scFv-$DHFR^2$ fusion proteins will be prepared that are capable of self-assembling into of di-, tetra- and octavalent anti-IGF1R scFv's when mixed with $MTX^2$-C9 and 10-13. These complexes will be fully characterized, their ability to be internalized assessed and their in vitro and in vivo anti-cancer activity determined.

$DHFR^2$-scFv fusion proteins will be constructed by altering the plasmids that encode the $DHFR^2$ 13 amino acid (pF13DD), 3 amino acid (pF3DD) and glycine (pF1-GDD) linkers. The stop codon will be removed and a 13 amino acid linker (AGENLYFQ\GIGLD) (SEQ ID NO: 3) inserted between the Xba I site and the end of the $DHFR^2$ gene by Quick Change™ insertion mutagenesis. After amplification of the gene for anti-IGF1R scFv from pcDNA/aIGF-1R scFV with primers containing a 5'-XbaI site and 3'-Sac-I site, the respective PCR products will be double digested, ligated to the respective double digested plasmids, followed by DNA sequence verification. The $DHFR^2$-scFv fusion proteins will be expressed and purified, after refolding, by MTX affinity column chromatography. The ability of the $DHFR^2$-scFv fusion proteins to self-assemble into antibody nanorings will first be assessed with the dimerizer, $MTX^2$-C9, by size-exclusion chromatography, dynamic and static light scattering, and transmission electron microscopy. Antibody-drug nanorings will be prepared with the fluorogenic dimerizers, 10 and 11, and their ability to bind to the human breast cancer cell line, MCF-7, as well as be internalized determined by flow cytometry and fluorescence microscopy (33B, 34B). The possible importance of endocytosis by clathrin-coated pits or lipid raft pathways will be addressed with antibodies against the clathrin heavy chain or caveolin-1, respectively. Next, antibody-drug nanorings prepared with $MTX^2$-C9 and the auristatin dimerizers, 12 and 13, will be evaluated for their ability to inhibit the proliferation of MCF-7 cells. Cells will be plated in 25-well plates and treated in triplicate with the antibody-drug nanorings. Growth will be measured 4-5 days post treatment with the MTT assay (25B). Control studies with anti-IGF1R-DHFR2, with and without MTX and/or auristatin will be carried out simultaneously. To determine the mechanism of cellular toxicity induced by the antibody-drug nanorings, the degree of apoptosis and cell death will be determined by surface Annexin V binding and loss of PI exclusion, respectively (35B). At 24 hr post drug exposure, the cells will be removed from culture and stained with Annexin V-FITC and PI. The amount of apoptotic cells (Annexin $V^+/PI^-$) and of dead cells (Annexin $V^+/PI^-$) will be determined by flow cytometeric analysis of the each cell population. To further probe the mechanism of toxicity, the effect on the antibody-drug nanorings on the cell cycle will be assessed by treating the cells as described above. However, shortly before harvesting the cultures will be treated with bromodeoxyuridine for 20 min. The cells will be fixed, permeabilized and the amount of nascent DNA synthesis determined by anti-BrdU-FITC, followed by staining with PI for total DNA content. Again, the effect of anti-IGF1R-DHFR2, with and without MTX and/or auristatin will be compared to the nanorings. In addition, we will assess the ability of the antibody nanorings to down-regulate IGF1R. MCF-7 cells will be treated with the antibody nanorings or scIGF1R-sc-Fc at various time periods and the amount of IGF1R determined by immunoblot analysis with an antibody to the □-subunit of IGF1R.

EXAMPLE 15

Design and Synthesis of Methotrexate Dimer ($MTX^2$) Conjugates of; a) the Fluorophore, Alexa Fluor 488, and b) the Radiolabeling Chelator, 1B4M-diethylene-triaminepentaaceticacid (DTPA)

Based on x-ray structure analysis of DHFR dimerized by $MTX^2$, the linker remains flexible and does not interact with the protein. Consequently, MTX dimers that contain an additional linker emanating from a central amino group should provide a route to the construction of tri-functional protein dimerizers. $DHFR^2$-scFv nanorings containing the additional cargo molecule can then be assembled. Tri-functional MTX DHFR dimerizers that can serve as; 1) fluorescent probes for cellular uptake studies and 2) delivery vehicles for chelated radionuclide to tumor cells will be produced.

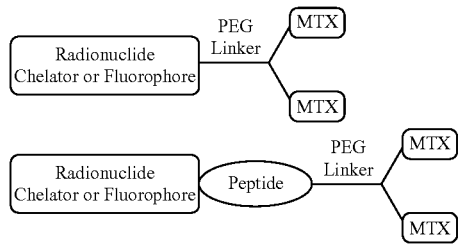

The design of the tri-functional MTX dimerizers incorporates a number of features. First, an 11 atom polyamine linker will be used to connect to two MTXs. This should be of sufficient length, since no significant difference in the dimerization of DHFR by MTX dimers containing from 9-18 atoms has been observed. Second, to improve water solubility and reduce possible ligand-ligand induced nanoring aggregation, the third linker will be a polyethylene glycol (PEG) chain. MTX dimerizers will also be prepared in which a lysosomal protease sensitive spacer has been appended. This will allow for the probing of the mechanism of cellular uptake, as well as the importance of radionuclide release on in vivo labeling.

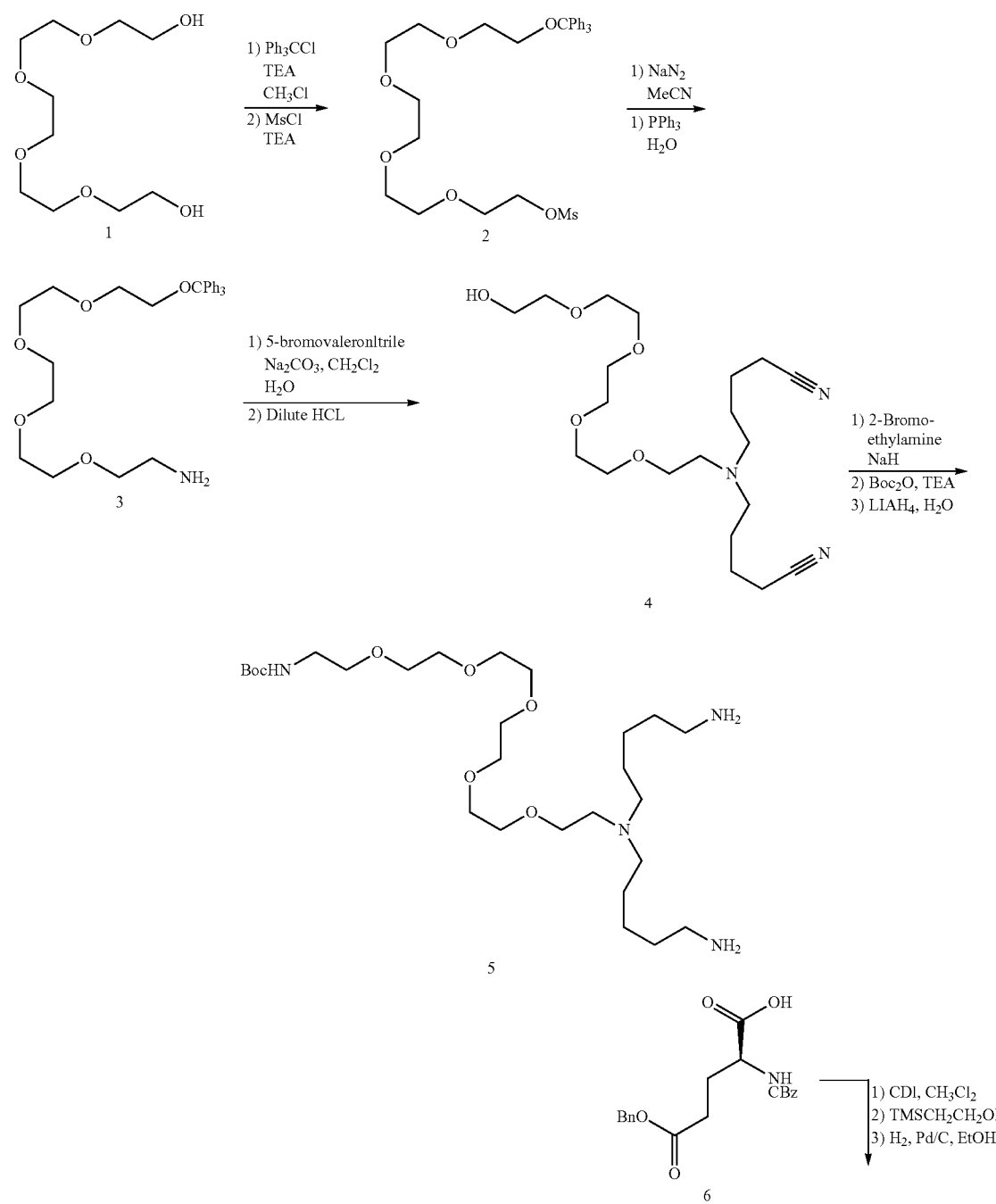

-continued
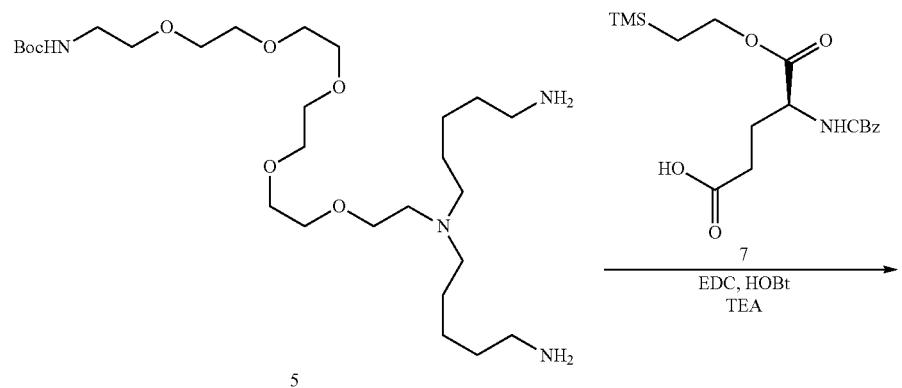
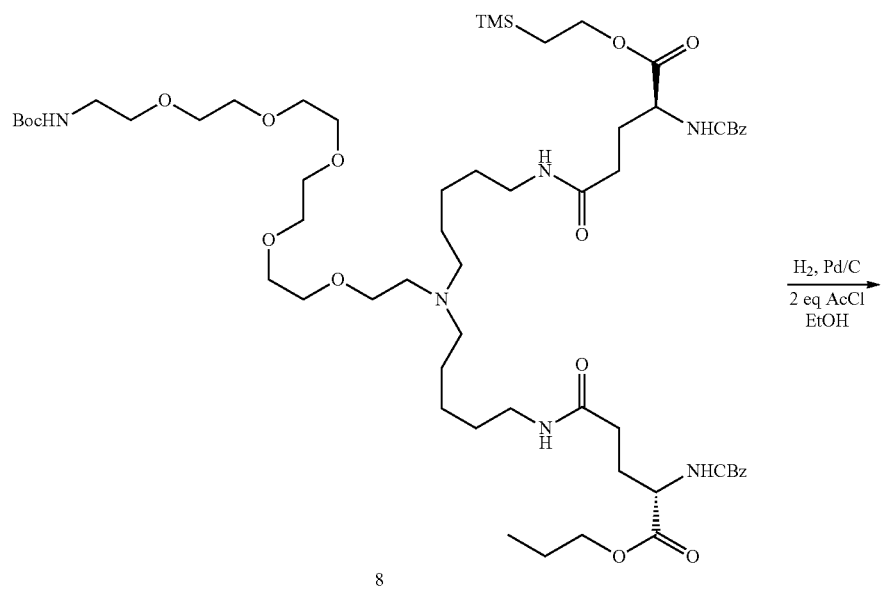
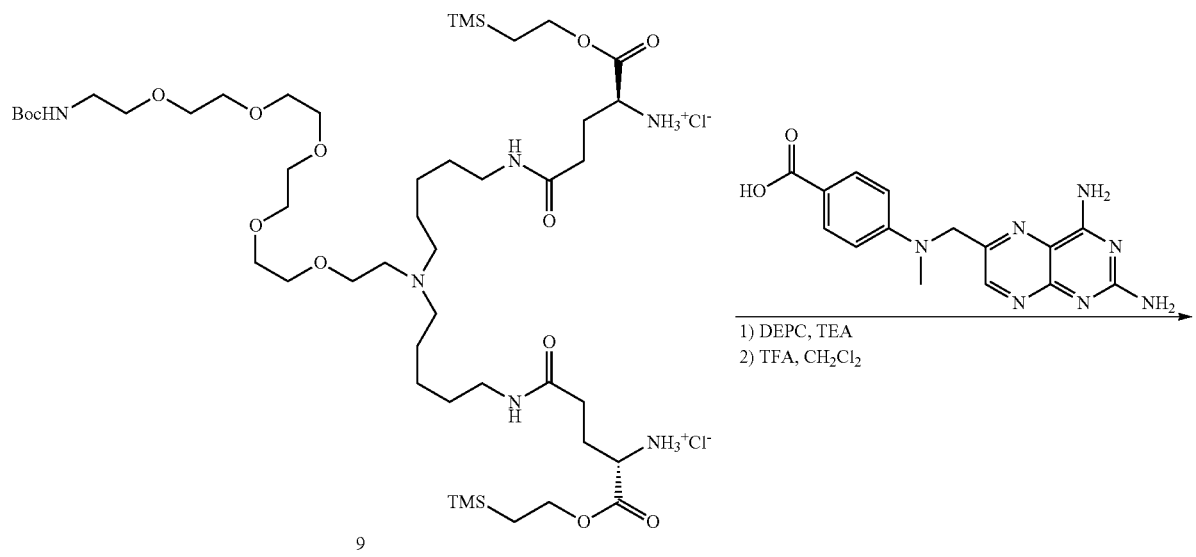

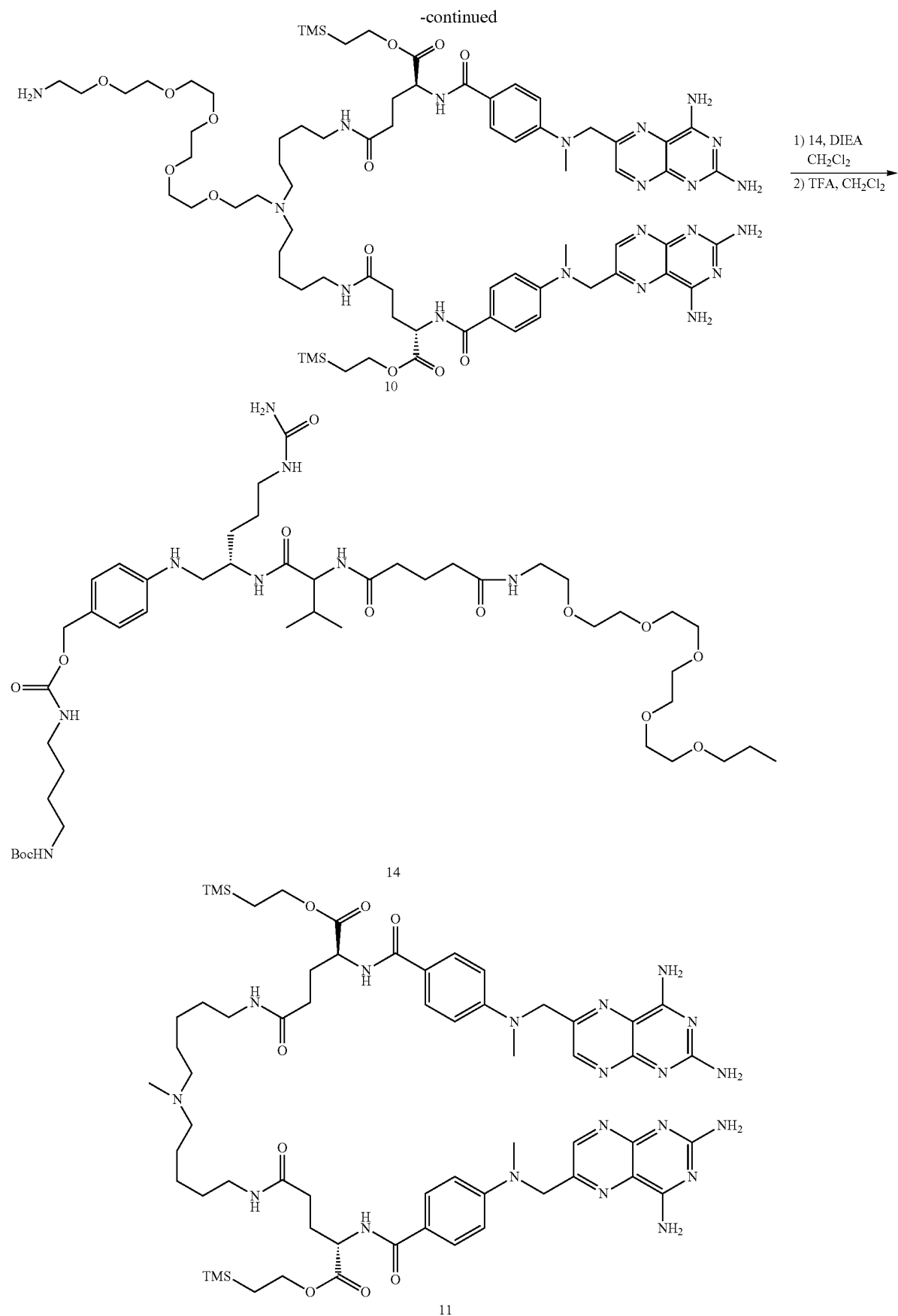

-continued
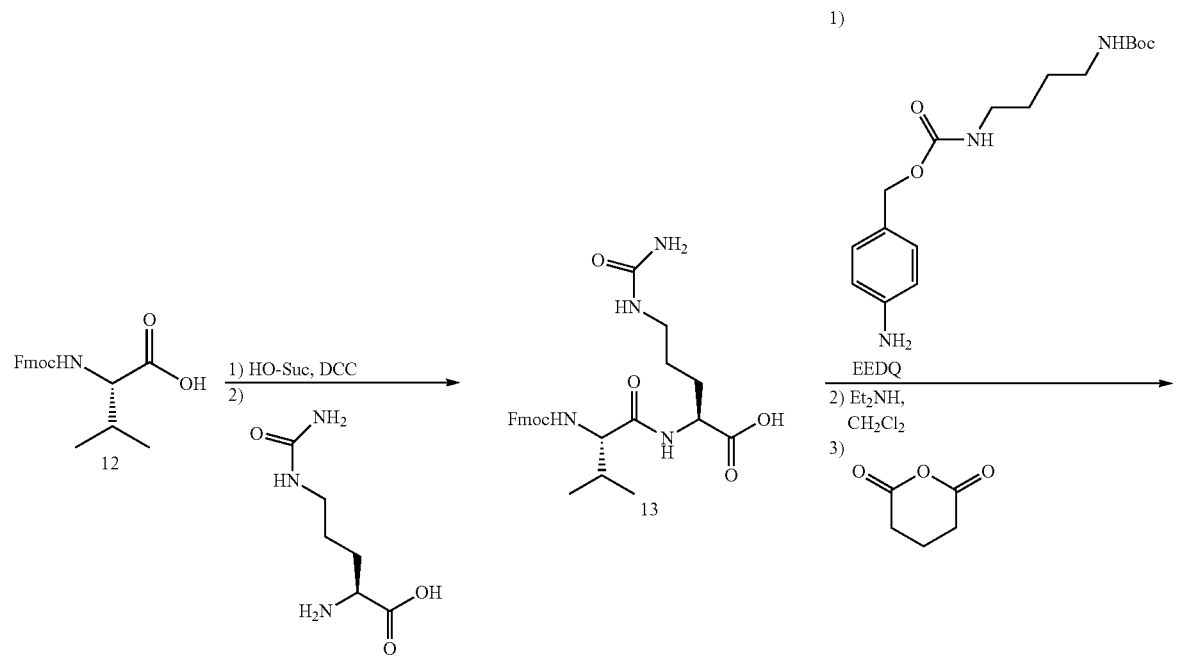
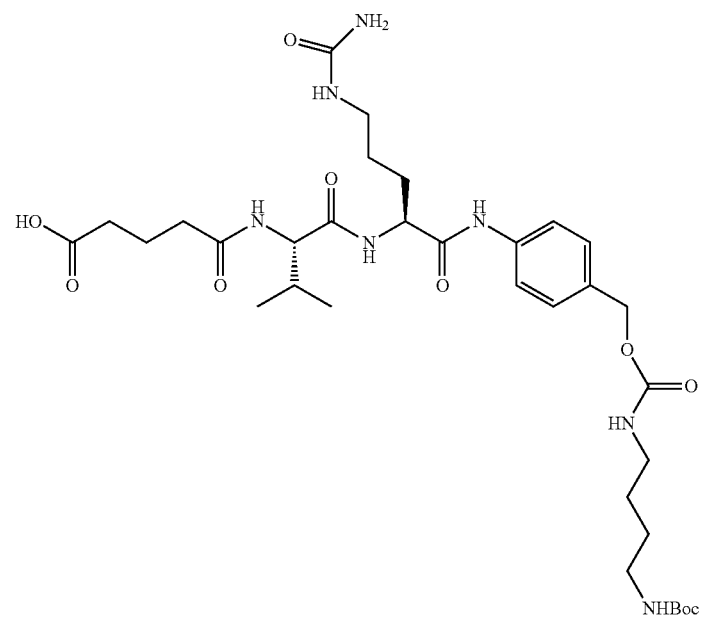

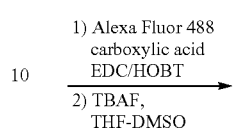
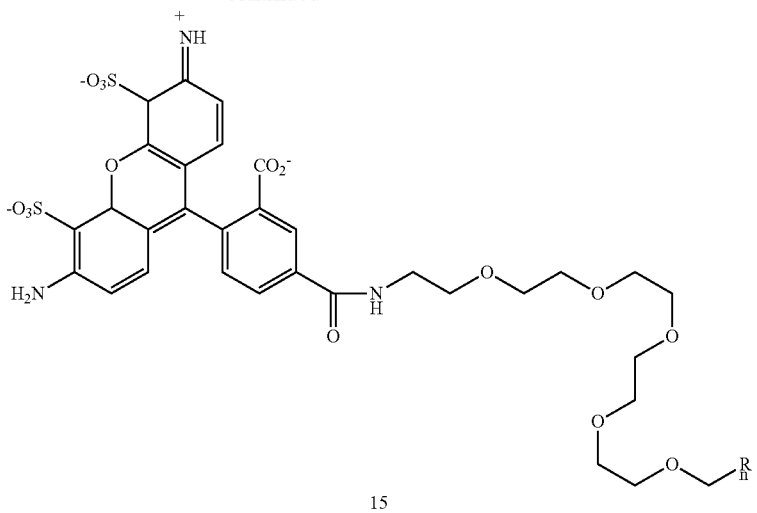
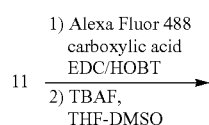
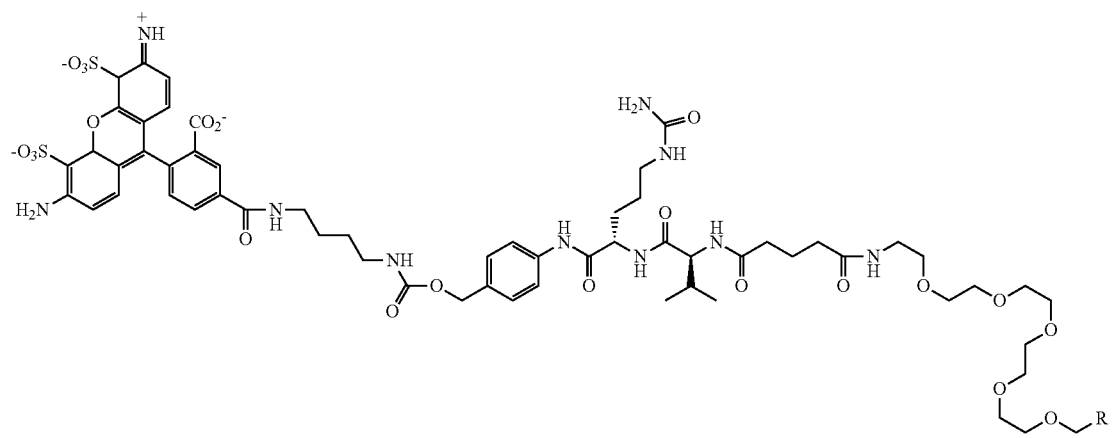
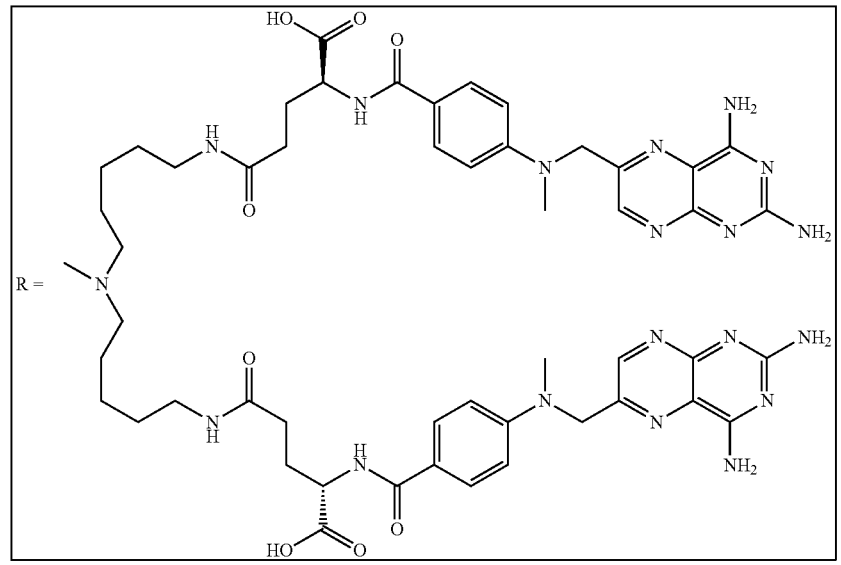
To facilitate tissue radiolabeling, MTX dimerizers conjugated to the chelator 1B4M-diethylene-triaminepentaaceticacid (DTPA) will be prepared. Several types of metallic radionuclide chelators have been developed for radioimmunotherapy. (Milenic et al., 2004) To avoid undo release of radionuclides and possible bone deposition or not target organ irradiation, it is important that the chelate be stable. IB4M-DPTA was chosen for these studies because it is highly stable in vivo. Conjugates of anti-CD19 and ant-CD22 MABs and IB4M-DPTA chelates of either $^{125}$I or $^{90}$Y have been prepared and shown to specifically bind and kill B-cell tumor (Daudi) in nude mice with no radiologic bone marrow damage. To investigate cell labeling and uptake of the antibody nanorings by fluorescence techniques, conjugates with the fluorophore, Alexa-488 will be prepared 15.a. Synthesis of Trivalent Dimerizer.

Important in the synthesis of MTX$^2$-conjugates will be the preparation of the trivalent linker, 5. Progress toward the synthesis of the 5 has been made. PEG5 was first monoprotected with trityl chloride, followed by mesylation 2 in 80% yield. After substitution of the mesyl group with sodium azide, followed by reduction with triphenyl reduction, the trivalent PEG5 bis-cyanobutylamine, 3, has been obtained in a 70% overall yield. Compound 4 has been obtained in 85% yield by reaction of 3 with 5-bromovaleronitrile in the presence of sodium bicarbonate, followed by deprotection of the trityl group. (White et al., 2005) Next, the PEG5 linker was extended by treatment of 4 with 2-bromoethylamine and sodium hydride. Following protection of the primary amine with t-butyl carbonyl anhydride, compound 5 will be obtained by reduction of the cyano groups with lithium aluminum hydride. (White et al., 2005) If necessary, PEG linkers of greater length and water solubility can be incorporated to enhance nanoring formation and cellular uptake.

Because of the need for greater flexibility with regard to protecting group removal, previous MTX$^2$ synthesis (Carlson et al., 2003) will be modified to include the protection of the di-protected glutamate, 6, with a trimethylsilyl ethyl moiety, instead of as a methyl ester. This strategy has been successfully applied to the synthesis of folate-drug and folate-phosphoramidite conjugates. Compound 7 will be prepared from 6 by treatment with the coupling agent carboxydimmidazole (CDI) and trimethylsilyl ethanol, followed by removal of the benzyl protecting group by hydrogenation, yielding 8. The silyl-protected glutamate will be coupled to 5 in the presence of EDC and HOBT and the Cbz protecting groups removed by catalytic hydrogention to yield 9. Next, 10 will be prepared by DEPC assisted coupling of to the free amine, followed by removal of the Boc group. We have found that this procedure is superior to standard EDC or DCC based methods.

To prepare the trivalent linker with the cathepsin B cleavable linker, the valine citruline p-aminobenzyloxycarbonyl butyl amine (PABOH-NH) peptide spacer (14) will be prepared. (Dubowchik et al., 2002) Starting with Fmoc protected valine (12), the Fmoc valine-citruline dipeptide will be synthesized by first activating 12 with N-hydroxy succinimide, followed by the addition of citrulline in sodium dicarbonate.$^{70}$ The dipeptide, 13, will be coupled to PABOH-NH-Boc in the presence of EEDQ. After removal of the Fmoc group with diethylamine, treatment with glutaric anhydride will yield 14. (Dubowchik et al., 2002) The final protease sensitive trivalent linker, 15 will be synthesized by coupling 14 and 10 in the presence of DIEA followed by removal of the Boc group with TFA. (Dubowchik et al., 2002)

15. b. Synthesis of MTX$^2$-Alexa Fluor 488

The preparation of a MTX dimer conjugated to a fluorophore will be carried out with Alexa Fluor 488 (Invitrogen-Molecular Probes, Inc.). Although fluorescein is widely used for cell based fluorescent ligand experiments, Alexa Fluor 488 will be used instead of fluorescein because of its greater fluorescence brightness, superior photo stability, excellent water solubility and enhanced pH (4-10) insensitivity. These qualities make it an excellent reagent for monitoring the cellular uptake of antibody-nanorings, particularly by FACS analysis and fluorescence microscopy. The primary amine of the PEG5 linker of 10 will be conjugated to Alexa Fluor 488 carboxylic acid, succinimidyl ester in the presence of EDC and HOBT. Yields from 65-75% have been observed for conjugations with primary and secondary amines.

To monitor not only cellular uptake, but lysosomal release, fluorogenic cathepsin B sensitive MTX$^2$ conjugates will be prepared. In a procedure similar to that outlined for the preparation of 15, compound 11 will be conjugated to Alexa Fluor 488 carboxylic acid, succinimidyl ester and the silyl protecting groups removed with TBAF to afford compound 16.

15. c. Synthesis of MTX$^2$-DPTA

Preparation of the MTX dimer conjugates to 1B4M-DPTA will be carried out by a procedure similar to that reported previously for 1B4M-DPTA immunoconjugates. IB4M-DPTA will be prepared from methyl 4-nitrophenylalanine hydrochloride and 1,2 diamino propane in three steps as previously reported. (Brechibiel et al., 1991) After removal of the silyl protecting groups with TBAF, compounds 10 and 11 will be treated with 1B4M-DPTA in a solution of THF and triethylamine to yield compounds 17 and 18. Typically, yields for isothiocynate conjugations range from 80-90%. Compound 18 will allow us to determine the advantage or disadvantage of radionuclide-chelate intracellular release from the MTX dimerizer on tissue labeling.

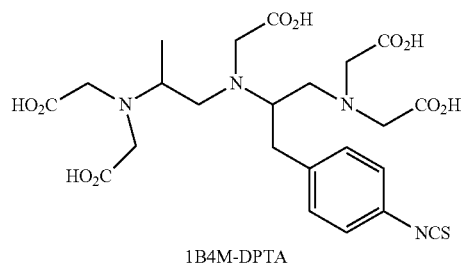

1B4M-DPTA

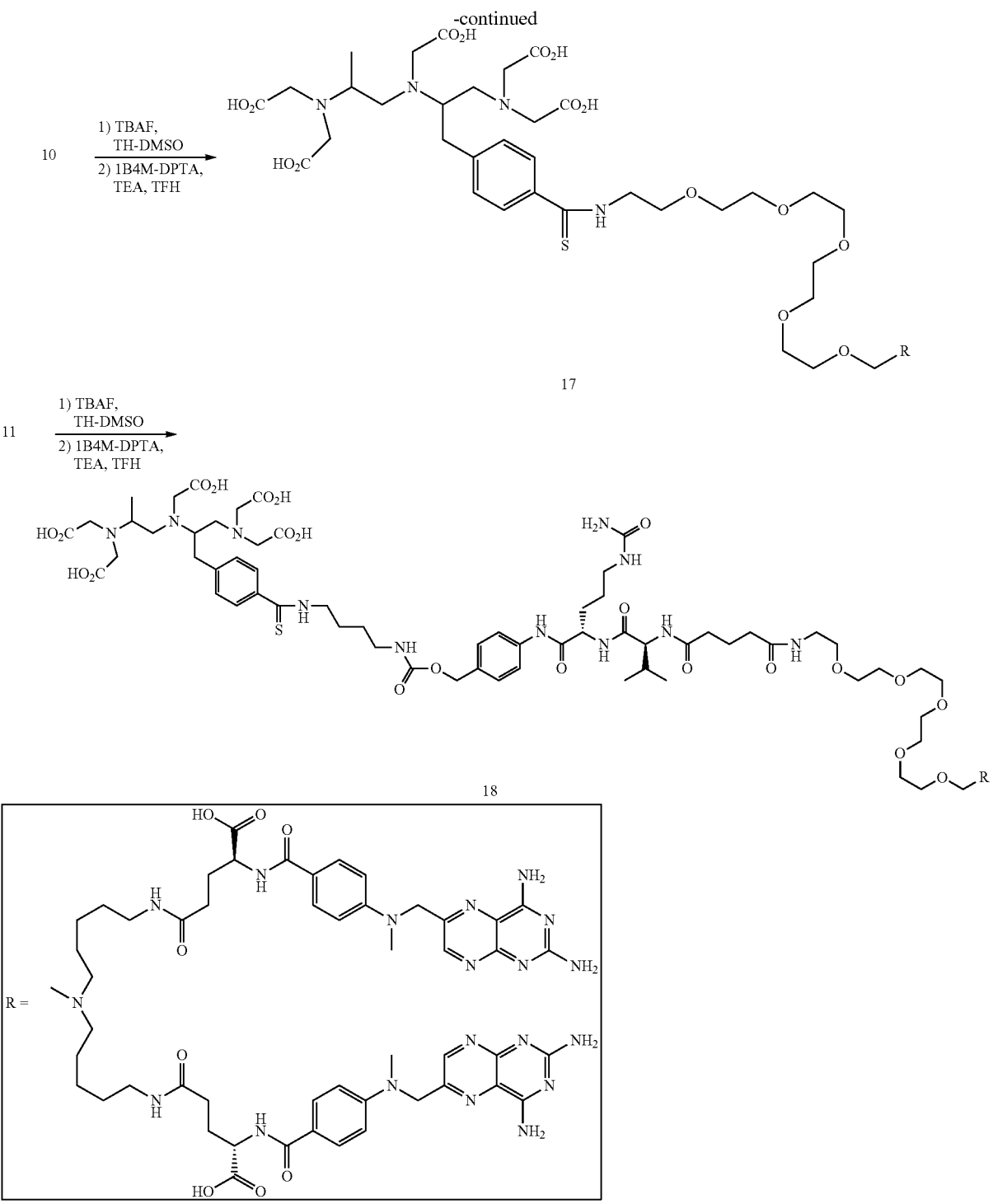

15. d. DHFR Dimerization Studies with Compounds 15-18

The ability of the MTX$^2$ compounds 15-18 to dimerize *E. coli* DHFR will be determined and compared to the previous results for MTX$^2$-C9 and MTX$^2$-C12. *E. coli* DHFR (5 uM) will be incubated in P500 buffer (0.5M NaCl, 50 mM potassium phosphate, 1 mM EDTA, pH 7.0) with 5% (v/v) glycerol for a minimum of 3 hr with varying amounts of the compound in final stoichiometric ratios of dimerizer:protein ranging from 0.1:1 to 50:1. The mixtures will be fractionated on a Sephadex G-200 size exclusion column, eluting with P500 buffer, and the amount of monomeric and dimeric protein quantitated by absorbance at 280 nm. Incubations from 30 min to 5 days yield identical results, indicating that equilibrium is reached within one hour. Microsoft Excel will be used to model the dimerization data as a function of free ligand concentration. The concentrations of the free enzyme and the remaining species will be derived with equation 1. (Carlson et al., 2003) It is expected that all of the compounds will efficiently and stably dimerize *E. coli* DHFR in a manner similar to that found for MTX$^2$-C9 and MTX$^2$-C12. If this does not occur, it is likely that the drug may be interfering with protein dimerization. Additional analogs incorporating longer PEG linkers (i.e., PEG6) will be synthesized and evaluated to address this potential issue.

$$[E] = \frac{-(1 + K_{a1}[D_a]) + \sqrt{(1 + K_{a1}[D_a])^2 + 8K_{a1}K_{a2}K_c[D_a]E_t}}{4K_{a1}K_{a2}K_c[D_a]}$$

15. e. Cleavage of DHFR-MTX$^2$-Drug Cathepsin B Linker

The efficacy of eventual drug delivery by the antibody-drug nanorings designed will depend on the efficiency with which the incorporated protease sensitive linker can be cleaved. Previously, immunoconjugates bearing this Val-Cit site have been shown to be excellent substrates for cathepsin B. Since each subunit of a nanoring is chemically dimerized DHFR, these experiments will be carried-out by determining the ability of DHFR dimerized by compounds 15-18 to release Alexa Flour 488 and 1B4M-DPTA. *E. coli* DHFR will be incubated with a final stoichiometric ratio of dimerizer: protein of 0.5:1. Non-bound dimerizer will be removed from the DHFR-Dimerizer complexes by centrifugation with PD-10 SEC column. Assay conditions will be chosen to approximate those of an intracellular lysosome. The DHFR-dimerizer complexes will be dissolved in PBS (pH 7.0) and diluted into the acetate/EDTA (pH 5.0) reaction buffer, followed by the addition of either human or mouse cathepsin B (R&D Systems). At various time points aliquots will be removed and the amount of MTX$^2$-1B4-DPTA or MTX$^2$-Fluorophore, 1B4M-DPTA or Fluorophore, and MTX$^2$ determined by HPLC after centrifugation. Half-lives will be calculated by calibration of the released 1B4-DPTA/Fluorophore peak areas with a standard curve of known 1B4M-DPTA or Fluorophore concentrations. Previously, >90% of a drug has been shown to be released from immunoconjugates that have incorporated cathepsin B sensitive linkers.[70]

EXAMPLE 16

Anti-CD22 DHFR-DHFR (DHFR$^2$) Based Polyvalent Nanorings

A variety of antigens have been used to develop antibody drug and radionuclide conjugates. For B-cell leukemias, several cell surface antigens, including CD19, CD20, CD22 and CD45 have been investigated as immunotherapy targeting antigens. The CD20 targeting Y-90 conjugated murine monoclonal antibody, Zevalin, was recently approved as the first radioimmunotherapeutic for B-cell leukemias, such as non-Hodgkin Lymphoma. Unfortunately, CD20 is not broadly expressed on less differentiated B-cell leukemias (B-ALL) and most common form of childhood leukemia. Currently therapies are able to cure approximately 80% of childhood B-ALL. The remaining 20%, however, do not respond to conventional therapy. The development of drug resistance is believed to be a significant factor in treatment failures. For adults the situation is bleaker, since only 40% of B-ALL patients are curable. Again, the development of drug resistance is a major contributor. Consequently, new modalities for the treatment of B-cell leukemias are urgently needed.

CD22 is a 135-kDa B lymphocyte specific glycoprotein and member of the sialoadhesin protein family. It functions as a regulator of B-cell responses, most probably by recruiting key signaling molecules to the antigen receptor complex. It is absent from hematopoietic cells and normal tissues, but expressed by late pre-B-cells, mature cells and 60%-70% of B-cell leukemias and lymphomas. Knockout mice experiments have demonstrated the importance of CD22 on modulating the B-cell antibody responses and expansion of peritoneal B-1 cell populations. The high level of CD22 expression on B-cell malignancies has made it an attractive target for the development of anti-cancer immunotoxins and radioimmunotherapeutics. Anti-CD22 scFv diphtheria toxin fusion proteins are potent and selective anti-B-cell leukemia agents, both in vitro and in vivo. (Vallera et al., 2005) In addition, a rapidly internalizing anti-CD22 MAB RFB4 (Kd=25 nM for Daudi cells[3]) was able to selectively deliver high-energy Y-90 radioactivity to human B-cells in vivo. (Vallera et al., 2005) However, due its slow clearance, radiolabeled anti-CD22 RFB4 is not useful as a radioimaging agent. This is expected, since the molecular weight of MAB (150 kDa) and Fc receptor directed antibody recycling decrease MAB renal clearance. Single-chain antibodies (25 kDa) and diabodies (50 kDa) have proven to be better imaging agents because of their shorter circulating half-life, but less effect as anti-tumor agents. Consequently, anti-CD22 scFv-DHFR$^2$ fusion proteins capable of self-assembling into di- (130 kDa,), tetra- (260 kDa) and octavalent (520 kDa) anti-CD22 scFv's will be prepared when mixed with MTX$^2$ radionuclide chelator/fluorophore conjugates and their in vitro and in vivo behavior will be determined. The larger size and multivalency should insure a greater half-life, while enhancing tissue binding and intracellular uptake. In contrast to existing methods of preparing large antibody complexes or antibody nanoparticles, a key advantage of this approach will be the ability to disassemble the nanoparticles into ≈65 kDa subunits with hydrodynamic radii of 4 nm and free MTX$^2$-chelator-radionuclide by treatment with the common antibiotic and *E. coli* DHFR inhibitor, trimethoprim.

Trimethoprim is a potent and selective inhibitor of *E. coli* DHFR (Kd=1.3 nM), and MTX is able to efficiently disassemble DHFR-MTX$^2$ complexes. To investigate the ability of trimethoprim to induce disassembly of DHFR$^2$ nanorings (16.5 min), DHFR$^2$ octamers were purified with a 2:1 excess of trimethroprim at 25° C., pH 7.0. Approximately 25% disassembled into smaller oligomers within 2 hr and 80% disassembly at the 13 hr time point. At the later time point substantial amounts of the monomer (21.7 min) were observable, indicating complete disassembly of a portion of the oligomeric DHFR$^2$.

Because of their considerably smaller size, both the antibody-DHFR$^2$ and MTX$^2$-chelator-radionuclide will be cleared considerably faster than the parent nanoring from the blood and organs. The ability to control the life-time of antibody-nanorings by assessing disassembly in vitro and in vivo will be determined 16.a. Construction of Plasmids for Expression Anti-CD22 sFv's with DHFR$^2$ Capable of Forming Bivalent, Tetravalent and Octavalent sFv-Nanorings.

DHFR$^2$-scFv fusion proteins that form predominately cyclic dimers, tetramers and octamers will be prepared with a well characterized anti-CD22 scFv and anti-CD3 scFv. Because CD3 is a T-cell specific antigen and thus unable to bind to B-cells, the specificity of the biological behavior of the anti-CD22 oligomers will be discernable when contrasted with that of anti-CD3 oligomers. In addition, a flexible 13 amino acid linker will be incorporated between the DHFR$^2$ and scFV. When fully extended, the linker will be able to extend at least 50 Å, thus providing a minimum range of at least 100 Å between two conjugated DHFR-DHFR-scFVs. Given that the distance between the variable ends of an average antibody is approximately 30 Å, the 13 amino acid linker should be sufficient. The DHFR²-scFv fusion proteins will be constructed by altering the plasmids that encode the DHFR² 13 amino acid (pF13DD), 3 amino acid (pF3DD) and glycine (pF1-GDD) linkers. The stop codon will be removed and a 13 amino acid linker (AGENLYFQ\GIGLD) (SEQ ID NO: 3) containing a TEV protease site inserted between the Xba I site and the end of the DHFR² gene by Quick Change™ insertion mutagenesis. After amplification of the gene for the anti-CD22 scFv from pUM22 and anti-CD3 from pUM3 with primers containing a 5'-XbaI site and 3'-Sac-I site, the respective PCR products will be double digested and ligated to the respective double digested plasmids. All plasmid sequences will be verified by double digestion with either XhoI, XbaI or SacI, followed by automated DNA sequencing of the linker and scFv regions.

ditions in solution. It is expected that the MTX chemical dimerizers of DHFR²-scFv's that have; 1) a 13 amino acid linker will form dimers, 2) a 3 amino acid linkers will form tetramers and 3) a glycine linker will form octamers.

Size-Exclusion Chromatography

For SEC analysis, the purified proteins and MTX²-C9 and compounds 15, 16, 17 and 18 will be mixed at a range of stoichiometries, allowed to equilibrate for one to twelve hours, applied to a Superdex G200 Column (Amersham, 10,000-600,000 MW range) and eluted with P500 phosphate buffer. Deconvolution of the chromatogram with the program Peak Fit (Systat, Inc.) will allow the amounts of the oligomeric species to be determined, when compared to a standard curve relating molecular weight to elution time. Preparative

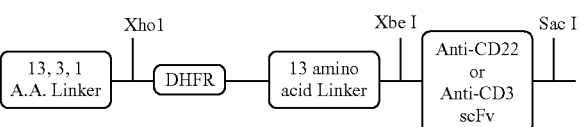

16.b. Expression and Purification of DHFR²-scFv Fusion Proteins

After transformation of the *E. coli* strain BL21(DE3) (Novagen) with the plasmids, p13CD3, p3CD3, p1-CD3, p13CD22, p3CD22 and p1-CD22, the following purification protocol for DHFR²-scFv's will be developed. The DHFR² fusion proteins will be expressed after the addition of IPTG for two hours and harvested by centrifugation. These conditions have been found to be optimum for the DHFR² proteins and scFv's. Although the DHFR² proteins are solubly expressed, the anti-CD3 and anti-CD22 scFv's are expressed in inclusion bodies. Regardless of the expression form, the DHFR²-scFv fusion proteins will be refolded using a sodium N-lauroyl-sarcosine air oxidation method. This method has been successfully used before for the incorporation of the internal disulfide bonds necessary for the correct refolding of scFv's, including the scFv's used in this study. Extensive protein folding and refolding studies have demonstrated that DHFR can be fully refolded after denaturation, without loss of enzymatic activity or the ability to bind MTX. In addition, DHFR, when appended to another protein, will fully refold independently of the adjacent protein. MTX affinity chromatography will be used to purify the soluble refolded protein in a single step and the percentage of fully functional DHFR assessed by MTX inhibitor titration of DHFR enzymatic activity. In the event the oxidative conditions required for scFV refolding interferes with DHFR refolding, Cys85-Ala, Cys152-Ser double mutants of both DHFR monomers will prepared, since it has been shown that this double mutant can be easily refolded without loss of catalytic activity or MTX binding affinity. (Iwakura et al., 1995 and Ionescu et al., 2000). In addition, neither Cys85 nor Cys152 are part of the group of residues involved in the induced protein-protein interface of the DHFR²-MTX² complex.

16.c. Evaluation of sFv-Nanoring Formation by Size Exclusion Chromatography (SEC) and Light Scattering (LS).

Although this mechanism of polymerization differs from both conventional non-reversible chemical polymers and from reversible biopolymers such as actin or tubulin, the fundamental descriptors of polymer shape, size, and kinetics apply. Size-Exclusion Chromatography (SEC), Light Scattering (LS) and TEM techniques will enable the characterization of DHFR²-scFv's-MTX² oligomers under equilibrium conditions amounts of protein nanorings will be obtained by gel filtration with a HiPrep Sephacyl S-400 column (Amershan, 10,000-2,000,000 MW range).

Light Scattering

Static and dynamic light scattering are powerful tools that allow the size and shape of oligomeric species to be determined. Measurements of the average radius of gyration and hydrodynamic radius will be determined by static and dynamic light scattering. Initial dynamic light scattering (DLS) studies will employ a custom-built apparatus, with a 50-200 mW 488 nm argon laser light source and data collection and analysis carried out with software from Brookhaven Instruments. Solutions of purified anti-CD22 DHFR²-scFv's will be ultrafiltered to remove dust and particulate, then mixed with equivalently filtered solutions of MTX²-C9 or the compounds 15, 16, 17, 18, in phosphate buffer. For concentration studies, the assembled mixture will be allowed to equilibrate for 15-20 minutes and then diluted with appropriate volumes of ultrafiltered buffer into individual aliquots.

For the DLS experiments, multiple angle scattered will be collected and the autocorrelated data analyzed by both cumulant and non-negative least squares (NNLS) regression analysis. For the NNLS calculation, the measured and calculated baselines will be compared, and the measured baseline used to derive the distribution of hydrodynamic radii (Rh). Raw scattering data for each sample will be collected a minimum of three times and analyzed independently, to control for the influence of dust-related, electronic, or photodynamic noise.

Static light scattering experiments will be conducted with the same apparatus, and the scattering intensity sampled at 10 degree increments from 30 to 130 degrees. Ultrafiltered toluene and phosphate buffer will serve as the reference and blank controls, respectively. Five to seven concentrations will be used for each experimental dataset, with concentrations spanning a minimum 4-fold range, typically from 0.2 to 1.2 mg/mL total protein concentration. The collected data will be analyzed by the Zimm plot method to determine the average molecular weight and radius of gyration (Rg) for each sample. Low polydispersion and a Rg/Rh ratio of 1.3 will indicate homogenous nanoring formation. High polydispersion and a Rg/Rh ratio approaching 1.9, will either indicate non-homogeneous nanoring formation or linear oligomer assembly. The results of these experiments will be correlated with the results from SEC. In general, we have found an excellent correlation between the results of SEC and LS experiments 16.d. Evaluation of sFv-Nanoring Formation by Transmission Electron Microscopy TEM.

TEM studies will be carried out as previously described herein. Cryo-TEM will also be used. The size and shape of the DHFR$^2$-scFv nanorings will be determined and compared to the results from SEC and LS experiments.

16.e. Determine the Kinetics of sFv-Nanoring Disassembly by the DHFR Inhibitor, Trimethoprim.

Trimethoprim is orally bioavailable and specific inhibitor of bacterial DHFR that has been clinically used for decades as a broad spectrum antibiotic. Because it is not an inhibitor of mammalian DHFR, it has proved to be a highly non-toxic drug. For example, when given orally to mice, the $LD_{50}$ is greater than 3 grams/kg. In humans, non-toxic blood concentrations of 5 μM to 50 μM have been observed, with a half-life of 11 hr. Consequently, the ability of DHFR$^2$ nanoring to undergo disassembly in the presence of trimethoprim both in vitro and in vivo will be determined. A 2:1 excess of trimethroprim was able to disassemble 80% of a solution DHFR$^2$ tetramer nanorings within 13 hr into DHFR$^2$ monomers. Blood concentrations of trimethoprim in mice, therefore, should be obtainable without observable toxicities.

At 37° C., purified DHFR$^2$ dimer, tetramer and octamer (10 nM) prepared from Cys152 FITC labeled monomer and MTX$^2$-C9 will be incubated in phosphate buffer or mouse plasma (pH 7.2) for 24 hr in the presence of variable concentrations (0-10 μM) of trimethoprim. At various time points an aliquot of the solution will be withdrawn and the amount of oligomer and monomer determined by SEC, plotted verses time and the rate of disassembly determined. Because of the abundance of interfering proteins expected for our plasma experiments, nanoring and monomer will be isolated by anti-1.5 FLAG immunochromatography before analysis by SEC. It is not expected that the decomposition kinetics for the DHFR$^2$ nanorings and antibody DHFR$^2$ nanorings will significantly differ. However, the rate of disassembly for the tetramer antibody-1B4M-DPTA oligomer in buffer and plasma will be determined. If a significant discrepancy is found, the rates of trimethoprim induced disassembly for the remaining antibody Nanorings will be determined. The ability of trimethoprim to alter the tissue distribution and clearance of the antibody-nanorings will be determined.

16.f. Characterize the Affinity of Anti-CD22 sFv Nanorings for B-Cell Leukemia Cells.

The binding affinity of the nanorings to cells will be determined. Binding (Kd) of the DHFR$^2$-scFv's nanorings assembled with MTX$^2$-C9 will be measured by homologous competition binding using radiolabeled parental antibodies anti-CD22 RFB4 RFB4 (Kd=25 nM). During these experiments the radioligand concentration will be held constant and the non-labeled ligand varied. The preparation of radiolabeled antibodies is a well established technique. GraphPad Prism software (GraphPad Software, Inc., San Diego, Calif.) is used to analyze the binding data by non-linear regression analysis. The technique and its use are discussed in the Prism manual entitled Analyzing data with GraphPad Prism (GraphPad Software, Inc.) Daudi cells (CD22+CD19+) will be used as targets since they are human lymphoma cells that express similar numbers of CD22 receptors (estimates show 20,000 to 40,000 per cell). The cell cultures will contain added thymidine as protection against the potential toxicity of the internalized MTX dimer. Kd's for the DHFR$^2$-scFv nanorings will be determined for each of the di-, tetra- and octavalent scFv nanorings and compared to the DHFR$^2$-scFvCD22 monomer and appropriate anti-CD3 nanorings, as well at the control parental antibodies, anti-CD22 RFB4. Comparing the binding constants generated in these studies will indicate whether oligomerization has reduced or enhanced binding affinity relative to; a) specific binding by the parental antibody, DHFR$^2$-scFv monomer and b) non-specific binding by control antibody nanorings.

Antibody-nanoring binding will also be evaluated by flow cytometry. DHFR$^2$-scFv's that have been assembled with the Alexa Fluor 488 MTX dimer, 15, will be prepared and incubated with the Daudi cells for 30 mins at 4° C. Cells treated with the three anti-CD22 DHFR$^2$-scFv's nanorings induced by 15 will be analyzed on a FACSCalibur with CellQuest Software (BD Biosciences, Mountain View, Calif.). Data will be expressed in standard histogram form showing cells versus increasing fluorescent intensity. The results will be compared to those for a control FLAG tagged anti-CD3 DHFR$^2$-scFv's nanorings and DHFR$^2$-scFv monomers and with the parental antibody, anti-CD22 RFB4.

Based on the results of the binding experiments, if binding has been enhanced or is unchanged compared to the parental antibody, oligomers will be prepared of the DHFR$^2$-scFv's assembled with the DPTA conjugates, 17 and 18, and characterized as outlined above. If binding of the antibody-nanorings prepared with 15-18 has been decreased relative to the parental antibody, the peptide linker between the scFv and DHFR$^2$ will be lengthened to better accommodate possible steric constraints hindering cell surface binding.

16.g. Determine the Ability of the Anti-CD22 sFv Nanorings to be Internalized by B-Leukemia Cells.

Understanding the trafficking of immunoconjugates is important to being able to predict biological activity. Previously, bi- and tetravalent anti-CD22 RFB4 has been shown to be internalized. The efficacy of internalization will be determined for the tightest binding DHFR$^2$-scFv nanorings and their organelle association. Daudi cells will be incubated with saturating amounts of DHFR$^2$-scFv nanorings that have been assembled with either MTX$^2$-C9 or the fluorescent conjugates 15 or 16, or the drug conjugates 17 and 18. At various time points, cells will be stained with mouse anti-FLAG IgG-FITC and analyzed by flow cytometry to detect the remaining level of surface bound nanorings. A progressive loss in the amount of surface fluorescence will be consistent with cellular uptake. In addition, the surface bound levels for antibody assemblies containing Alexa Fluor 488 conjugates 15 and 16 will also be monitored. Since the chemical dimerizer can dissociate from the complex when not bound to two DHFRs simultaneously, the rapid loss of Alexa Fluor 488 fluorescence relative to anti-FLAG-FITC fluorescence, would indicate cell surface nanoring instability. This is not expected, since even when effective molarity is not factored in, the dissociation constant DHFR from the DHFR$^2$-MTX$^2$ complex is estimated to be $>10^{-11}$ M or at least three orders of magnitude greater than anti-CD22 RFB4 binding to Daudi cells.[9] However, if the degree of cell surface nanoring loss is similar, then the antibody nanorings are likely internalized intact.

To further verify this and to gain insight into the internalization mechanism, Daudi cells will be incubated with the previously mentioned antibody nanorings at various time points, fixed and permeabilized to allow cellular localization to be determined by indirect fluorescence microscopy. Antibodies against the lysosomal marker Lamp-1/CD107a and the Golgi marker GM120 will be used to examine potential co-localization to these organelles, while mouse anti-FLAG will be used to detect the antibody nanorings. The possible importance of endocytosis by clathrin-coated pits or lipid raft pathways will be addressed with antibodies against the clathrin heavy chain or caveolin-1, respectively. Two possible results of microscopic analysis of localized fluorescence signals are likely to be observed. First, the signals could be well segregated and non-overlapping, indicating that the antibody nanorings are not efficiently internalized. Second, co-localization with Lamp-1, the clathrin heavy chain and/or caveolin-1 would be consistent with cellular internalization by endocytosis and trafficking to the lysosomal compartment. In addition, the loss with time of Alexa Fluor 488 fluorescence from antibody-nanorings prepared with 18 as well as co-localization with Lamp-1 will demonstrate that the protease sensitive linker is an intracellular substrate for cathepsin B. Thus radiolabel internalization by this mechanism is likely. Redesign of this linker may be necessary if loss of fluorescence and, therefore, cleavage is not observed.

16.h. The In Vitro Cytotoxicity of Anti-CD22 sFv Nanorings to B-Leukemia Cells

Although useful as targeting agents, anti-CD22 monoclonal antibodies, such as RFB4, do not have inherent antiproliferative activity. Nevertheless, cross linked anti-CD22 homodimers have been shown to be fully capable of inducing B-cell cancer cell-cycle arrest in vitro and preventing tumor growth in vivo. For example, while RFB4 was unable to inhibit the growth of Daudi cells in vitro, a homodimer of RFB4 induced $G_0/G_1$ arrest and proved to be a potent inhibitor of tumor cell growth in vivo. Consequently, the ability of $DHFR^2$-antiCD22 nanorings to inhibit the growth of Daudi cells will be determined.

Tumor cells will be evaluated for their sensitivity to di- tetra- and octavalent $DHFR^2$-antiCD22 nanorings prepared with both $MTX^2$-C9, 17 and 18. To evaluate the potency of the antibody-nanorings, cells will be incubated for 48 hr with various concentrations of the nanorings (1 nM to 1 µM), followed by the addition of 1 µCi of [H-3]-thymidine, harvested and counted by liquid scintillation. To assess the role of the MTX dimer on cell viability, a parallel set of experiments will be carried out with media supplemented with thymidine. Control experiments will be conducted with anti-CD22 RFB4 and the $DHFR^2$-anti-CD22 scFV monomers. $IC_{50}$ values will be determined by plotting the he percent radiolabel incorporation verses nanoring concentration relative to a non-treated control.

Previously, homodimers of anti-CD22, anti-CD20 and anti-CD22 have been shown to induce either apoptosis or $G_0/G_1$ arrest. To determine the mechanism of cellular toxicity induced by the antibody-drug nanorings, the degree of apoptosis and cell death will be determined by surface Annexin V binding and loss of PI exclusion, respectively. At 24 hr post drug exposure, the cells will be removed from culture and stained with Annexin V-FITC and PI. The amount of apoptotic cells (Annexin $V^+/PI^-$) and of dead cells (Annexin $V^+/PI^-$) will be determined by flow cytometeric analysis of each cell population. As was the case for cellular toxicity, the parental monoclonal antibody, $DHFR^2$-scFV monomer and antibody-nanorings will be compared.

To further probe the mechanism of toxicity, the effect of the antibody-nanorings on the cell cycle will be assessed by treating the cells as described above. However, shortly before harvesting the cultures will be treated with bomodeoxyuridine (BrdU) for 20 min. The cells will be fixed, permeabilized and the amount of nascent DNA synthesis determined by anti-BrdU-FITC, followed by staining with PI for total DNA content. Again, the effect of the parental monoclonal antibody, $DHFR^2$-scFV monomer and antibody-nanorings will be compared.

16.i. The In Vivo Pharmacokinetics and Biodistribution of Anti-CD22 sFv Nanorings The following set of experiments with In-111 radiolabeled antibody-nanorings will establish the relationship of size and valency on tumor localization. Radiolabeling of $DHFR^2$-anti-CD22 scFVs prepared with 17 will be carried out by incubating the antibody-nanorings with 5 to 10 µCi of In-111 chloride for 5-30 min. The labeled nanorings will be purified and the labeling efficiencies determined by HPLC size-exclusion chromatography with a Superdex G75 or G200 column. Although In-111 labeling of the parental antibody, anti-CD22 RFB4, has been shown to not interfere with immunoreactivity (>100%), the effect of radiolabeling on the scFVs is not known. The affinity of the labeled antibody-nanorings to Daudi ($CD22^+$) cells and HL60 ($CD22^-$) cells will be determined. The percent binding will be plotted verses cell number and the binding constants determined by scatchard analysis. It should be noted that the loss of antibody immunoreactivity due to radiolabeling is generally believed to result from deleterious conjugation of the chelator near or in the antibody binding site. Because the chelator is part of the protein dimerizer, radiolabeling is site specific. Thus, given the previous results with RFB4, it is highly unlikely that any effect of the radiolabeling on antibody-nanoring immunoreactivity will be observed. Nevertheless, losses of as much as 50% in immunoreactivity have been shown to not compromise in vivo binding efficiencies by recombinant scFVs.

The purified antibody-nanorings will be injected into groups of athymic nude mice and the pharmacokinetics determined by ELISA with anti-FLAG-HRP by serial blood measurements and In-111 labeling. Linear compartment models will be fit to data to estimate pharmacokinetic parameters, such as $t_{1/2}$, AUC, $Vd_{ss}$, Cl, MRT. SAS nonlinear regression program (PROC NUN) and SIPHAR program will be used for computer modeling. As controls, comparable experiments will be carried out with I-125 labeled $DHFR^2$ nanorings and $DHFR^2$-anti-CD3 scFV monomers will establish the effect of scFv oligomerization and targeting on clearance. The concentration of free 17 will be determined by HPLC by monitoring MTX fluorescence. Correlation of the amount of nanoring dosed with the amount of free $MTX^2$-1B4M-DPTA (17) will assess nanoring stability in vivo. The half-life of E. coli DHFR and E. coli DHFR bound to MTX in 80% mouse plasma at 37° C. is 10 hr and 22 hr, respectively. At 0° C., E. coli DHFR was found to be indefinitely stable. The stability of DHFR is evidently dependent on its intrinsic stability at 37° C. (i.e., unfolded vs. folded states), which the slow off rate of MTX enhances. Although, the nanorings are expected to have a substantially longer half-life, it may be necessary to further stabilize the protein by site-directed mutagenesis. (Iwakura et al., 1996 and Waschutza et al., 1996)

Given that the molecular weight and hydrodynamic radius cut-off for kidney filtration and readsorption has been found to range from 50-80 kDa and 4 to 6 nM, the di-(130 kDa, Rh=8 nn), tetra-(260 kDa, Rh=11 nm) and octavalent (520 kDa, Rh=17 nm) antibody nanorings should have greatly increased circulation times and therefore slower clearance rates. This should allow for improved tumor exposure and ultimately radiolabel uptake.

For biodistribution studies, athymic nude mice bearing Daudi flank tumors (6 per treatment group) will be given 7 µCi of the In-111 labeled di-, tetra- or octavalent $DHFR^2$-anti-CD22 scFV nanorings. On day 5, blood, tumor, spleen, liver, lung, kidney, muscle and bone will be harvested and counted. The data will be calculated as the percentage of the injected dose per grams of tissue (% ID/gram). The results will be compared with the previous results for In-111 labeled anti- CD22 RFB4, as well as results from comparable experiments carried out with DHFR$^2$-anti-CD3 scFV nanorings.

The way a targeted protein distributes throughout a tumor can indicate if further modifications are necessary. Immunohistochemical studies with anti-FLAG-FITC will be performed to determine how the antibody-nanorings distribute throughout tumors. Some antibodies distribute homogeneously and some bind to the first wall of antigen that they encounter after diffusion from the blood into the parenchyma. This data will be used to correlate affinity to the quality of tumor penetration. If the data reveal that the antibody is distributed homogenously throughout the tumor, the affinity of the antibody nanorings is sufficient.

The ability of trimethoprim to alter the pharmacokinetic/biodistribution of the antibody-nanorings will be examined by dosing animals at predetermined time points with trimethoprim (0.1-1 g/kg) after at least a 24 hr exposure of tumor bearing mice to the test antibody-nanoring. The amounts of free 17, monomer and oligomer present will be determined by either ELISA or HPLC as previously described. Since the monomers DHFR$^2$-scFV, have a molecular weight of 65 kDa, both the monomers and compound 17 should undergo renal clearance, thus providing a mechanism for removing the nanorings in vivo. The kinetics found for I-125 DHFR$^2$-anti-CD22 scFV monomers will be compared to the results for in vivo trimethoprim disassembly. As outlined above, a similar set of biodistribution studies will also be carried out after dosing mice for five days with the radiolabeled nanorings, followed by 24 hours with trimethoprim. It is expected that we will be able to find a minimum non-toxic dose of trimethoprim needed to effectively enhance nanoring and radiolabel clearance.

The results from these experiments will allow for estimating the correct dosing necessary for the following anti-tumor studies. In addition, if the major route of cellular internalization proceeds through lysosomal routing, a comparable set of biodistribution and pharmacokinetic studies will be conducted with antibody-nanorings prepared with compound 18. Chelators that have incorporated cathepsin B cleavable linkers have been shown to reduce liver accumulation of In-111 and Y-90, presumably due to increased catabolism. Consequently, studies with antibody-nanorings prepared with 18 will allow for the determination of whether incorporation of a cathepsin activatable linker enhances the tumor verses liver therapeutic index (TI) of the approach. Combining trimethoprim induced nanoring disassembly and radiolabel release with a cathepsin sensitive linker is likely to result in an even greater reduction in labeled antibody-nanoring toxicity, while optimizing tumor targeting.

16.j. Determine the In Vivo Antitumor Potency of the Anti-CD22 sFv Nanorings.

After characterization of the in vivo behavior of the anti-CD22 nanorings, antitumor therapy studies will be initiated with Y-90 labeled antibody-nanorings. Y-90 has been chosen because it is a powerful β-emitting radionuclide that is widely accepted as a radiotherapeutic agent. For example, Zevalin, an anti-CD20 murine monoclonal antibody currently FDA approved for the treatment of Non-Hodgkin Lymphoma, is labeled with Y-90. The favorable maximum β energy (2.3 MeV), reasonable half-life (2.7 days) and short path length (5 mm) have contributed to its well-known ability to treat bystander cells as well. In addition, because Y-90 is not a gamma emitter, the extensive precautions needed for other radionuclides, such as I-131, are not required. In addition, Y-90 labeled monoclonal antibodies have potent anti-cancer activity.

Y-90 labeled DHFR$^2$-anti-CD22 scFV nanorings will be prepared by essentially the same method described above for In-111. Athymic female nude mice will be injected in their flank with 5 million Daudi cells. When the tumors become apparent, they will be measured with calipers and their volumes determined. Typically, tumors have an average size of 0.5 cm$^3$. The mice will then be randomly separated in to treatment groups (n=6) and injected with approximately 75, 150 and 300 µCi of radiolabeled antibody-nanorings. As controls, mice will be treated with similar amounts of radioactive anti-CD3 nanorings and non-radioactive anti-CD22 nanorings. The optimal dose of Y-90 labeled anti-CD22 RFB4 was 151-262 µCi for athymic nude mice bearing Daudi tumors. Doses of 77 µCi were found not to be protective, while doses of 292 µCi resulted in little observable toxicity.

Given the greater valency of the tetra- and octavalent nanorings, it might be expected that they will be more potent at a lower dose of radioactivity. Because of their similar valency, it is not expect major differences in potency and toxicity between divalent antibody-nanorings and RFB4. In addition, based on the results of the proposed in vitro cellular toxicity experiments, the antitumor activity and toxicity observed for non-labeled anti-CD22 nanorings may indicate that the anti-CD22 nanorings have inherent antitumor activity, either due to the delivery of MTX or CD22 oligomerization, or both. The effect of dosing with leuvocorin (MTX rescue) on nanoring antitumor activity will delineate the role of MTX dimer toxicity on the in vivo antitumor response for both the Y-90 and non-radiolabeled nanorings. Consequently, the degree to which nanoring receptor oligomerization, MTX toxicity and radioactivity act synergistically or additively will be determined by such experiments.

EXAMPLE 17

DHFR$^2$-MTX$^2$ Heterodimer Building Blocks for Co-Polymeric Nanoring

The increase in avidity of monospecific multivalent antibody-drug nanorings target CD22+ cells may or may not enhance their anti-tumor activity relative to anti-CD22 RFB4. Diphtheria toxin has enhanced anti-B-cell leukemia activity and lower toxicity to non-targeted cells when fused to both anti-CD19 and anti-CD22 scFv's. In addition, Y-90 labeled anti-CD22 antibodies are potent inhibitors of the CD19+ CD22+ Daudi tumor cells in vivo. Like CD22, CD19 is a B-cell antigen that has been extensive studied as an immunotherapeutic target. The development, therefore, of DHFR$^2$-MTX$^2$'s assembled from heterodimeric monomers would provide a means to prepare bispecific multivalent antibody nanorings.

The ability of charge complementary double mutants at Ala-19 and Gln-23 will be examined to enforce chemically induced DHFR heterodimerization. Based on computer modeling analysis, these two residues are the most likely to facilitate side chain high pairing by the protein interface. The double mutants; Lys-19-Lys-23, Arg-19-Arg-23, Lys-19-Arg-23, Arg-19-Lys-23, Asp-19-Asp-23, Glu-19-Glu-23, Asp-19-Glu-23 and Glu-19-Asp-19 will be prepared. The ability of each to dimerize in the presence of MTX$^2$-C9 will be determined, as well as the ability of the "positively" charged mutants to heterodimerize with the "negatively" charged mutants. These interactions will be modeled and x-ray crystal structures of the homo and heterodimerized DHFR mutants will be obtained. Stable, self-assembling nanorings, polyvalent and bispecific antibody-nanorings will be produced.

17.a. Construction of Double Mutants.

To enable the characterization of both homo and heterodimeric pairs of DHFR, mutants will be prepared from a plasmid encoding the expression of a DHFR green fluorescence protein (GFP) fusion protein. Similar to DHFR$^2$ proteins, the GFP is not expected to interfere with dimerization. Because the molecular weight of GFP is approximately 30 kDa, unique dimeric species will be resolvable by SEC when a mutant DHFR-GFP is paired with a complementary mutant DHFR. The expression plasmid p13DGFP will be constructed PCR amplification of the GFP gene from and in house plasmid, pMSCV-MIGR1-IRES-eGFP, with primers encoding the XhoI and XbaI restriction sites. Both pF13DD and the GFP PCR product will be digested, the products purified and ligated. After removal of the FLAG peptide DNA sequence by Quick Change™ Deletion Mutagenesis, p13DGFP will be obtained. The double mutants, Lys-19-Lys-23, Arg-19-Arg-23, Lys-19-Arg-23, Arg-19-Lys-23, Asp-19-Asp-23, Glu-19-Glu-23, Asp-19-Glu-23 and Glu-19-Asp-19 of DHFR-GFP will be obtained in one step by Quick Change™ Mutagenesis. The same mutants of DHFR will also be prepared with the expression plasmid, p-TZ. Primers will be designed that are sufficiently long enough to insert both mutations simultaneously. If this strategy is not successful, both mutations will be inserted iteratively.

17.b. Analysis of Mutant Dimerization

Characterization of mutant dimerization will be carried by SEC. Unique values for $K_{eq}/K_c$ can be obtained from MTX competitive DHFR$^2$ disassembly experiments. Since the relative free energy of binding ($\Delta\Delta G$) for one monomer to another is proportional to the ratio of the $K_c(wt)/K_c(mutant)$ and the value of $K_{eq}$ is non-dependent value, the $\Delta\Delta G$ for binding can be calculated from the following expression.

$$\Delta\Delta G = -RT \cdot \ln(K_{eq}/K_c \text{mut}) - (-RT \cdot \ln(K_{eq}/K_c \text{wt}))$$

Consequently, the impact of the mutations on protein-protein interface thermodynamics will be assessed by comparing the $K_{eq}/K_c$ for each mutant to the value for wild-type. Typically, DHFR dimers will be pre-equilibrated (3+ hours) in GP500 buffer and mixed with increasing concentrations of monomeric MTX. Samples will be incubated for 48 hours after the addition of MTX, then assayed by SEC as described above. Data will be fit to the expression below with Mathematica (Wolfram Research), with manual optimization to obtain the best fit, $R^2$=0.998.

$$[E_2 D_{active}^*] = \frac{K_c K_{a1} K_{a2}(0.5 - [E_2 D_{active}^*])(1 - 2[E_2 D_{active}^*])^2}{K_{eq} K_{aMTX}^2 (M_t - E_t + 2[E_2 D_{active}^*])^2}$$

17.c. Mutant Heterodimerization

The ability of the "positively" charged mutants Arg-19-Arg-23, Lys-19-Arg-23 or Arg-19-Lys-23 to form heterodimers with the "negatively" charged mutants, Asp-19-Asp-23, Glu-19-Glu-23, Asp-19-Glu-23 and Glu-19-Asp-19 will be determined by SEC. A positively charged mutant DHFR will be mixed with a negatively charged mutant DHFR-GFP, the solution allowed to reach equilibrium and the amount of homodimer (40 kDa and 100 kDa) and heterodimer (70 kDa) determined. The complementary pairs will be ranked based on their ability to form 100% heterodimers at a MTX$^2$-C9 to protein ratio of 0.5:1.0. The relative free energy of binding will be determined for heterodimers meeting this criteria by competitive DHFR$^2$ disassembly with MTX as described above.

17.d. Computer Modeling of Homo and Heterodimerization

Despite the importance of understanding how proteins interact with one another, the development of effective ways of modeling protein-protein interfaces is still in its infancy. One of the major hurdles has been the inability to study structurally well-characterized systems in which the free energies of binding can be accurately determined for relatively weak (3-5 kcal/mol) sets of interactions. Even if this were the case, the modeler must still develop methods that will not result in the two proteins simply dissociating from one another, particular in explicit water. DHFR$^2$-MTX$^2$ provides an excellent system to develop approaches to modeling protein-protein interactions since; 1) high resolution structures of DHFR$^2$-MTX$^2$ complexes have been determined, 2) free energy of binding calculations can be validated by competition binding experiments, and 3) the individual monomers are tether together by the bivalent MTX with a picomolar dissociation constant.

Two methods will be implemented in order to estimate the stability of DHFR protein-protein interactions: calculating relative free energies of binding for wild-type and mutant DHFR dimers by means of molecular dynamics (MD) simulations followed by Poisson-Boltzmann or generalized Born continuum electrostatics; and calculating relative complexation energies of those dimers using MD in conjunction with molecular mechanics (MM) minimizations and/or free energy based sampling. In both methods, each MD simulation will run for 1-3 ns in 1 fs increments, at constant pressure and volume with temperature ramped from 100 K to an approximately physiological 310 K. All MD calculations will be done using CHARMm version c31b1 in the InsightII molecular modeling environment, with explicit solvent (modified TIP3P water model[113]), a periodic box of 70×70× 95 Å, and a van der Waals cutoff of 10 Å. Neutral charge will be obtained by placement of Na$^+$ counterions, and dielectrics will be treated by particle-mesh Ewald summation. The lowest-energy conformation will be extracted from each trajectory for further calculations.

The binding free energy $\Delta G_{bind}$ for each DHFR dimer is defined as $$\Delta G_{bind} = \Delta G_{ab} - \Delta G_a - \Delta G_b$$

where $\Delta G_{ab}$, $\Delta G_a$, and $\Delta G_b$ respectively correspond to the electrostatic solvation free energies of the dimer and each individual monomer. Electrostatic free energies for the dimer and monomers will be determined by the method of Roux et al., in which the Poisson-Boltzmann equation is solved numerically for the lowest-energy conformation of DHFR (wild-type and mutant) with a van der Waals radius of 25 Å or by generalized Born calculations.

The relative complexation energy $E_{compl}$ for each DHFR dimer is defined as $$E_{compl} = E_{ab} - E_a - E_b$$

where $E_{ab}$, $E_a$, and $E_b$ respectively refer to the molecular mechanics (MM) energies of the dimer and each individual monomer. A major advantage of this approach is that differences in entropy and solvation terms can be assumed to cancel out for structurally related compounds, which contributes to the accuracy of the calculated energies. A three-stage minimization process will be implemented in CHARMm in order to avoid unnatural or strained molecular conformations: first, the entire system is held rigid except for the hydrogens; second, only the sidechains are permitted to relax; and finally the entire structure is optimized. The TIP3P water model will be used for purposes of consistency. Each minimization will employ steepest descents to an energy change convergence criterion of 100 kcal/mol per iteration, and conjugate gradients thereafter until a convergence is reached at 0.001 kcal/mol per iteration. Alternatively, free energy differences can be estimated by carrying our appropriate sampling.

17. e. X-Ray Structure Analysis of Homo and Heterodimerized DHFRs

To fully characterize the molecular interactions important for heterodimer protein-protein interface design and to validate the modeling strategy, it is important to determine the structure of the monomer-monomer side-chain interactions. Consequently, the x-ray crystal structures of the dimerized mutant DHFR's will be determined.

Once the potent antibody drug nanorings are identified, their clinical utility will be improved by developing versions of the anti-tumor nanorings with reduced immunogenicity. It should be mentioned, however, that the clinical development of human anti-murine antibody (HAMA) responses to current murine monoclonal antibody based B-cell treatments, such as Zevalin, have been minimal (<2%). This is likely the result of the temporary suppression of the humoral immune response by the collateral suppression of normal mature B-cell proliferation. Little long term immunosuppressive has been observed. Nevertheless, methods will likely be utilized that have been established for the humanization of MABs, as well as scFv's. For the DHFR domains, the use of pegylation and/or humanization based on human DHFR will be investigated. Second generation DHFR heterodimeric developed will allow for the preparation of self-assembling co-polymeric nanorings capable of displaying more than one antibody specificity and therefore improving tissue targeting.

The imaging capabilities of the antibody-nanorings will be assessed by PET imaging. Nanoring NMR imaging will also be explored with paramagnetic metals like Gadolinium, which are also strongly chelated by DPTA. Although focused on B-cell leukemia, this approach will be applicable to other neoplasms, such as T-cell leukemias (anti-CD3 scFvs), lung cancer (anti-mesothelin scFvs) and breast cancer (anti-IGF1R scFvs).

Abbreviations. DHFR, Dihydrofolate Reductase, $DHFR^2$, DHFR-DFHR fusion protein, EDC, 1-Ethyl-3-(3-dimethylaminopropyl)-carbodiimide, FACS, fluorescence assisted cell sorting, FITC, fluorescein isothiocynate, HOBT, 1-Hydroxybenzotriazole hydrate, IGF, Insulin Growth Factor, IGF1R, Insulin Growth Factor Receptor, MTX, Methotrexate, $MTX^2$, Methotrexate dimer, MTT, 3-(4,5-dimethylthiazol-2-yl)-2,5-diphenyltetrazolium bromide, PI, Propidium iodide, scFV, single chain antibody, scFV-Fc, single chain antibody fused to an antibody Fc region.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention has been described with reference to various specific and preferred embodiments and techniques. However, it should be understood that many variations and modifications may be made while remaining within the spirit, and scope, of the invention.

All publications and patent documents cited herein are incorporated by reference, as though individually incorporated by reference.

LITERATURE

Brechibiel et al., Bioconj. Chem., 2, 187-194 (1991).

Carlson et al., JACS, 125, 1501-1507 (2003).

Carlson et al., JACS, 128, 7630-7638 (2006).

Dubowchik et al., Bioconjug. Chem., 13, 855-869 (2002).

Ercolani, Phys. Chem. B, 102, 5699-5703 (1998).

Ercolani, Phys. Chem. B, 107, 5052-5057 (2003).

Ionescu et al., Biochemistry, 39, 9550-9550 (2000).

Iwakura et al., J. Biochem., 117, 480-488 (1995).

Iwakura et al., J. Biochem., 119, 414-420 (1996).

Meng et al., Clinical Cancer Research, 10, 1274-1281 (2004).

Ghetie et al., PNAS, 94, 7509-7514 (1997).

Ghetie et al., Blood, 97, 1392-1398 (2001).

Milenic et al., Nat. Rev. Drug Disc., 3, 488-498 (2004).

Parker et al., Teterahedron, 59, 10165-10171 (2003).

Phanstiel et al., J. Med. Chem., 65, 5590-5599 (2000).

Sachdev et al., Cancer Research, 63, 627-635 (2003).

Sticha et al., Protein Expr Purif, 10, 141-153 (1997).

Vallera et al., Cancer Biother. Radiopharm., 19, 11-23 (2004).

Vallera et al., Clinical Cancer Research, 11, 3879-3888 (2005).

Vallera et al., Clinical Cancer Research, 11, 7920-7928 (2005).

Waschutza et al., Protein Eng., 9, 905-912 (1996).

White et al., Journal of Organic Chemistry, 70, 1963-1977 (2005).

Yeates et al., Cur. Opin. Struc. Biol., 12, 464-470 (2002).

Zhang et al., Cur. Opin. Chem. Biol., 6, 865-871 (2002).

What is claimed is:

1. A composition comprising:
   one or more compounds of formula I (A-$L_1$-B); and
   one or more compounds of formula II (X-$L_2$-Y);
   wherein;
   A is a polypeptide;
   B is a polypeptide;
   $L_1$ is a linker;
   X is a ligand that specifically binds to at least one of A or B;
   Y is a ligand that specifically binds to at least one of A or B; and
   $L_2$ is a linker,
   wherein one or more compounds of formula I are bound to one or more compounds of formula II to form an oligomer of formula III (A-$L_1$-B-X-$L_2$-Y)$_n$ wherein n is an integer from about 1-20.

2. The composition of claim 1, wherein A and B are the same polypeptide.

3. The composition of claim 1, wherein A and B are different polypeptides.

4. The composition of claim 1, wherein X and Y are the same ligand.

5. The composition of claim 1, wherein X and Y are different ligands.

6. The composition of claim 1, wherein n is an integer from 1-8.

7. The composition of claim 1, wherein at least one of A or B is a dihydrofolate reductase (DHFR) molecule.

8. The composition of claim 7, wherein the DHFR molecule is a wild-type DHFR molecule.

9. The composition of claim 7, wherein both A and B are wild-type DHFR molecules.

10. The composition of claim 7, wherein at least one of the DHFR molecules is a mutated DHFR molecule.

11. The composition of claim 7, wherein both of the DHFR molecules are mutated DHFR molecules.

12. The composition of claim 7, wherein the DHFR molecules are *E. coli* DHFR molecules.

13. The composition of claim 1, wherein $L_1$ is a polypeptide.

14. The composition of claim 13, wherein $L_1$ is from 1 to 13 amino acids in length.

15. The composition of claim 14, wherein $L_1$ is from 1 to 3 amino acids in length.

16. The composition of claim 1, wherein the compound of formula I further comprises at least one single chain variable region (scFv) fused to the compound of formula I.

17. The composition of claim 16, wherein the scFV selectively recognizes an antigen on a cancer cell.

18. The composition of claim 17, wherein the scFV is an anti-CD9, anti-CD22, or an anti-IGF 1R scFV.

19. The composition of claim 1, wherein at least one of X or Y is a methotrexate molecule, or an analog thereof.

20. The composition of claim 1, wherein the compound of formula II further comprises a therapeutic agent linked to $L_2$.

21. The composition of claim 20, wherein the therapeutic agent is an anticancer or antiviral agent.

22. The composition of claim 20, wherein the anticancer agent is doxorubicin or auristatin, or a radiotherapeutic agent.

23. The composition of claim 1, wherein the compound of formula II further comprises a detectable agent linked to $L_2$.

24. The composition of claim 1, wherein the oligomer is substantially linear.

25. The composition of claim 1, wherein the oligomer is substantially spherical.

26. The composition of claim 1, wherein the oligomer is a nanoring.

27. A fusion protein comprising two dihydrofolate reductase (DHFR) molecules linked via a linker, wherein the linker is a polypeptide.

28. The fusion protein of claim 27, wherein at least one of the DHFR molecules is a wild-type DHFR molecule.

29. The fusion protein of claim 28, wherein both of the DHFR molecules are wild-type DHFR molecules.

30. The fusion protein of claim 27, wherein at least one of the DHFR molecules is a mutated DHFR molecule.

31. The fusion protein of claim 27, wherein both of the DHFR molecules are mutated DHFR molecules.

32. The fusion protein of claim 27, wherein the DHFR molecules are *E. coli* DHFR molecules.

33. The fusion protein of claim 27, wherein the polypeptide is from 1 to 13 amino acids in length.

34. The fusion protein of claim 33, wherein the polypeptide is from 1 to 3 amino acids in length.

35. The fusion protein of claim 27, further comprising at least one single chain variable region (scFv) fused to fusion protein.

36. The fusion protein of claim 35, wherein the scFV selectively binds to an antigen on a cancer cell.

37. The fusion protein of claim 36, wherein the scFV is an anti-CD9, anti-CD22, or an anti-IGF 1R scFV.

38. An oligomer comprising a plurality of fusion proteins comprising two dihydrofolate reductase (DHFR) molecules linked via a linker and at least one methotrexate conjugate that comprises two methotrexate molecules, or analogs thereof, linked together by a linker.

39. The oligomer of claim 38, wherein the methotrexate conjugate further comprises a detectable group linked to the linker that links the two methotrexate molecules.

40. The oligomer of claim 38, wherein the methotrexate conjugate further comprises an additional agent linked to the linker that links the two methotrexate molecules.

41. The oligomer of claim 40, wherein the additional agent is a therapeutic agent.

42. The oligomer of claim 41, wherein the therapeutic agent is an anticancer or antiviral agent.

43. The oligomer of claim 41, wherein the anticancer agent is doxorubicin or auristatin or a radiotherapeutic agent.

44. The oligomer of claim 38 that is substantially linear.

45. The oligomer of claim 38 that is substantially spherical.

46. The oligomer of claim 38 that is a nanoring.

47. The oligomer of claim 38 that is a dimer, a trimer, a tetramer, and pentamer, or an octamer.

48. The oligomer of claim 38, wherein the oligomer comprises a plurality of fusion proteins that comprise at least one single chain variable region (scFv).

49. A composition comprising:
one or more compounds of formula I ($A-L_1-B$); and
one or more compounds of formula II ($X-L_2-Y$);
wherein;
A is a polypeptide;
B is a polypeptide;
$L_1$ is a linker, wherein $L_1$ is a polypeptide;
X is a ligand that specifically binds to at least one of A or B;
Y is a ligand that specifically binds to at least one of A or B; and
$L_2$ is a linker.

50. The composition of claim 49 in which one or more compounds of formula I are bound to one or more compounds of formula II to form an oligomer of formula III ($A-L_1-B-X-L_2-Y$)$_n$ wherein n is an integer from about 1-20.

51. The composition of claim 49, wherein A and B are DHFR molecules.

52. The composition of claim 51, wherein the compound of formula I further comprises at least one single chain variable region (scFv).

53. The composition of claim 49, wherein X and Y are methotrexate molecules.

54. The composition of claim 53, wherein the compound of formula II further comprises a therapeutic agent linked to $L_2$.

55. The composition of claim 53, wherein the compound of formula II further comprises a detectable group linked to $L_2$.

56. The composition of claim 50, wherein the oligomer is substantially linear.

57. The composition of claim 50, wherein the oligomer is substantially spherical.

58. The composition of claim 50, wherein the oligomer is a nanoring.

* * * * *

UNITED STATES PATENT AND TRADEMARK OFFICE
CERTIFICATE OF CORRECTION

PATENT NO. : 8,236,925 B1
APPLICATION NO. : 11/511186
DATED : August 7, 2012
INVENTOR(S) : Wagner It is certified that error appears in the above-identified patent and that said Letters Patent is hereby corrected as shown below:

In the Specifications:

In Column 1, Line 11-12, in the Statement of Government Support, please replace the existing text with the following clause:

This invention was made with government support under CA89615 awarded by the National Institutes of Health. The government has certain rights in the invention.

Signed and Sealed this
Twenty-third Day of July, 2013

Teresa Stanek Rea
*Acting Director of the United States Patent and Trademark Office*